US012583908B2

(12) United States Patent
Fleishman et al.

(10) Patent No.: US 12,583,908 B2
(45) Date of Patent: Mar. 24, 2026

(54) ALBUMIN PROTEIN VARIANTS, PRODUCTION THEREOF AND USES OF SAME

(71) Applicant: Yeda Research and Development Co. Ltd., Rehovot (IL)

(72) Inventors: Sarel Fleishman, Rehovot (IL); Olga Khersonsky, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 19/023,442

(22) Filed: Jan. 16, 2025

(65) Prior Publication Data

US 2025/0154227 A1     May 15, 2025

Related U.S. Application Data

(63) Continuation of application No. PCT/IL2023/050724, filed on Jul. 11, 2023.

(60) Provisional application No. 63/448,705, filed on Feb. 28, 2023.

(30) Foreign Application Priority Data

Jul. 18, 2022     (IL) .......................................... 294849

(51) Int. Cl.
C07K 14/765     (2006.01)
A61K 47/64     (2017.01)

(52) U.S. Cl.
CPC .......... C07K 14/765 (2013.01); A61K 47/643 (2017.08)

(58) Field of Classification Search
None
See application file for complete search history.

(56) References Cited

U.S. PATENT DOCUMENTS

| | | | |
|---|---|---|---|
| 5,612,196 A | | 3/1997 | Becquart et al. |
| 2018/0186858 A1 | | 7/2018 | Chaudhuri et al. |
| 2018/0194801 A1 | | 7/2018 | Yang et al. |
| 2019/0216079 A1 | | 7/2019 | Jorgensen |

FOREIGN PATENT DOCUMENTS

| | | | | |
|---|---|---|---|---|
| CN | 105861515 | * | 8/2016 | ............. C12N 15/14 |
| EP | 0683233 | | 11/1995 | |
| IL | 294849 | * | 7/2022 | |
| KR | 10-2019-0109947 | | 9/2019 | |
| WO | WO 00/44772 | | 8/2000 | |
| WO | WO 2018/096396 | | 5/2018 | |
| WO | WO 2024/018452 | | 1/2024 | |

OTHER PUBLICATIONS

International Search Report and the Written Opinion Dated Nov. 16, 2023 From the International Searching Authority Re. Application No. PCT/IL2023/050724 (16 Pages).
Search Report Dated Feb. 22, 2023 From the Israel Patent Office Re. Application No. 294849. (3 Pages).
Khersonsky et al. "Stable Mammalian Serum Albumins Designed for Bacterial Expression", Journal of Molecular Biology, XP93083919, 435(17): 168191, Sep. 1, 2023.
Latta et al. "Synthesis and Purification of Mature Human Serum Albumin from E. Coli", Nature Biotechnology, 5:1309-1314, Dec. 1, 1987.
Nguyen et al. "Bacterial Overexpression and Purification of Soluble Recombinant Human Serum Albumin Using Maltose-Binding Protein and Protein Disulphide Isomerase", Protein Expression and Purification, 167: 1-27, Mar. 2020.
Saunders et al. "Secretion of Human Serum Albumin from Bacillus Subtilis", Journal of Bacteriology, 169(7): 2917-2925, Jul. 1, 1987.
Sharma et al. "Revisiting *Escherichia coli* as Microbial Factory for Enhanced Production of Human Serum Albumin", Microbial Cell Factories, 16: 173, pp. 1-19, Oct. 5, 2017.

* cited by examiner

*Primary Examiner* — Phuong Huynh

(57)     ABSTRACT
An albumin protein is provided. The albumin protein is soluble when expressed in bacteria and characterized by increased thermostability as compared to wild type human serum albumin (HSA). Also provided are nucleic acid molecules encoding the albumin protein, compositions comprising the albumin protein and uses thereof.

7 Claims, 26 Drawing Sheets
(26 of 26 Drawing Sheet(s) Filed in Color)

Specification includes a Sequence Listing.

ALBUMIN PROTEIN VARIANTS, PRODUCTION THEREOF AND USES OF SAME

RELATED APPLICATIONS

This application is a Continuation of PCT Patent Application No. PCT/IL2023/050724 having International filing date of Jul. 11, 2023, which claims the benefit of priority of Israel Patent Application No. 294849 filed on Jul. 18, 2022 and U.S. Provisional Patent Application No. 63/448,705 filed on Feb. 28, 2023. The contents of the above applications are all incorporated by reference as if fully set forth herein in their entirety.

SEQUENCE LISTING STATEMENT

The XML file, entitled 102192SequenceListing.xml, created on Nov. 25, 2024, comprising 39,178 bytes, submitted concurrently with the filing of this application is incorporated herein by reference.

FIELD AND BACKGROUND OF THE INVENTION

The present invention, in some embodiments thereof, relates to albumin protein variants, production thereof and uses of same.

Serum albumin is a monomeric non-glycosylated 67 kDa transport protein that is highly abundant in mammalian plasma (35-55 gr/L). It folds into a canonical heart-shaped structure comprising three helical domains, with a conserved set of 17 disulfide bridges (FIG. 1A). Serum albumin is the main blood carrier for metabolites, hormones, drugs, and some cations. It has seven binding sites for fatty acids and three major binding sites for other small molecules.

Crystallographic analyses reveal two major conformations for albumin (compact and myristate-bound) (FIG. 1B). Besides ligand binding, serum albumin has a role in regulation of plasma colloid oncotic pressure, and has some catalytic properties. (2-4)

In addition to ligand binding, serum albumin has a role in stabilizing the extracellular fluid volume.

In addition to their physiological importance, human and bovine serum albumins (HSA and BSA, respectively) have many biochemical and pharmacological applications. Already in 1940, they were used to minimize osmotic shock after bleeding in patients. Additional clinical uses include vaccine preparations and treatment of burn injuries, hemorrhagic shock, hypoproteinemia, and ascites resulting from liver cirrhosis. HSA and BSA are also used in a range of biochemical procedures, such as immunological (e.g. ELISA), radioimmunological and immunoenzyme assays, as a blotting reagent, and as a molecular weight standard. Albumin is also widely used in molecular biology to stabilize the reactants and to prevent their adhesion to surfaces (NEB site). Finally, HSA and BSA are widely used as cell culture medium supplements, and have an increasingly important role in the cultured meat industry. Other novel biological applications include nanodelivery of drugs, oxygen carrier, peptide fusion.

Most albumin used in research and applications is derived from animal plasma. Animal-sourced albumin, however, increases the risk of DNA and viral contamination and batch-to-batch variability. This and serious ethical problems have encouraged the development of non-animal recombinant sources of albumin. Recombinant BSA and HSA from yeast and rice are now used to replace plasma-derived albumin. These expression systems are laborious and expensive [He et al (2011) Proceedings of the National Academy of Sciences. 108, 19078-19083; Zhu et al. (2018) Protein Expr. Purif. 147, 61-68].

Bacterial expression systems are amenable to high-throughput screening and mass production. Bacterially-expressed albumin variants may also serve as superior starting points in the development of albumin mutants with desirable carrier properties for therapeutic purposes.

Bacterial expression of albumin is challenging, however, potentially due to its large size, multidomain organization and 17 disulfide bonds. Indeed, bacterial expression of HSA was attempted in several studies, and some success was achieved in obtaining HSA from inclusion bodies [Latta et al. (1987) *Nature Biotechnology.* 5, 1309-1314], and as a fusion to maltose-binding protein [Nguyen et al. (2020) *Protein Expr. Purif.* 167, 105530].

To date there is no efficient bacterial expression system for albumin.

Additional Related Background Art

US20190216079;
US20180194801;
Saunders, C. W. et al, *J. Bacteriol.* 169: 2917-2925, (1987);
WO 00/44772;
EP 0683233;
U.S. Pat. No. 5,612,196;
US 20180186858.

SUMMARY OF THE INVENTION

According to an aspect of some embodiments of the present invention there is provided an albumin protein variant comprising:
(i) an amino acid sequence at least 85% identical to SEQ ID NO: 1;
(ii) mutations set forth in H39L, L42M, V120P, F156Y, D187E, L198H, S202I, V310I, A371S, V381I, V409I, S427A, V455I, K519E, A552S and V576I, where the coordinates correspond to the SEQ ID NO: 1; and
wherein the albumin protein is soluble when expressed in bacteria and characterized by increased thermostability as compared to wild type human serum albumin (HSA) of SEQ ID NO: 1.

According to some embodiments of the invention, the protein binds a small molecule albumin ligand in at least the same affinity as wild type HSA of SEQ ID NO: 1.

According to some embodiments of the invention, the small molecule is warfarin or Ketoptofen.

According to some embodiments of the invention, the albumin protein is folded as HSA as evidenced by the ability to bind myristate.

According to some embodiments of the invention, the protein supports cell growth in culture.

According to some embodiments of the invention, the protein further comprises at least one mutation at albumin binding sites.

According to some embodiments of the invention, the at least one mutation is selected from the group consisting of K136N, V216I, A254M, V344T, H440L, A449I, S470N A528F and V547I, According to some embodiments of the invention, the protein further comprises at least one mutation selected from the group consisting of Q33K, D38E, N44K, T52K, S58T, T76Q, E95D, N99H, V116E, T125K, A163K, A172E, E184A, A191E, D259K, K286R, E297D, M298K, A300E, S304P, G328A, M329R, L349I, T355D, A362K, A364E, F374E, D375E, P379K, P384T, Q397K, K402Y, V415M, S419P, P421D, V426L, S427T, A443E, M446L, P486H, I513L, K524M, T527K, K541E, D562E, K564P, K573S and A578K.

According to some embodiments of the invention, the protein is at least 95% identical to SEQ ID NO: 1.

According to some embodiments of the invention, the protein is at least 99% identical to SEQ ID NO: 1.

According to some embodiments of the invention, the protein comprises the amino acid sequence set forth in SEQ ID NO: 3, 5 or 7.

According to some embodiments of the invention, the protein comprises a heterologous tag.

According to some embodiments of the invention, the protein is tagless.

According to some embodiments of the invention, the protein exhibits increased yield than the wild type protein (SEQ ID NO: 1) when expressed in bacteria.

According to an aspect of some embodiments of the present invention there is provided an albumin protein comprising:

(i) an amino acid sequence at least 85% identical to SEQ ID NO: 9;

(ii) mutations set forth in G21A, S28A, H39L, L42M, L138I, V163I, G174A, M184I, I202L, V230I, A309L, V380I, V408I, S426T, T518E and V575I, where the coordinates correspond to the SEQ ID NO: 9; and wherein the albumin protein is soluble when expressed in bacteria and characterized by increased thermostability as compared to wild type bovine serum albumin (BSA) of SEQ ID NO: 9.

According to some embodiments of the invention, the protein further comprises at least one mutation at albumin binding sites.

According to some embodiments of the invention, the at least one mutation is selected from the group consisting of V240I, H241Y, A253M, A260V, V344L, V414M, V425I, K439L, M445L, P485H, A527F, V546I and V551T.

According to some embodiments of the invention, the protein further comprises at least one mutation selected from the group consisting of Q33K, E45D, T52K, A60P, E63S, A78E, S79E, E92S, S109N, D124K, A128E, N158K, G162K, T183A, L189KE226P, V228E, D258K, K285R, K294N, A296D, N300DA321D, S328R, A361K, T371R, D374E, H378K, L379H, N385E, R412K, S418P, P420D, T438Q, S442E, E443K, S426T, A500P, E503P, D517P, T526K, A559K, D561E, V569E, V576E, S577K and T580A.

According to some embodiments of the invention, the protein is at least 95% identical to SEQ ID NO: 9.

According to some embodiments of the invention, the protein is at least 99% identical to SEQ ID NO: 9.

According to some embodiments of the invention, the protein comprises the amino acid sequence set forth in SEQ ID NO: 11, 13 or 15.

According to some embodiments of the invention, the protein comprises a heterologous tag.

According to some embodiments of the invention, the protein is tagless.

According to some embodiments of the invention, the protein is immobilized to a solid support.

According to an aspect of some embodiments of the present invention there is provided a polynucleotide comprising a nucleic acid sequence encoding the protein as described herein.

According to an aspect of some embodiments of the present invention there is provided a cell comprising the polynucleotide and/or protein as described herein.

According to an aspect of some embodiments of the present invention there is provided a composition comprising the protein as described herein and an active ingredient.

According to some embodiments of the invention, the active ingredient is a protein.

According to some embodiments of the invention, the active ingredient is a drug.

According to some embodiments of the invention, the active ingredient is attached to the protein.

According to some embodiments of the invention, the composition is shaped as a tube.

According to an aspect of some embodiments of the present invention there is provided a method of producing albumin, the method comprising expressing in bacteria a nucleic acid sequence encoding the protein as described herein, thereby producing albumin.

According to some embodiments of the invention, the expressing is in an inducible manner.

According to some embodiments of the invention, the method further comprises isolating the protein from the bacteria or conditioned medium thereof.

According to an aspect of some embodiments of the present invention there is provided a method of cell culturing, the method comprising culturing cells in the presence of an albumin protein as described herein.

According to some embodiments of the invention, the culturing is in serum-free medium or in the presence of serum up to 2%.

According to some embodiments of the invention, the cells are eukaryotic cells and optionally mammalian cells.

According to some embodiments of the invention, the cells are hybridoma cells.

According to some embodiments of the invention, the cells are bovine cells, chicken cells, duck cells, fish cells or pig cells.

According to some embodiments of the invention, the cells are stem cells or progenitor cells.

According to some embodiments of the invention, the cells are differentiated cells.

According to some embodiments of the invention, the albumin protein is formulated with any of a fatty acid, a vitamin, a hormone or an ion.

According to an aspect of some embodiments of the present invention there is provided a method of isolating an albumin binding molecule of interest, the method comprising contacting a sample which may comprise an albumin binding molecule with the albumin as described herein under conditions which allow complexation.

According to an aspect of some embodiments of the present invention there is provided a method of facilitating a molecular biology reaction with a nucleic acid molecule, the method comprising contacting the albumin protein as described herein with the nucleic acid molecule to thereby facilitate the molecular biology reaction.

According to some embodiments of the invention, the reaction is restriction, amplification and/or sequencing.

According to an aspect of some embodiments of the present invention there is provided a composition comprising a research reagent and the albumin protein as described herein.

According to some embodiments of the invention, the research reagent is selected from the group consisting of a buffer, an enzyme and a cell culture medium.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figures 1A, 1B:
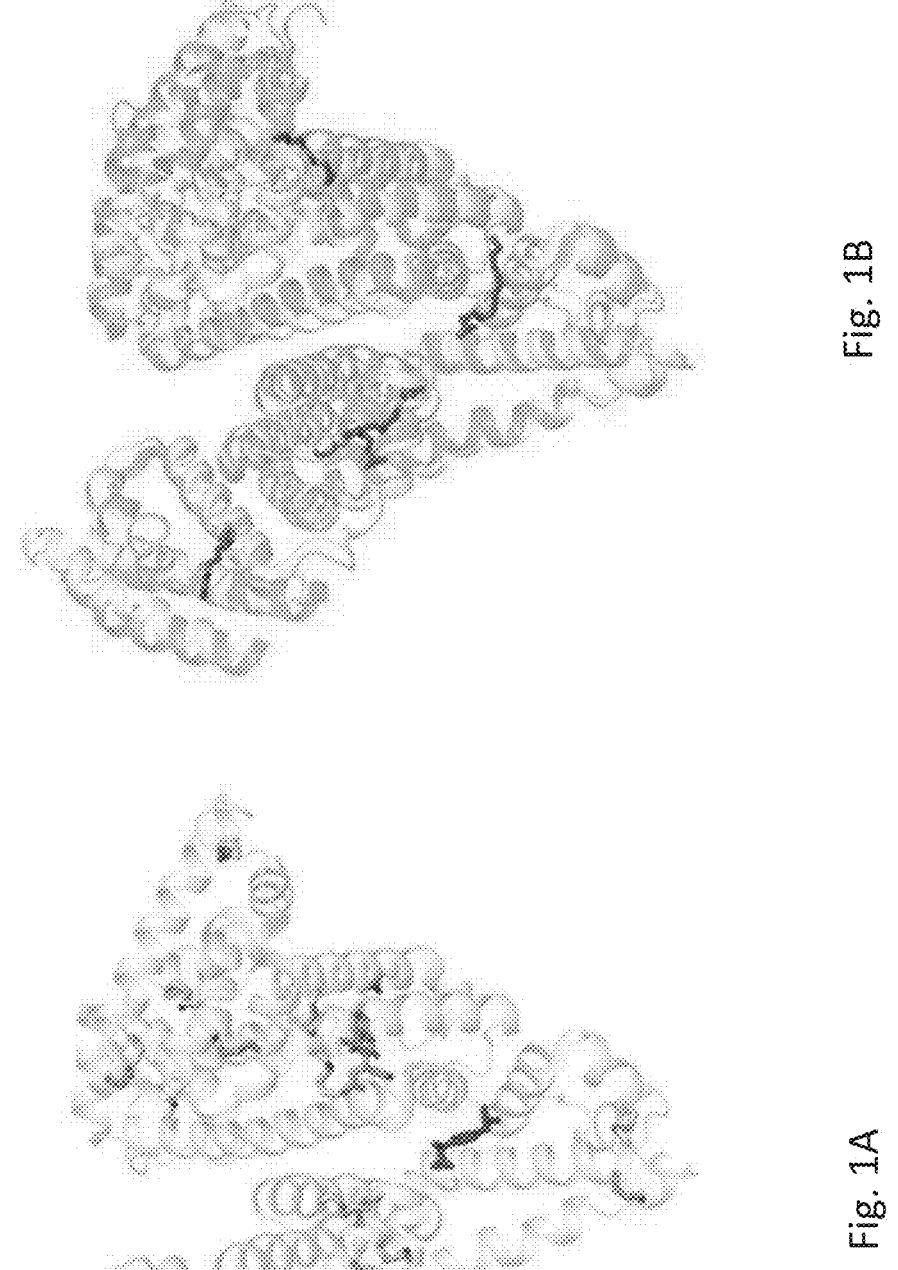
FIG. 1A shows albumin structure, compact conformation without myristate (pdb ID 2bxg), with disulfide bonds forming cysteines shown in grey sticks, ibuprofen in blue sticks (Sudlow site I), and warfarin in green sticks (overlaid from pdb ID 2bxd).
FIG. 1B shows albumin structure, open conformation (pdb ID 2bxi), with myristate molecules shown as pink sticks.
Figures 2A, 2B:
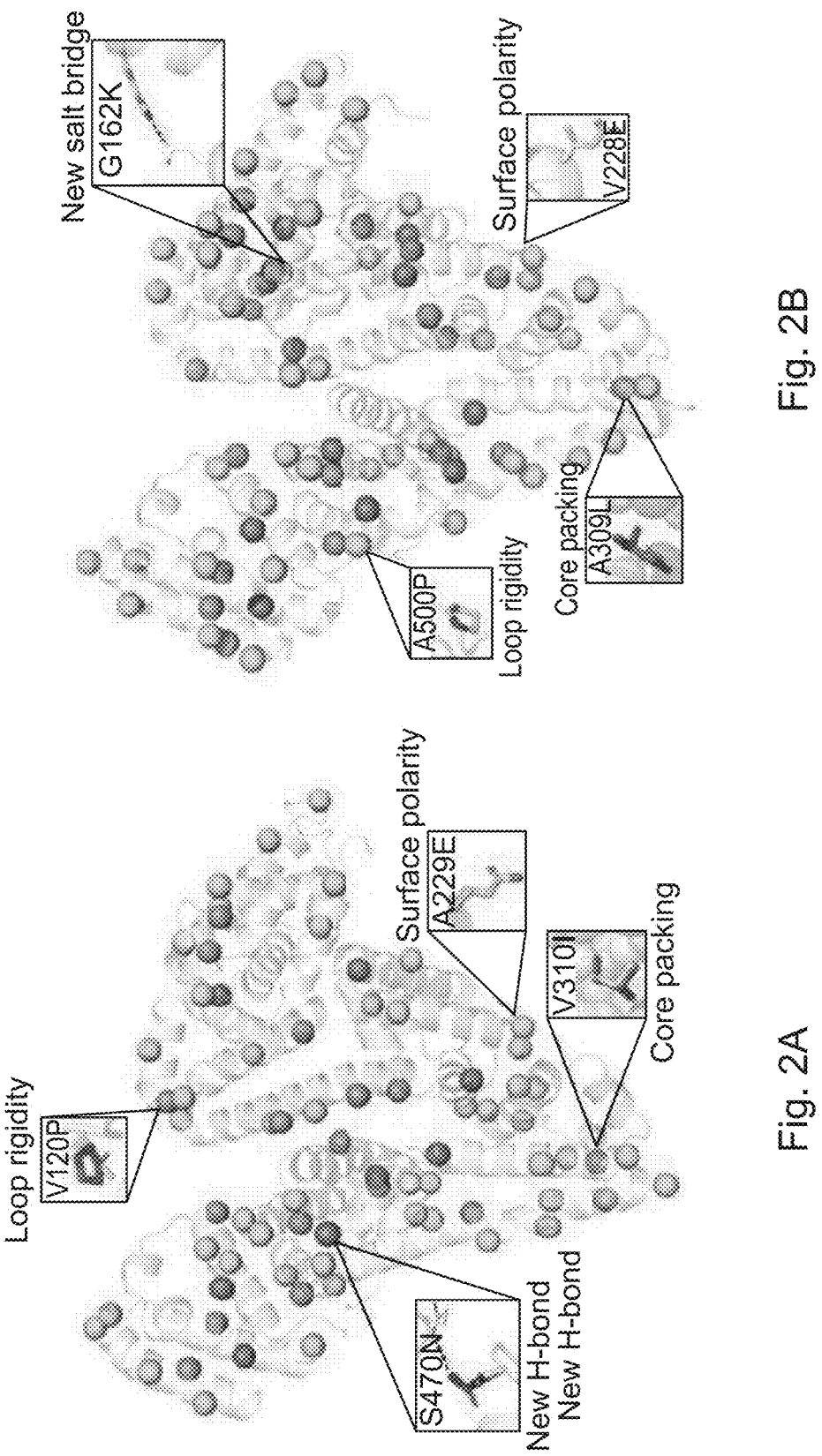

FIGS. 2A-B show mutations in stabilized albumin variants. Design models with mutations depicted as spheres. Pink spheres—mutations in HSA1; teal spheres—additional mutations in HSA2, and yellow spheres—additional mutations in HSA3. Thumbnails indicate the stabilizing effects of selected mutations.

Figure 3:

FIG. 3 shows crystal structure of HSA1. Shown is the crystal structure of HSA1 (pink), overlaid with the structure of HSA with myristate (green, pdb ID 2bxi). The four myristate molecules and warfarin are shown as magenta sticks.

Figure 4:
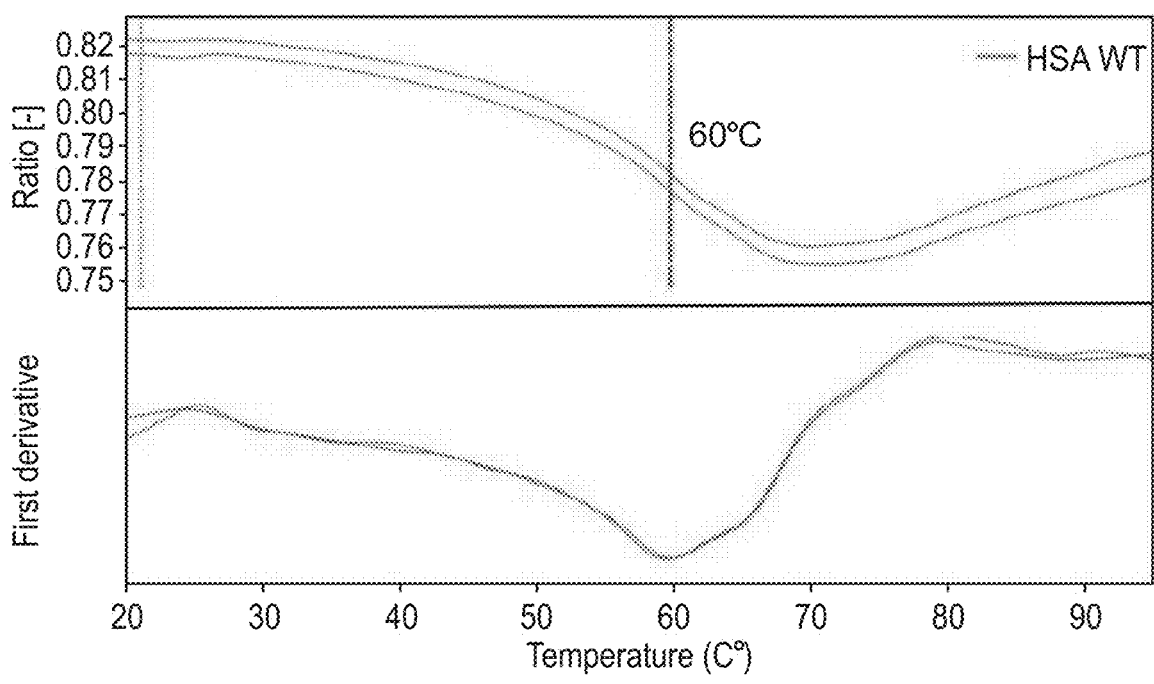

FIG. 4 shows nanoDSF of HSA WT variant.

Figure 5:
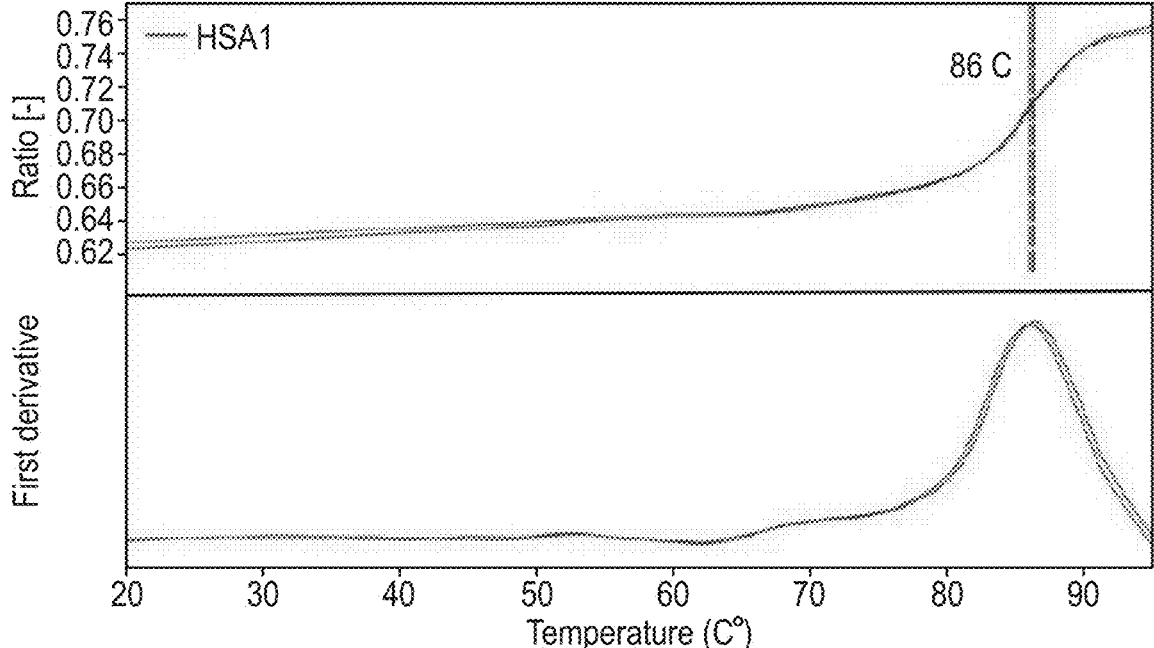

FIG. 5 shows nanoDSF of HSA1 variant.

Figure 6:
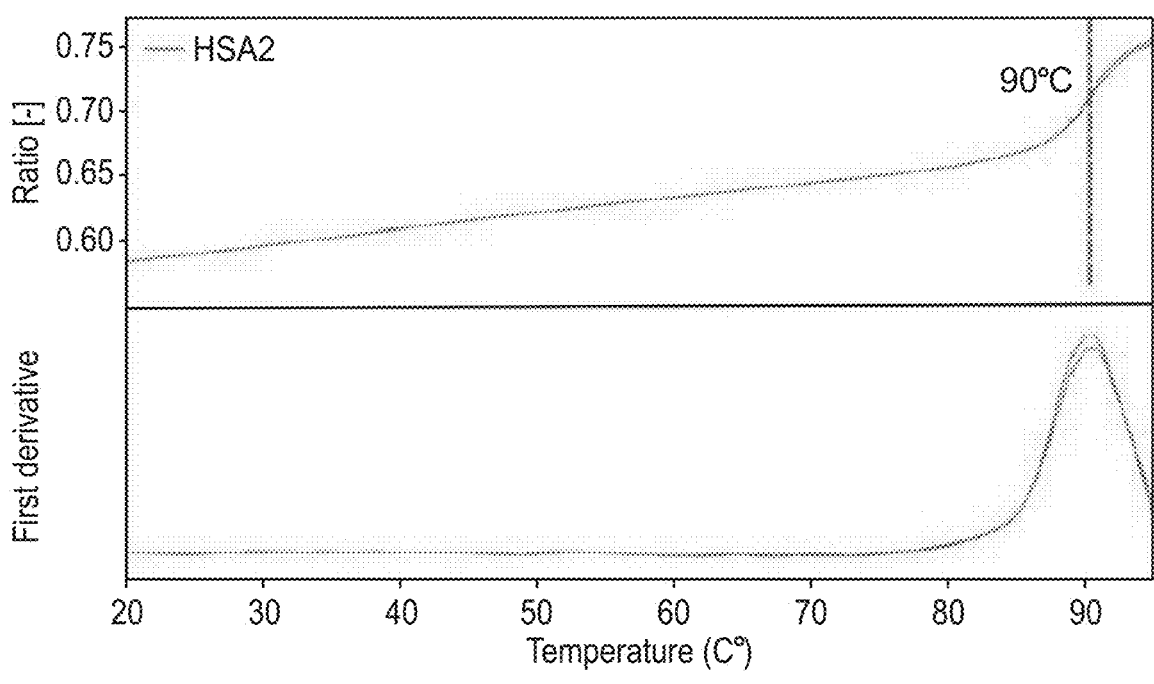

FIG. 6 shows nanoDSF of HSA2 variant.

Figure 7:
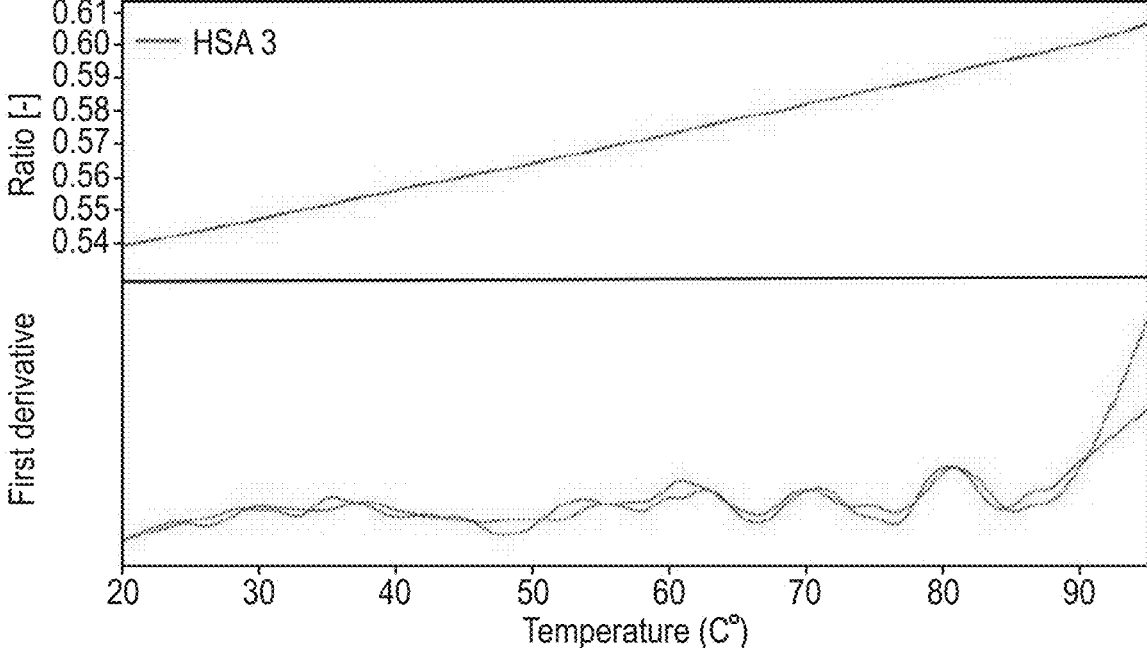

FIG. 7 shows nanoDSF of HSA3 variant.

Figure 8:
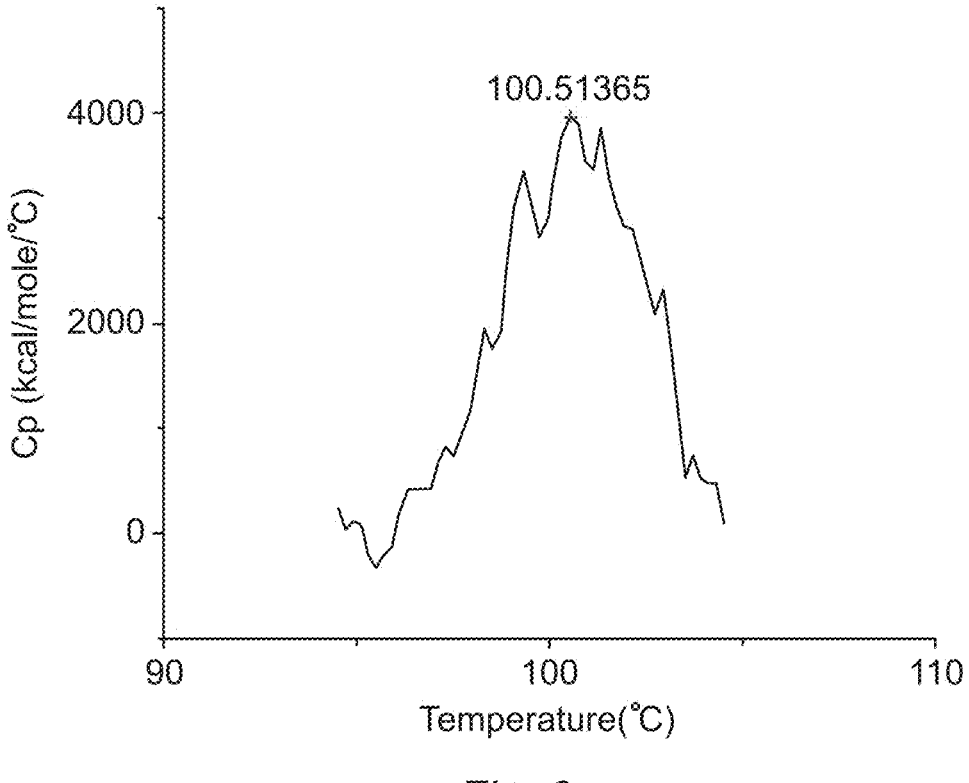

FIG. 8 shows DSC of HSA3 variant.

Figure 9:
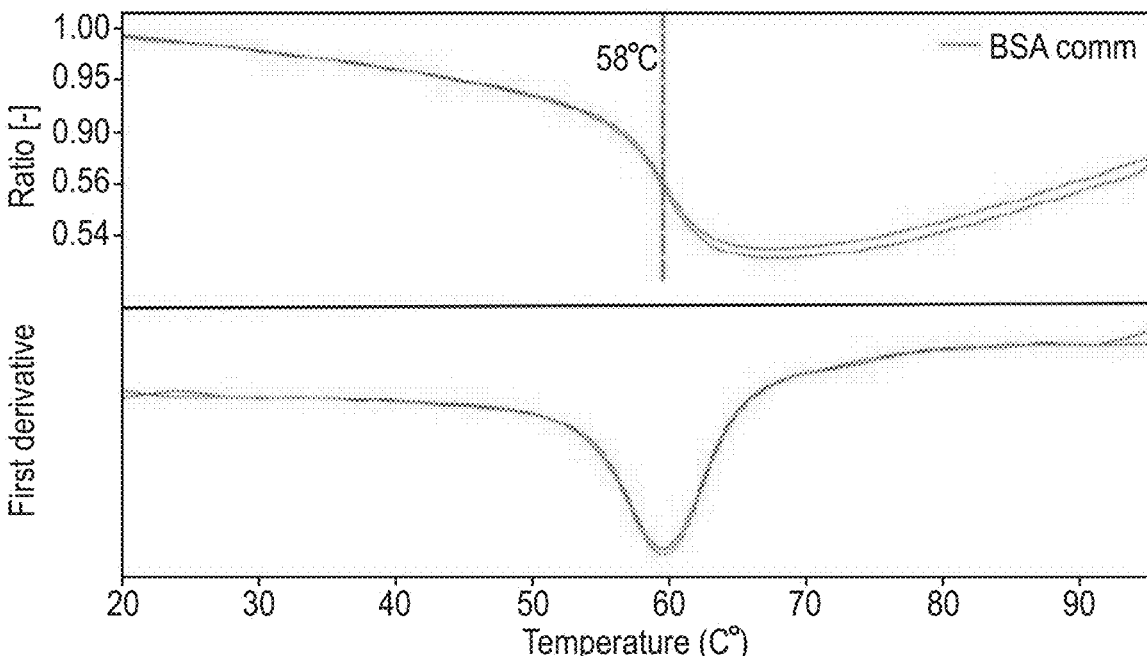

FIG. 9 shows nanoDSF of BSA WT variant.

Figure 10:
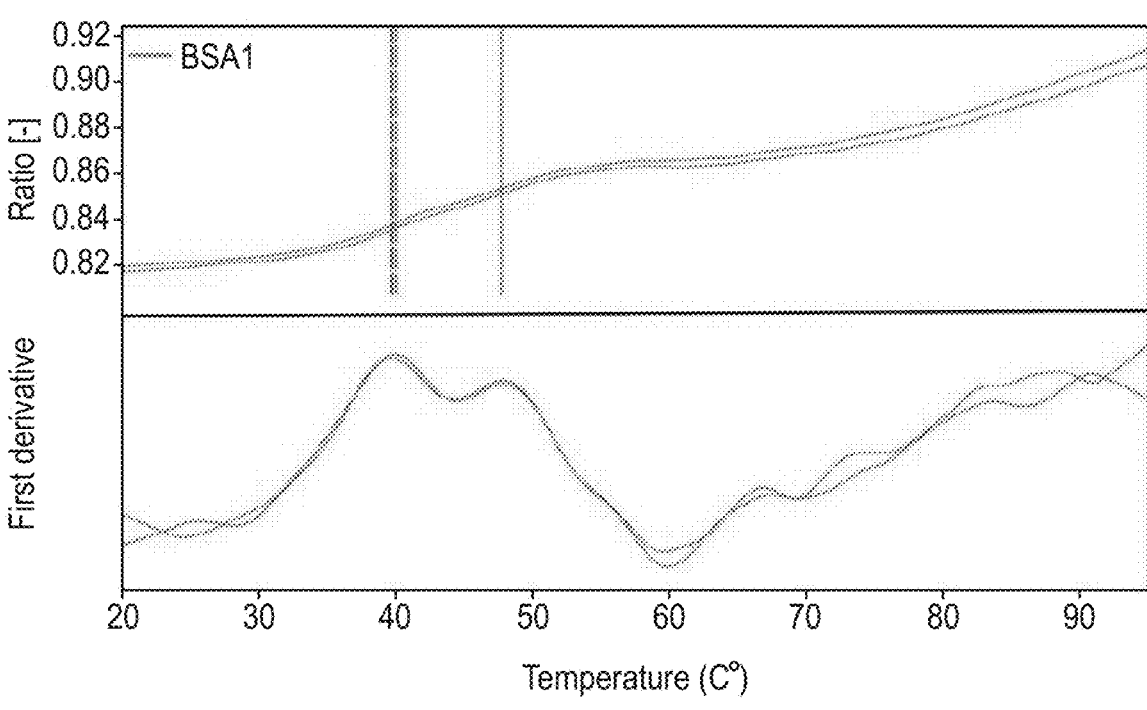

FIG. 10 shows nanoDSF of BSA1 variant.

Figure 11:
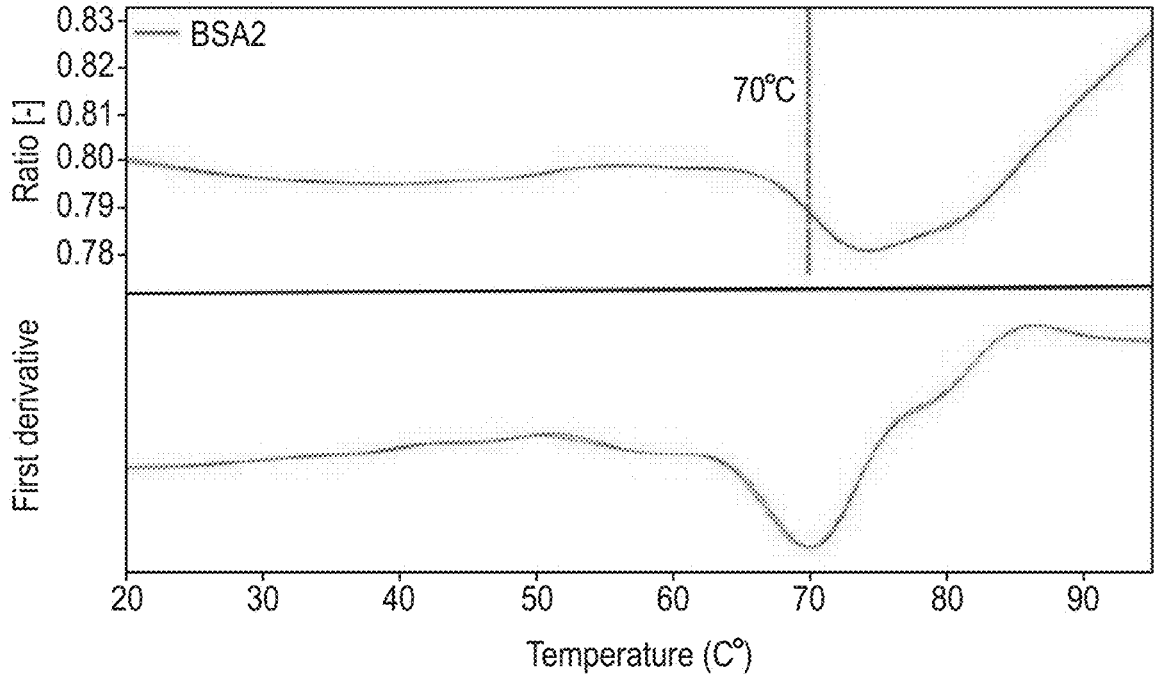

FIG. 11 shows nanoDSF of BSA2 variant.

Figure 12:
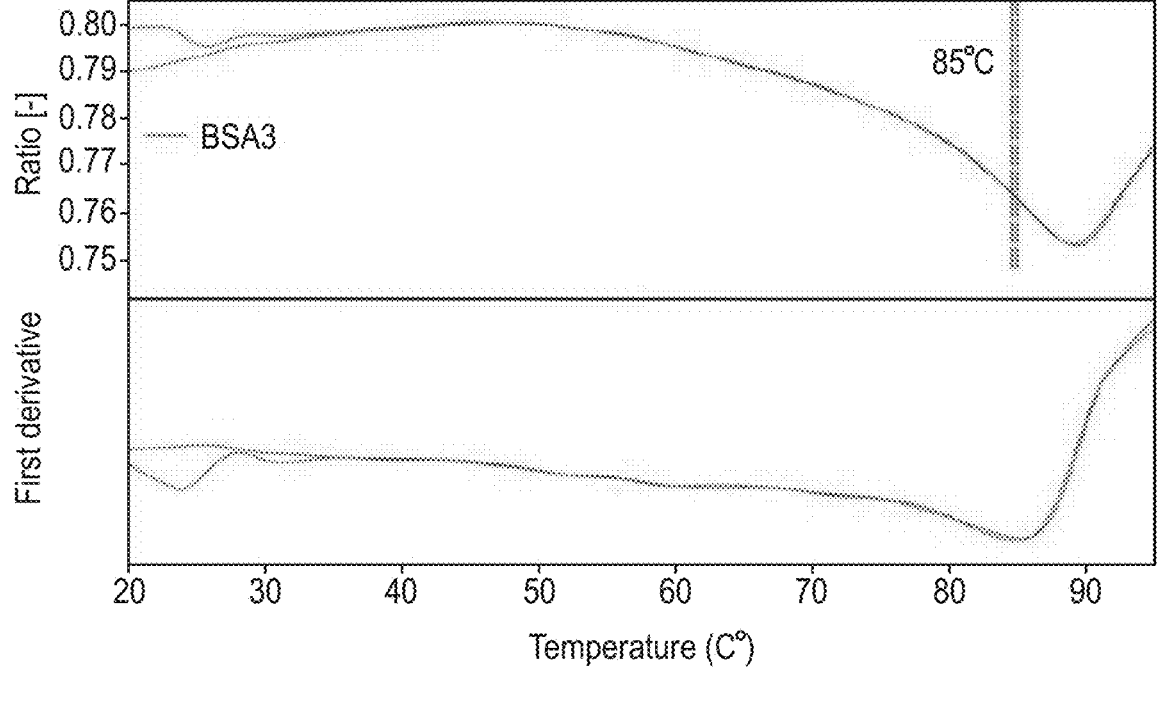

FIG. 12 shows nanoDSF of BSA3 variant.

Figure 13:
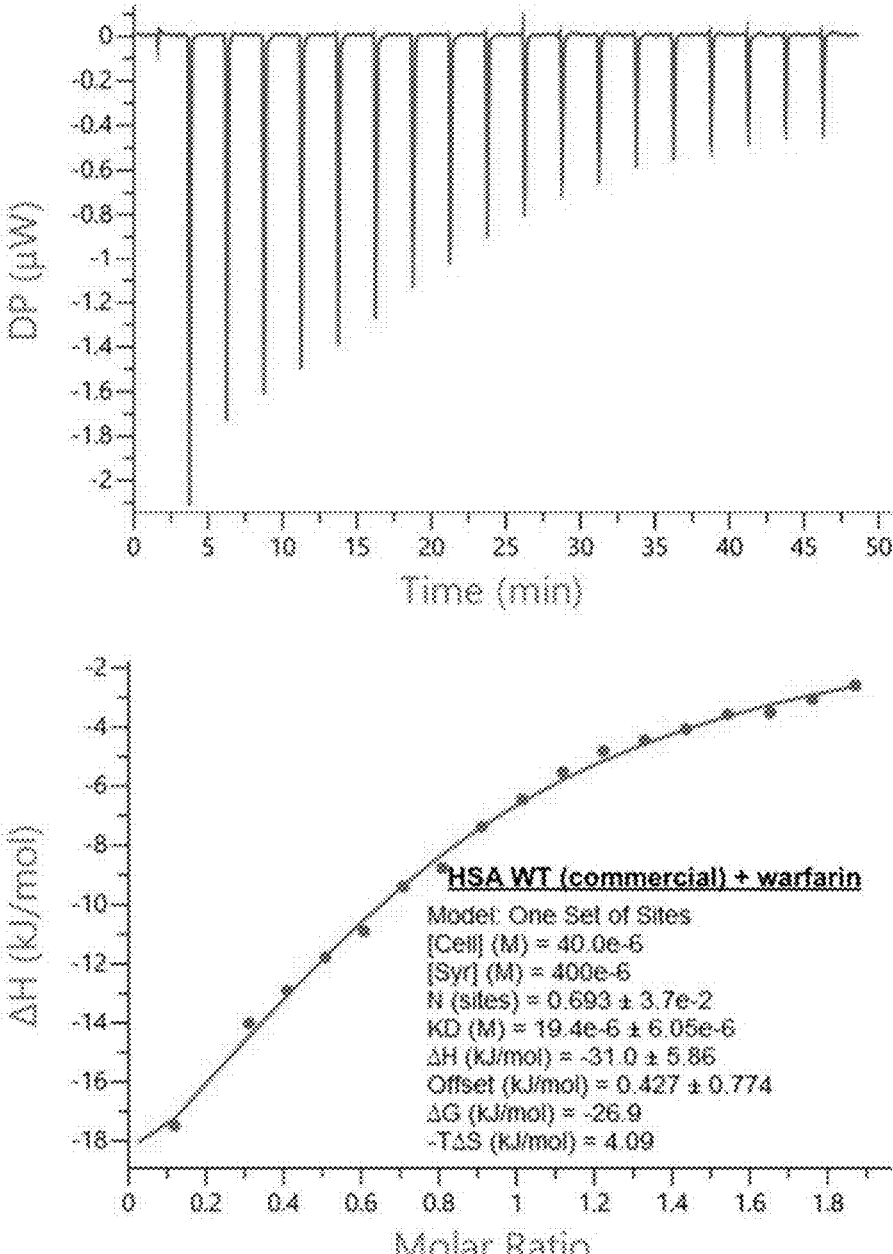

FIG. 13 shows binding of warfarin by HSA WT (commercial) as measured by ITC.

Figure 14:
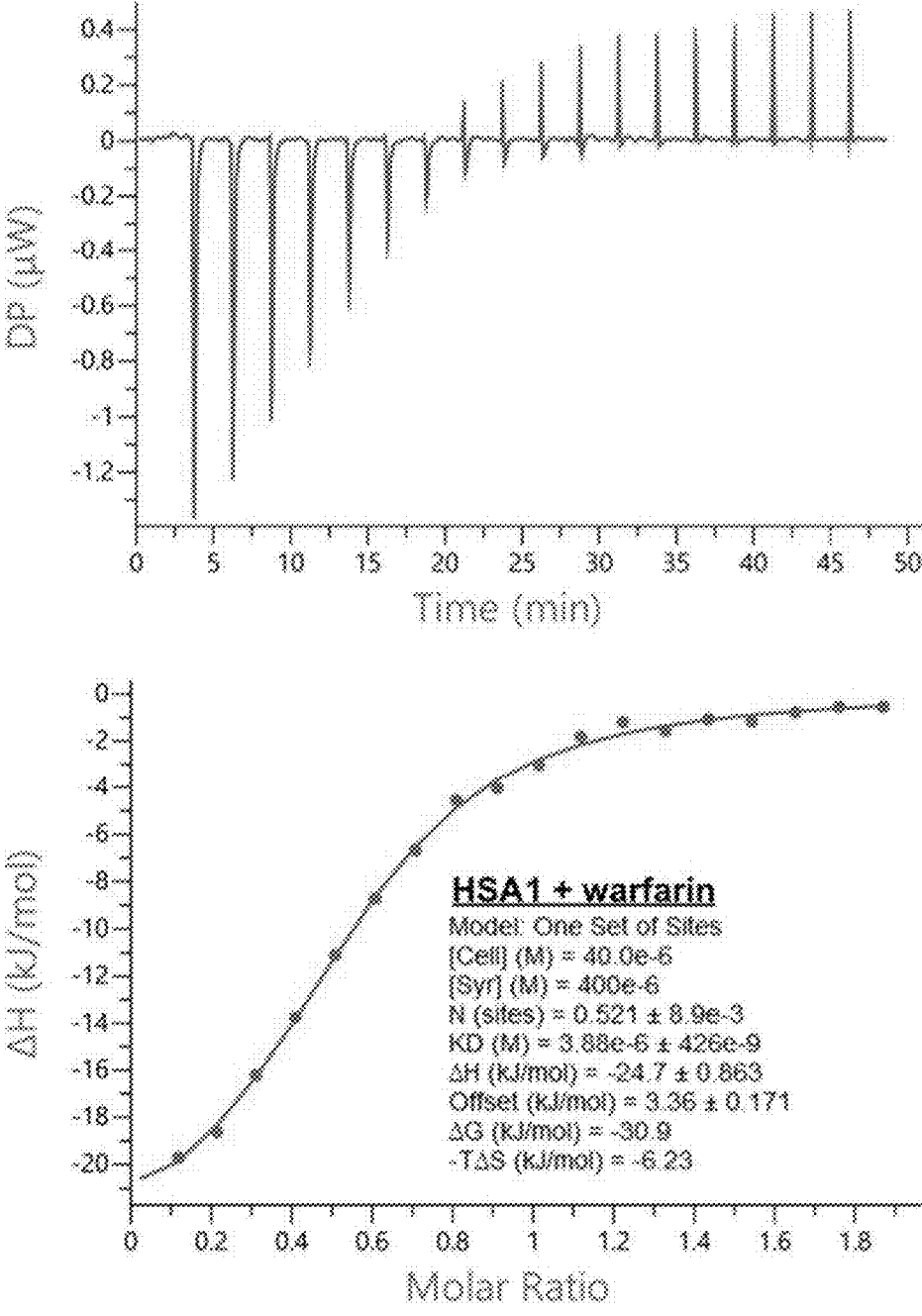

FIG. 14 shows binding of warfarin by HSA1 as measured by ITC.

Figure 15:
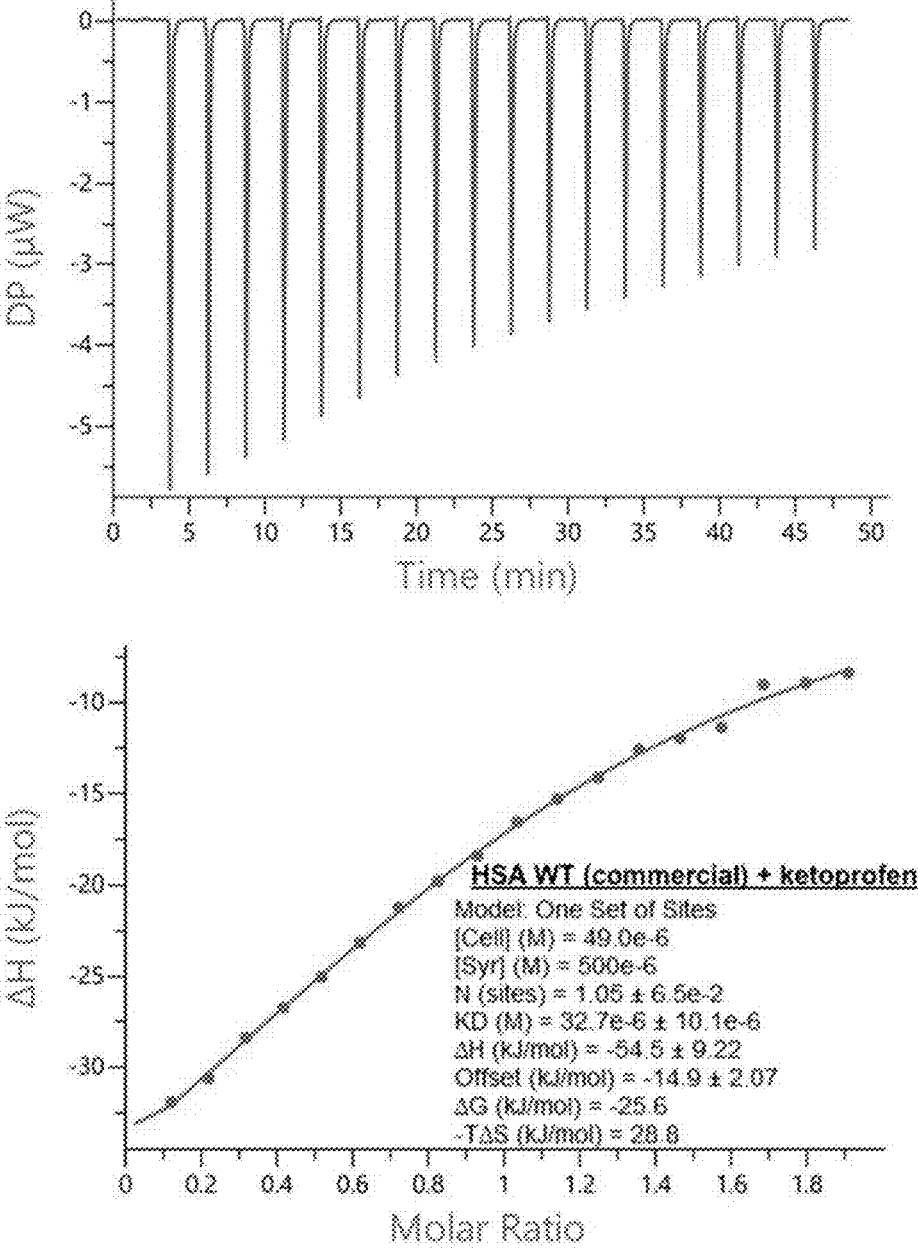

FIG. 15 shows binding of Ketoptofen by HSA WT (commercial) as measured by ITC.

Figure 16:
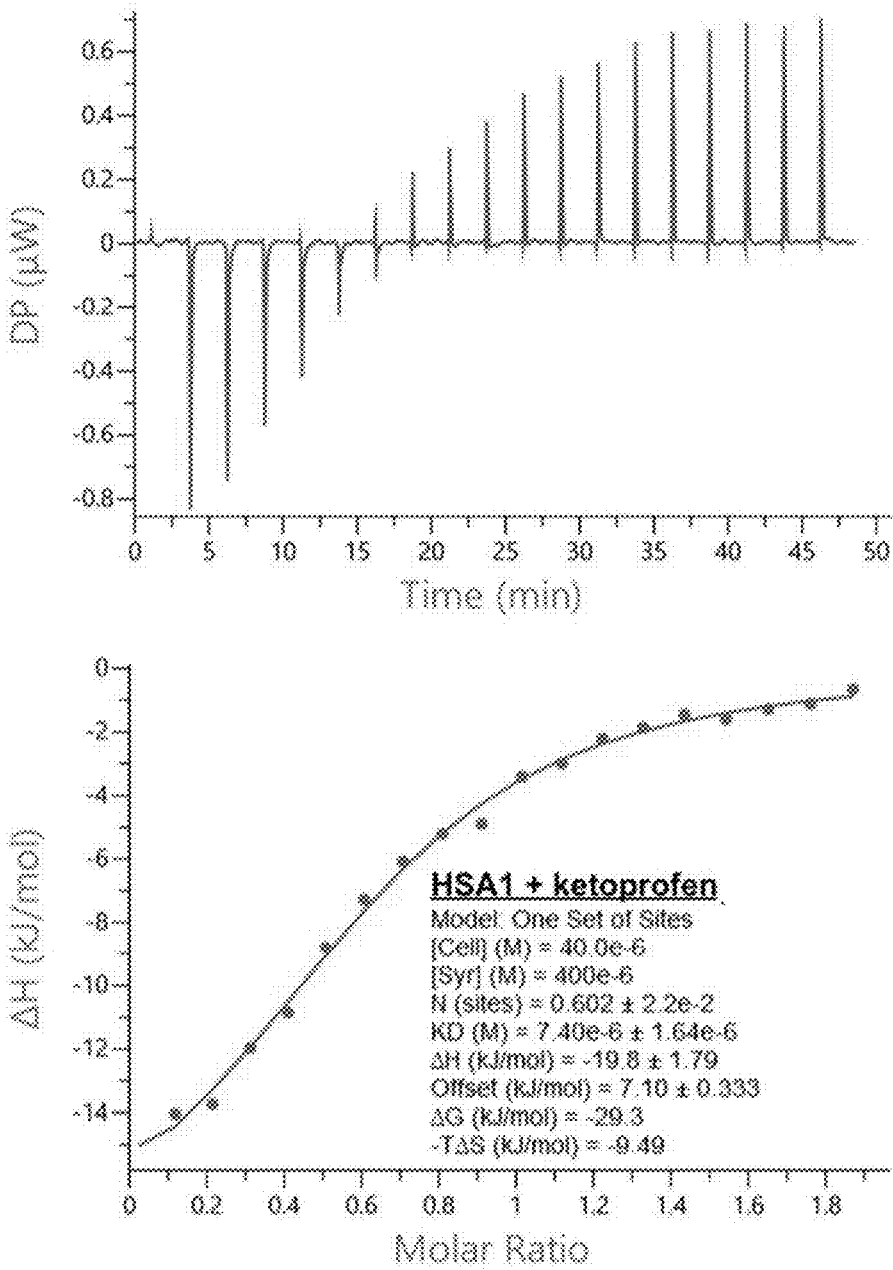

FIG. 16 shows binding of Ketoptofen by HSA1 as measured by ITC.

Figure 17:
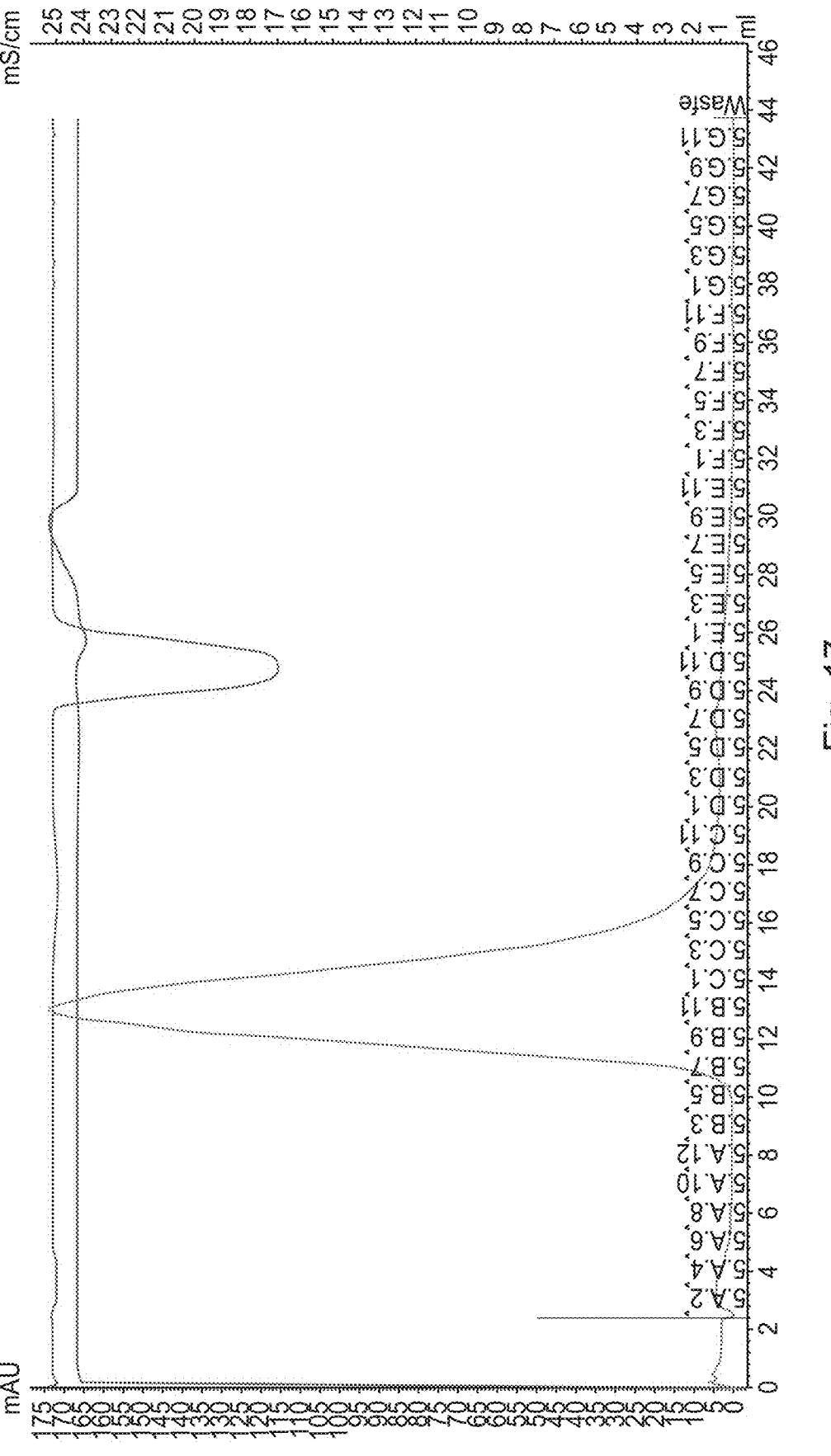

FIG. 17 shows a gel filtration chromatogram of His-tagged HSA1 variant.

Figure 18:
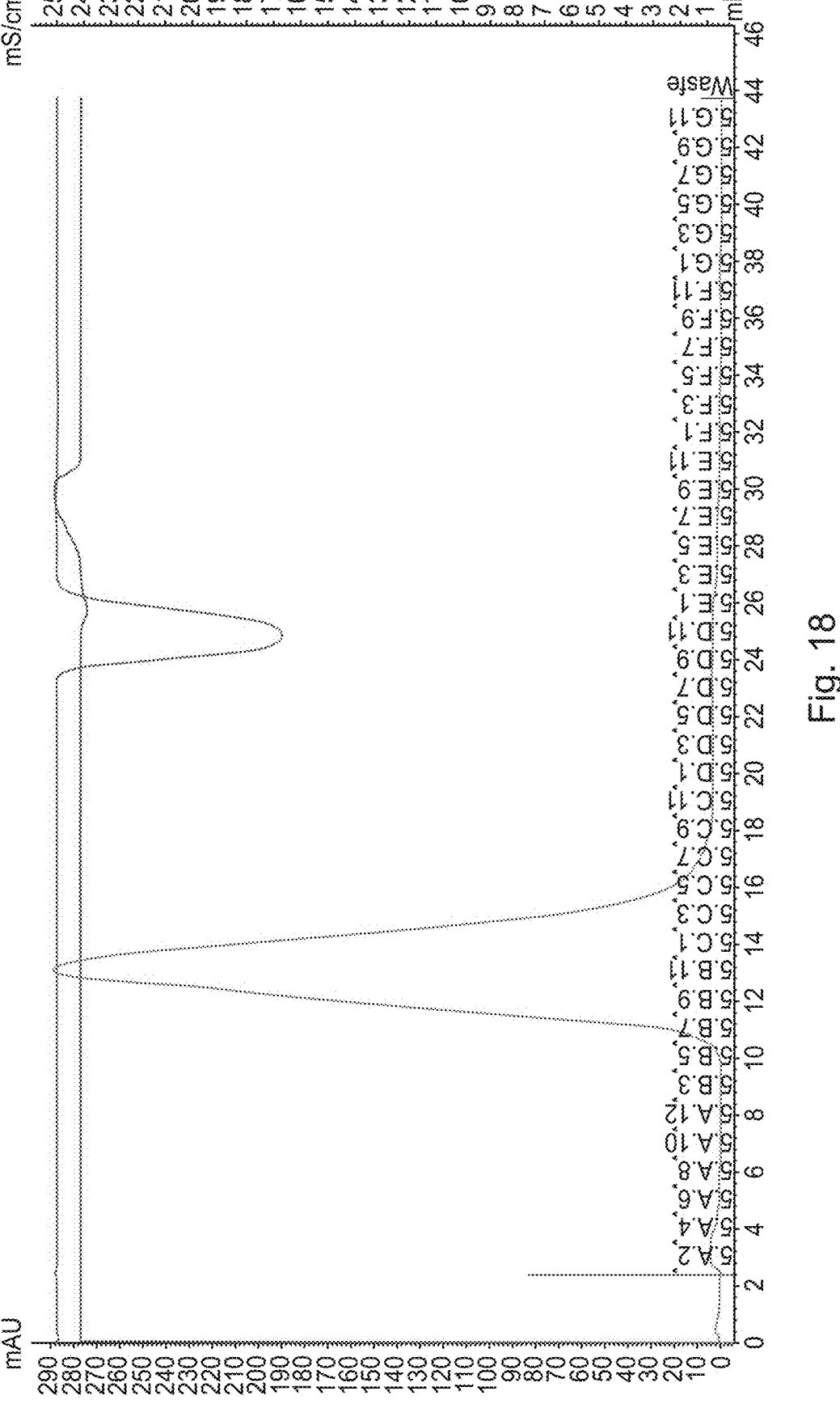

FIG. 18 shows a gel filtration chromatogram of His-tagged HSA2 variant.

Figure 19:
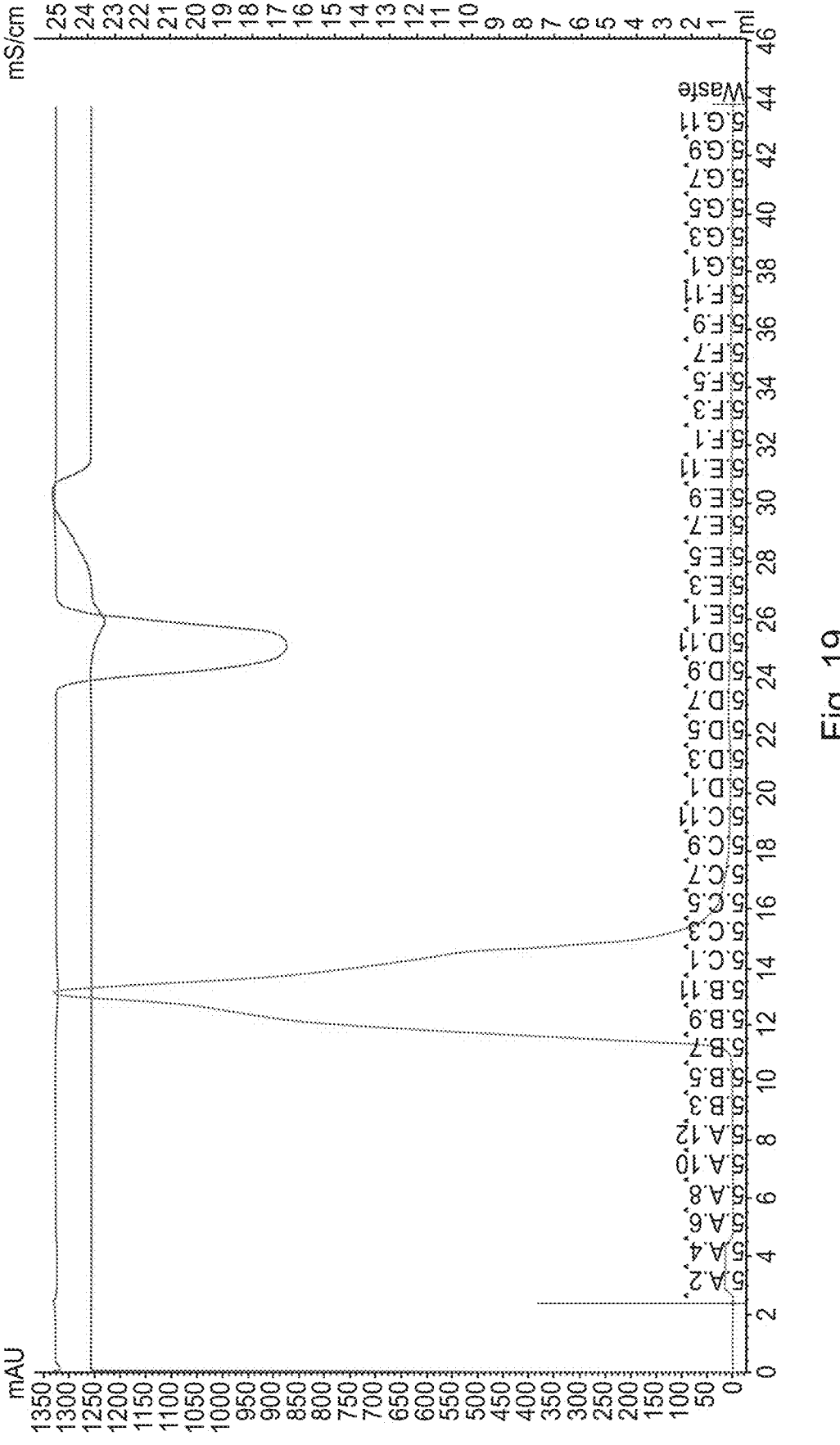

FIG. 19 shows a gel filtration chromatogram of His-tagged HSA3 variant.

Figure 20:
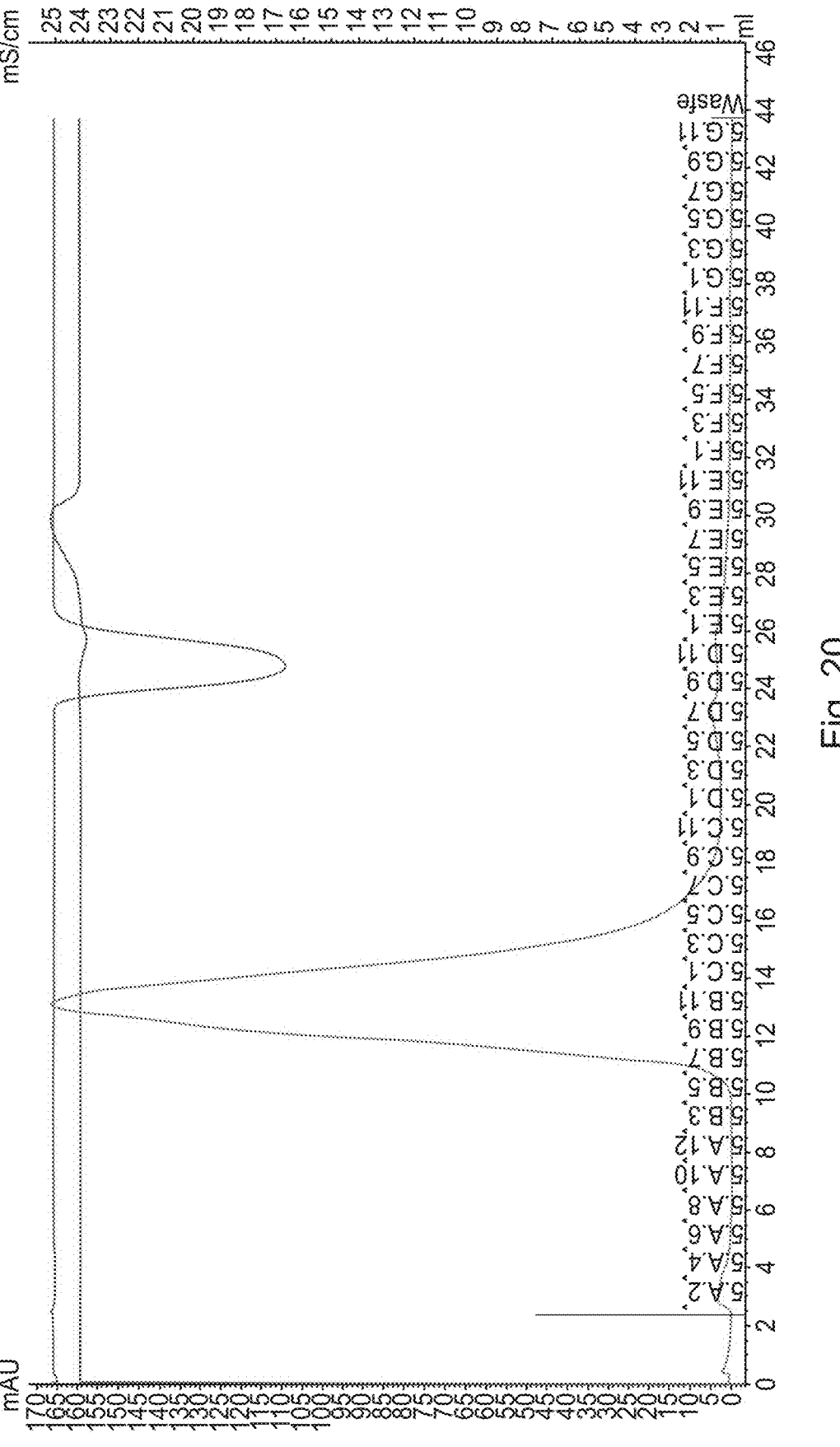

FIG. 20 shows a gel filtration chromatogram of His-tagged BSA1 variant.

Figure 21:
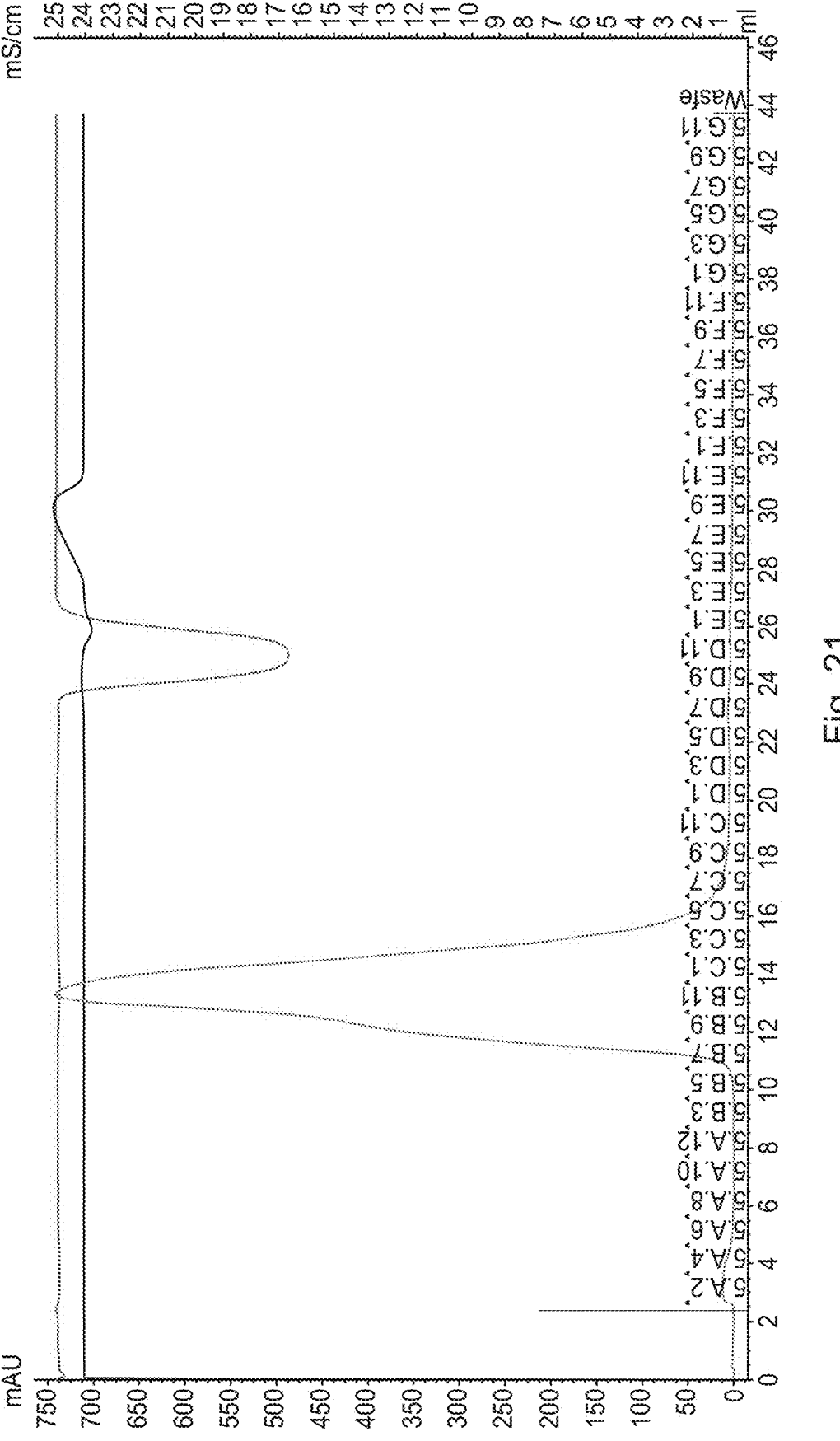

FIG. 21 shows a gel filtration chromatogram of His-tagged BSA2 variant.

Figure 22:
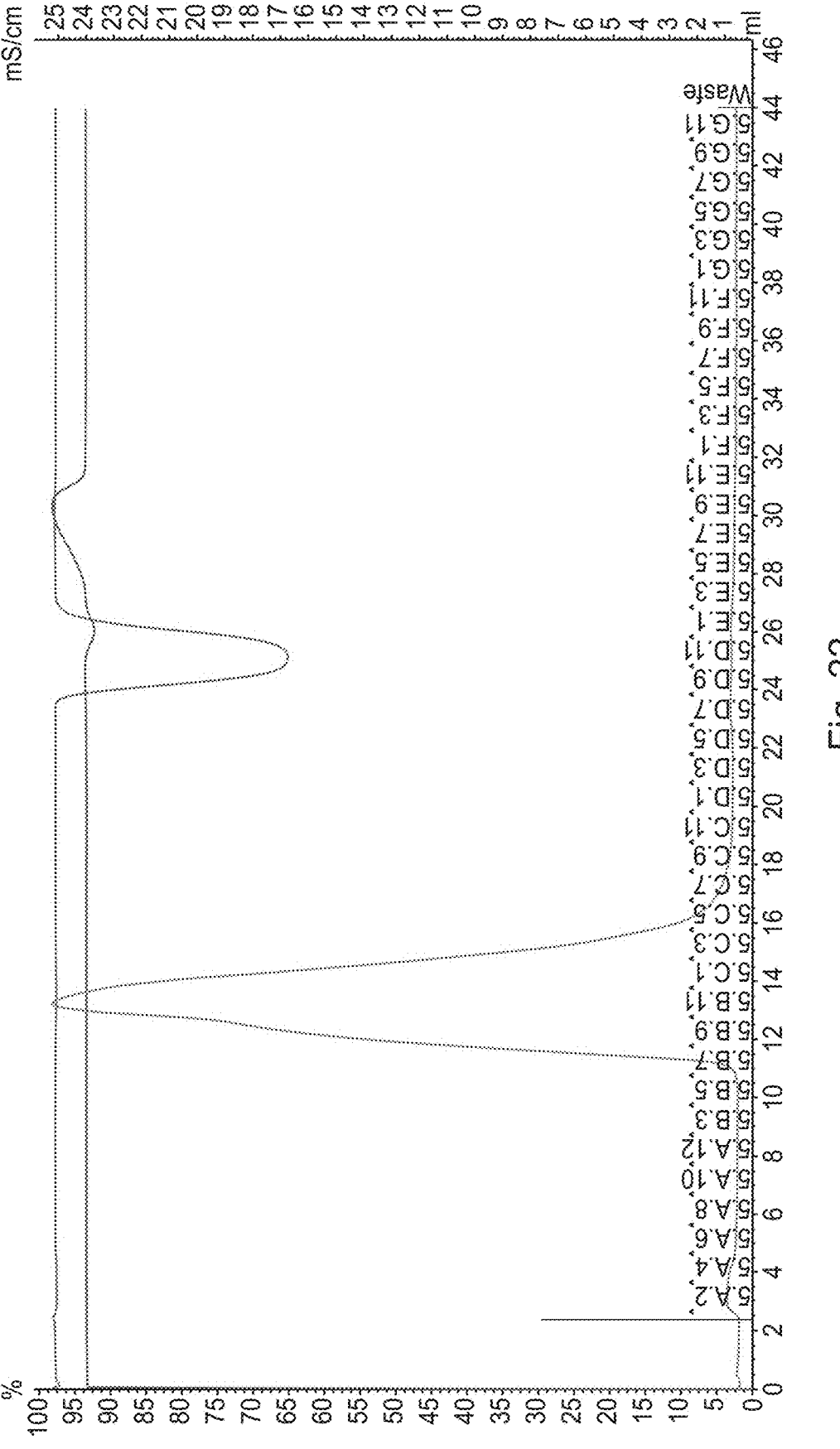

FIG. 22 shows a gel filtration chromatogram of His-tagged BSA3 variant.

Figure 23:
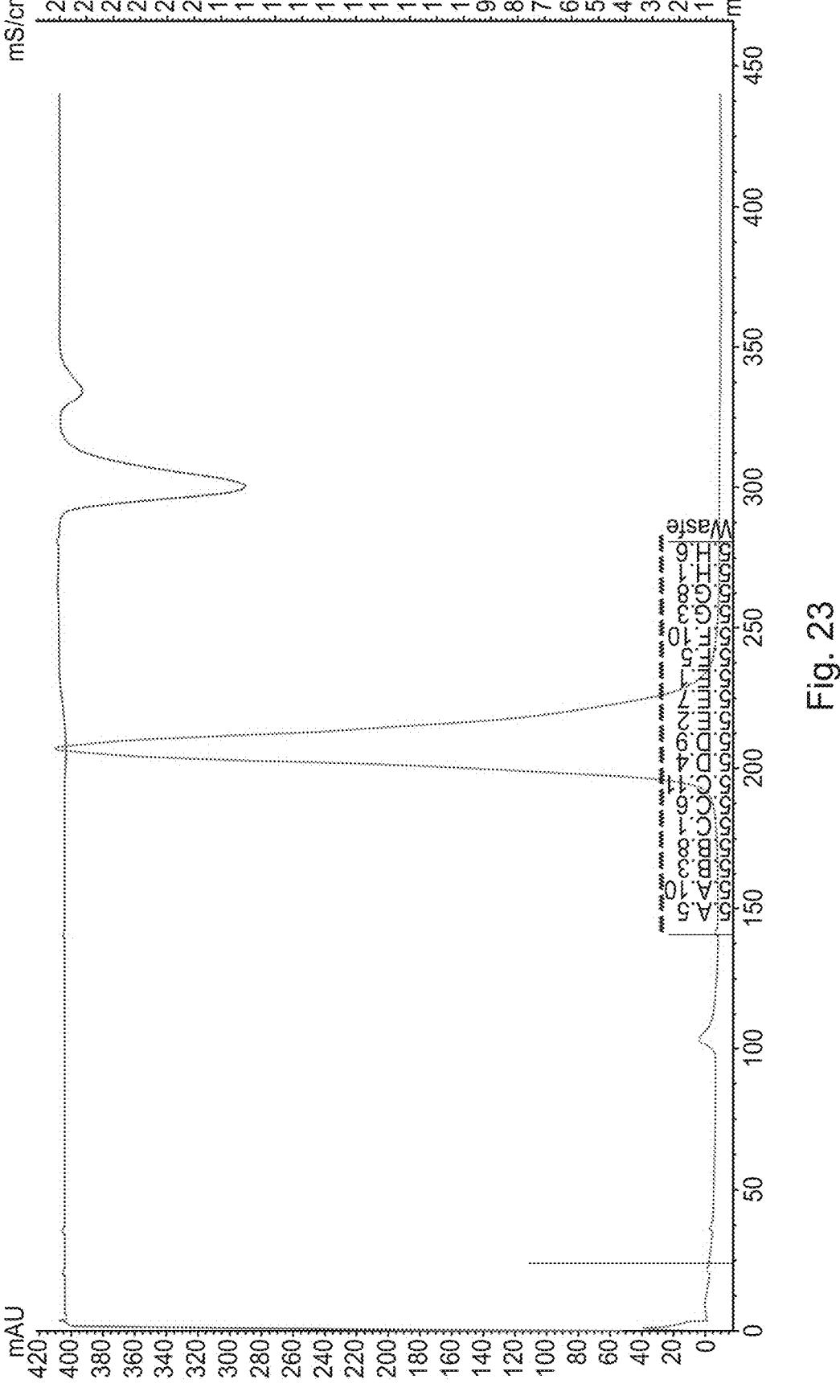

FIG. 23 shows a gel filtration chromatogram of HSA1-SUMO variant following cleavage of bdSUMO tag.

Figure 24:
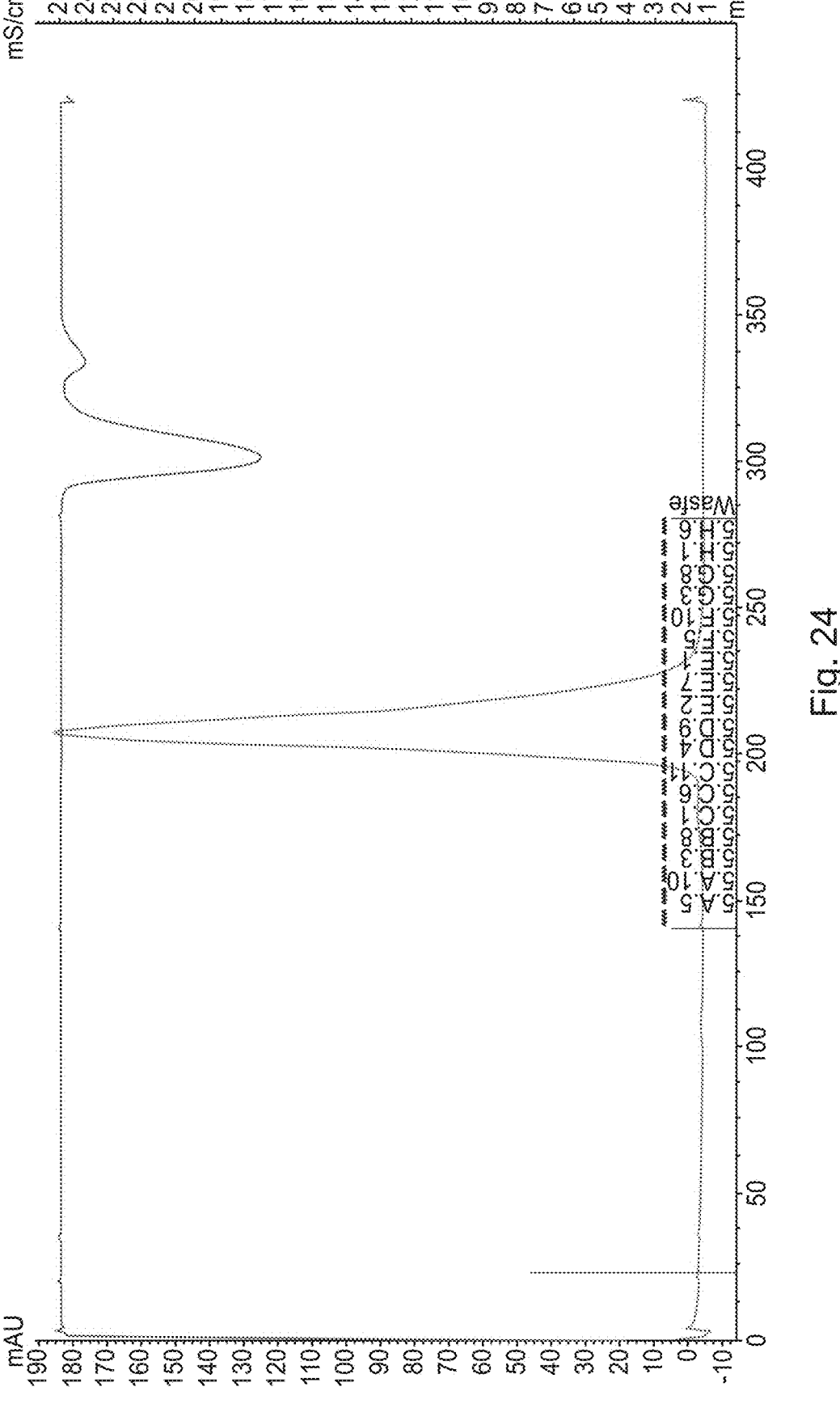

FIG. 24 shows a gel filtration chromatogram of BSA2-SUMO variant following cleavage of bdSUMO tag. Preparations with equal amounts of monomeric and dimeric fractions of BSA2.

Figure 25:
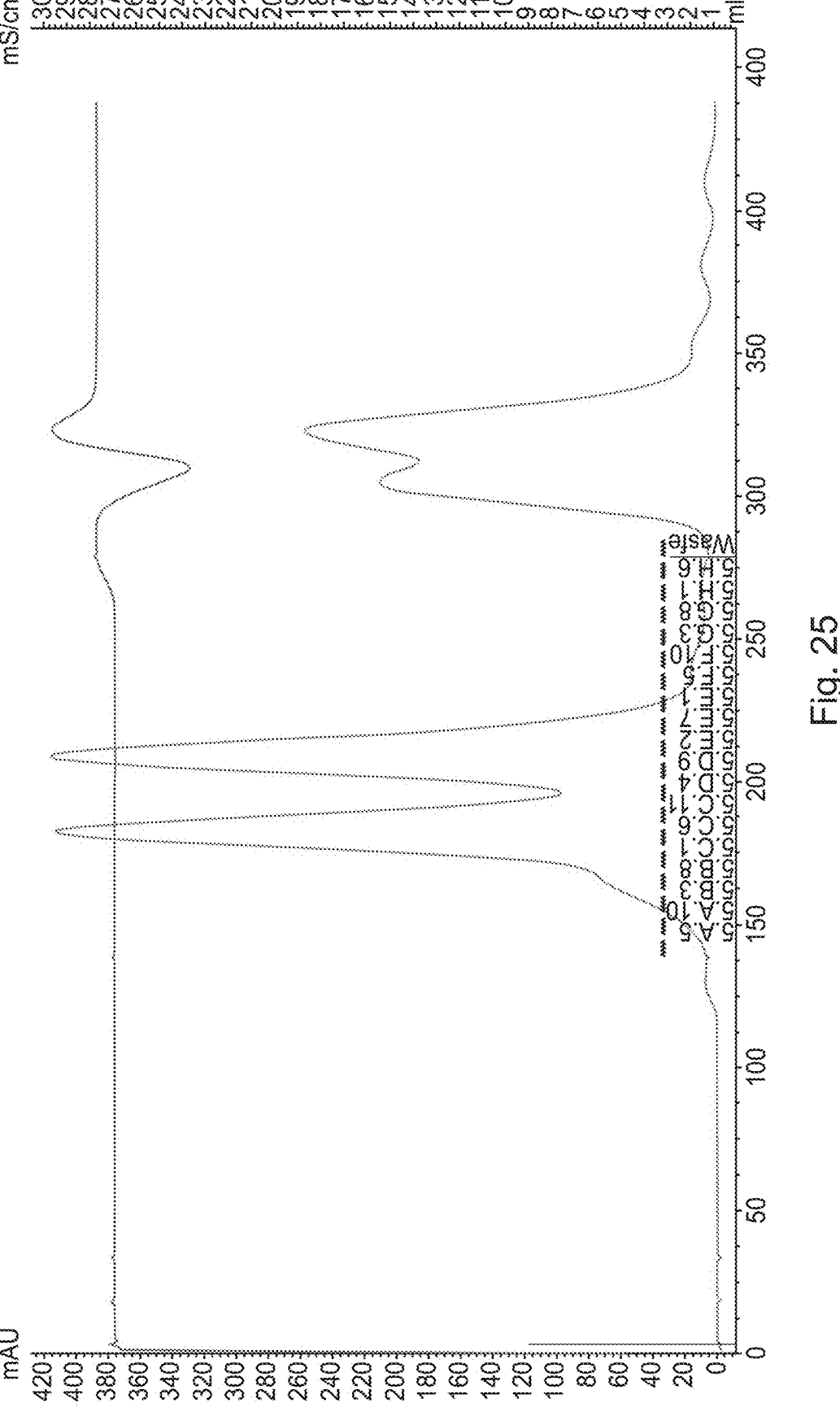

FIG. 25 shows a gel filtration chromatogram of BSA2-SUMO variant following cleavage of bdSUMO tag. Preparations with equal amounts of monomeric and dimeric fractions of BSA2 (as in FIG. 24).

Figure 26:
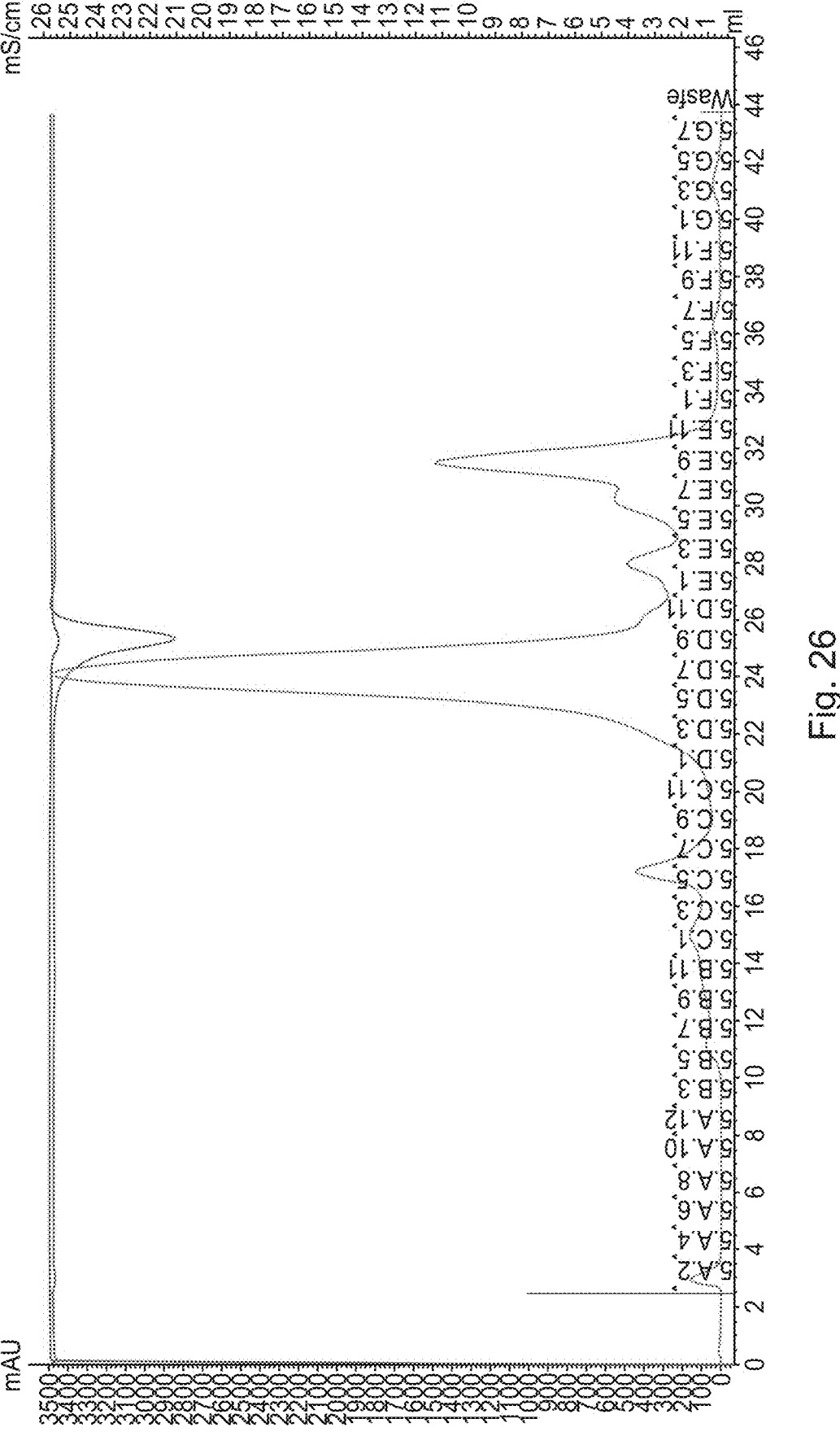

FIG. 26 shows a gel filtration chromatogram of tagless HSA1 variant.

FIGS. 27A-D shows the non-toxicity and function of albumin designs according to some embodiments of the invention in cell culture medium. HEK293T cells (A) and viability (B) with 1 mr/ml of albumin designs (or wild type) in medium with 5% FBS. Live hybridoma cells number (C) and produced antibody titers (D) with 1 mg/ml albumin designs (or wild type) in medium with 1% horse serum.

Figure 28A:
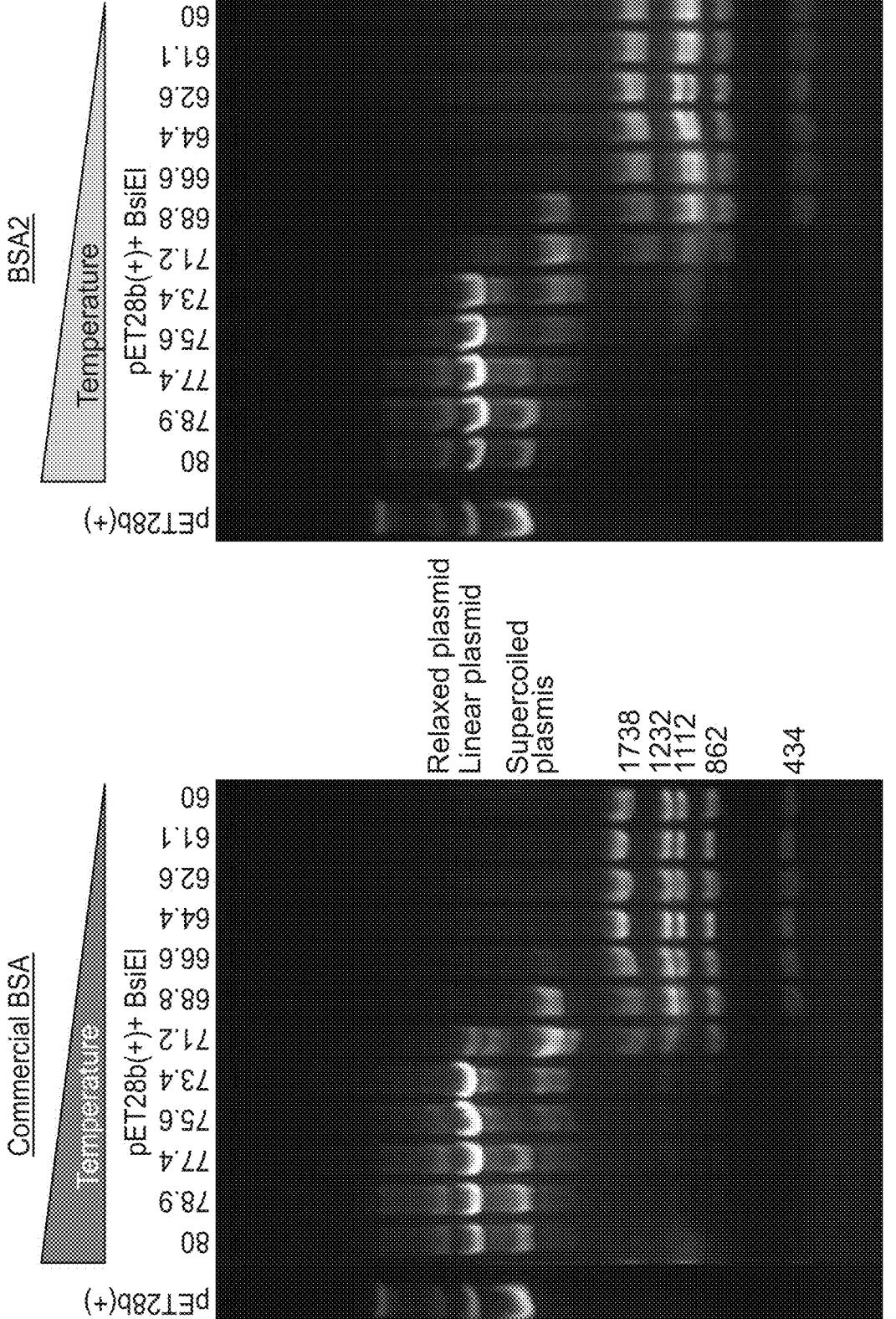
Figure 28B:
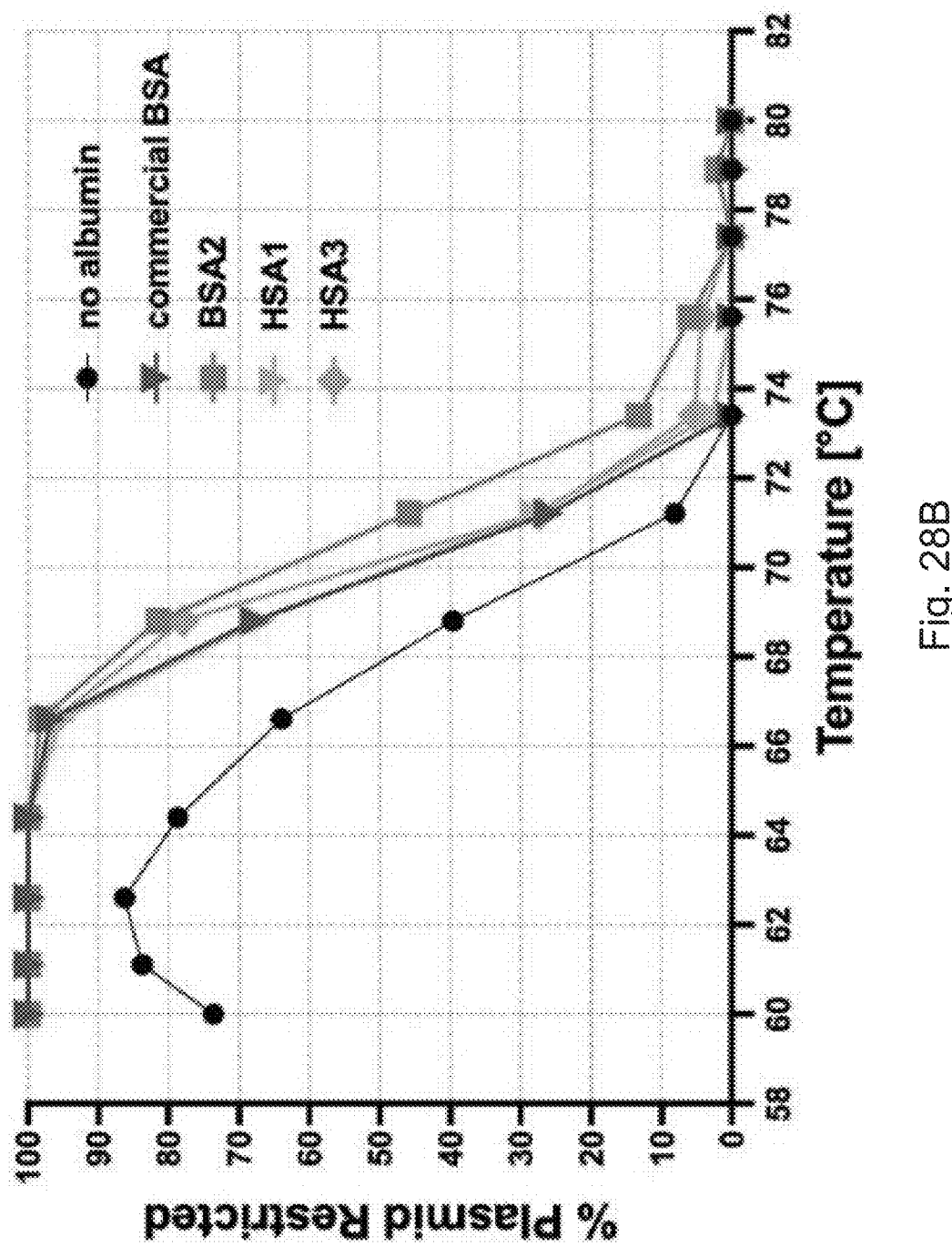

FIGS. 28A-B shows DNA restriction experiments in the presence of the albumin designs according to some embodiments of the invention. (A) Restriction of plasmid pET28b (+) with BsiEI at different temperatures in a buffer containing commercial BSA (left) or stabilized BSA2 (right). (B) % of restricted plasmid as a function of temperature in buffer containing various albumin variants.

DESCRIPTION OF SPECIFIC EMBODIMENTS OF THE INVENTION

The present invention, in some embodiments thereof, relates to albumin protein variants, production thereof and uses of same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Serum albumin is the most abundant protein in the blood serum of mammals and has essential carrier and physiological roles. Albumins are also used in research, in a wide variety of molecular and cellular experiments. Despite their importance, however, albumins are challenging for heterologous, i.e., recombinant, expression in microbial hosts. Therefore, albumins used in research and biotechnological applications are primarily derived from animal serum despite severe ethical and reproducibility concerns.

In order to overcome technological hurdles associated with recombinant production of albumin, and whilst conceiving and reducing embodiments of the invention to practice, the present inventors designed and synthesized several stable versions of human and bovine serum albumins. The most highly mutated version of human albumin, which is termed herein "Thermalbumin" (HSA3), is stable beyond the boiling point and, unusually for a large and complex protein, exhibits reversible temperature-dependent folding and unfolding. Design accuracy is verified by crystallographic analysis of a human albumin variant with 16 mutations (i.e., HSA1). This albumin variant exhibits fatty-acid binding properties indistinguishable from the wild type. The stable albumin designs may be used in making reliable, animal-free reagents for molecular and cell biology and enables mutagenesis, including in high-throughput format, to study and enhance albumin physiological properties.

As used herein "albumin" refers to serum albumin having the symbol "Serum_albumin". In human, the albumin is referred to herein as SEQ ID NO:1. In bovine it is referred to herein as SEQ ID NO: 9.

As used herein "protein" is interchangeably used with "polypeptide".

According to teachings of the invention, alterations are made to the wild-type sequence to produce the albumin variants having at least a same function (e.g., protein/drug binding) as the wild type protein.

The term "variant", in the structural sense, means a polypeptide derived from a wild type albumin comprising an alteration, i.e., a substitution, insertion, and/or deletion, at one or more (several) positions.

A substitution means a replacement of an amino acid occupying a position with a different amino acid; a deletion means removal of an amino acid occupying a position; and an insertion means adding 1-3 amino acids adjacent to an amino acid occupying a position. The altered polypeptide (variant) can be obtained through human intervention by modification of the polynucleotide sequence encoding the wild type protein.

According to a specific embodiment, the alteration is a substitution.

According to a specific embodiment, the alteration comprises a plurality of substitutions e.g., 16-100 amino acid coordinates, e.g., 10-80, 16-75, 16-73, 16-70, 16-65, 16-60, 16-55, 16-50, 16-45, 16-40, 16-35, 16-30, 16-25, 16-20.

As used herein "soluble" or "solubility" refers to accumulation of the protein variant as individual molecules (monomers or dimers) in the cytosol of the bacterial cells or upon secretion and not as aggregates such as in the case of inclusion bodies. Solunility is typically tested by Coomassie staining.

As used herein "thermostability" refers to preservation of the wild type structure and chemical properties of albumin under extreme temperatures e.g., 60° C., 70° C., 75, 80° C., 85° C., 90° C. or even 95° C. or above, as determined by the melting temperature. Thermostability is determined using methods which are well known in the art and include but are not limited to nanoscale differential scanning fluorimetry (nanoDSF) or differential scanning calorimetry (DCS).

According to an aspect of the invention there is provided an albumin protein variant (HSA variant) comprising:

(i) an amino acid sequence at least 85% identical to SEQ ID NO: 1;

(ii) mutations set forth in H39L, L42M, V120P, F156Y, D187E, L198H, S202I, V310I, A371S, V381I, V409I, S427A, V455I, K519E, A552S and V576I, where the coordinates correspond to the SEQ ID NO: 1; and wherein the albumin protein is soluble when expressed in bacteria and characterized by increased thermostability as compared to wild type human serum albumin (HSA) of SEQ ID NO: 1.

According to another aspect, there is provided an albumin protein variant (BSA variant) comprising:

(i) an amino acid sequence at least 85% identical to SEQ ID NO: 9;

(ii) mutations set forth in G21A, S28A, H39L, L42M, L138I, V163I, G174A, M184I, I202L, V230I, A309L, V380I, V408I, S426T, T518E and V575I, where the coordinates correspond to said SEQ ID NO: 9; and wherein the albumin protein is soluble when expressed in bacteria and characterized by increased thermostability as compared to wild type bovine serum albumin (BSA) of SEQ ID NO: 9.

Thus, the protein variant (HSA) comprises an amino acid sequence which is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO:1, as determined using the BestFit software of the Wisconsin sequence analysis package, utilizing the Smith and Waterman algorithm, where gap weight equals 50, length weight equals 3, average match equals 10 and average mismatch equals −9.

According to another embodiment, the protein variant comprises an amino acid sequence which is at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO:1, as determined using the BestFit software of the Wisconsin sequence analysis package, utilizing the Smith and Waterman algorithm, where gap weight equals 50, length weight equals 3, average match equals 10 and average mismatch equals −9. Of note, the percentage of homology refers to global homology over the albumin protein sequence.

According to a specific embodiment, the protein is at least 95% identical to SEQ ID NO: 1.

According to a specific embodiment, the protein is at least 99% identical to SEQ ID NO: 1.

According to a specific embodiment, the protein comprises the amino acid sequence set forth in SEQ ID NO: 3, 5 or 7.

According to alternative embodiments, the protein variant (BSA) comprises an amino acid sequence which is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO: 9, as determined using the BestFit software of the Wisconsin sequence analysis package, utilizing the Smith and Waterman algorithm, where gap weight equals 50, length weight equals 3, average match equals 10 and average mismatch equals −9.

According to another embodiment, the protein variant (BSA) comprises an amino acid sequence which is at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO: 9, as determined using the BestFit software of the Wisconsin sequence analysis package, utilizing the Smith and Waterman algorithm, where gap weight equals 50, length weight equals 3, average match equals 10 and average mismatch equals −9. Of note, the percentage of homology refers to global homology over the albumin protein sequence.

According to a specific embodiment, the protein is at least 95% identical to SEQ ID NO: 9.

According to a specific embodiment, the protein is at least 99% identical to SEQ ID NO: 9.

According to a specific embodiment, the protein comprises the amino acid sequence set forth in SEQ ID NO: 11, 13 or 15.

The protein variant can also be referred to "as human serum albumin (HSA)", which when comprises all the 16 mutations (as in Tables 2, 3) is referred to herein as "HSA1", "HSA2", "HSA3" or "BSA1", "BSA2", "BSA3". These mutations are only located in the protein core and not on the surface or binding sites of albumin as elaborated hereinbelow and in the Examples section which follows.

The extraordinary ligand binding properties of serum albumin reflect its multidomain organization. The complex mechanism modulating ligand binding to serum albumin represents one of the most important structure-function correlations ever reported for monomeric proteins. Serum albumin is known to carry almost every small molecule, thus it functions as a molecular cargo/or nanovehicle for clinical, biophysical, and industrial purposes. Under physiological conditions, serum albumin binds not only endogenous and exogenous low molecular weight compounds but also peptides and proteins. Thirty-five proteins were found to be associated to serum albumin including both known high and low abundant proteins (e.g., angiotensinogen, apolipoproteins, ceruloplasmin, clusterin, hemoglobin (Hb), plasminogen, prothrombin, and transferrin). Any binding of proteins and peptides to serum albumin impacts proteomics and biomarker discovery studies, since the presence of both unbound and bound states of proteins in serum can affect both the clearance and the detection of the free-state proteins and peptides. The fraction of peptides and proteins bound to serum albumin is defined as "albuminome" (reviewed in Fanali et al./Molecular Aspects of Medicine 33 (2012) 209-290).

Serum albumin is able to bind up to nine equivalents of long chain FAs, which represent the primary physiological ligands at multiple binding sites (i.e., FA1-FA9). These sites are distributed throughout the protein in an asymmetric way and show different affinity. FA4 and FA5 are high-affinity sites for FAs. FA2, a medium affinity site which lies at the interface between subdomains IA and IIA, is entirely contained within the N-terminal half of the protein, while sites FA4 and FA5 are entirely contained within domain III. These sites provide the most enclosed binding environments on SERUM ALBUMIN that allow the methylene tail of the FA to bind in a nearly linear conformation while the FA carboxyl forms specific salt-bridge interaction(s) with at least one basic amino acid side-chain. FA8 and FA9 are usually considered as supplementary binding sites, as they show ligand occupancy only in the presence of short-chain FAs (i.e., FA8) or in the presence of saturating FA concentration (i.e., FA9). FA binding sites also provide accommodation of several endogenous and exogenous ligands, including a wide variety of drugs, displaying appreciable affinity for one or more binding sites of serum albumin. This issue is of great relevance as binding to albumin improves plasma solubility and half-life of drugs, but at the same time reduces their free active concentration.

Thus, as mentioned, according to a specific embodiment, the mutations are done such that they do not affect albumin binding property. These are at least the 16 mutations of HSA1 and possibly any one of HSA2, i.e., H39L, L42M, V120P, K136N, F156Y, D187E, L198H, S202I, V216I, A254M, V310I, V344T, A371S, V381I, V409I, S427A, H440L, A449I, V455I, S470N, K519E, A528F, V547I, A552S, V576I and the equivalents in BSA1 and BSA2, as further described hereinbelow and in the Examples section which follows.

According to a specific embodiment, the albumin protein (e.g., HSA or BSA) exhibits at least about the same binding affinity to fatty acids such as myristate, such as determined by a crystal structure that contains 4 myristate molecules. This means that the protein is folded as wild type HSA or BSA (e.g., as compared to commercial HSA in the Examples section which follows) as evidenced by the ability to bind myristate. Myristate typically employs binding domains FA1, FA2, FA3, FA4, FA5.

Binding affinity is typically defined by $K_D$ and determined by various methods which are well known in the art.

According to a specific embodiment, binding affinity of albumin to small molecule or proteins ligandis determined by isothermal titration calorimetry (ITC), especially for water soluble molecules.

Specific embodiments of the method are provided in the Examples section which follows.

According to a specific embodiment, the binding affinity of the protein variant is increased by at least 1.2 fold, 1.3 fold, 1.4 fold, 1.5, fold, 1.6 fold, 1.7 fold, 1.8 fold, 1.9 fold, 2 fold, 2.5 fold, 3 fold, 4 fold, 5 fold, 6 fold, 7 fold, 8 fold, 9 fold, 10 fold, 12 fold, 15 fold, 20 fold, as compared to wild type HSA or BSA and even more when compared to other forms of recombinantly produced albumins such as in yeast or plant systems (see e.g., Petitpas I. et al 2001, Journal of Biological Chemistry 276(35): 22804-22809).

According to a specific embodiment, the protein variant binds a small molecule albumin ligand in at least the same affinity as wild type HSA of SEQ ID NO: 1 or BSA of SEQ ID NO: 9.

According to a specific embodiment, the small molecule is warfarin which binds Sudlow's site I or Ketoptofen which binds Sudlow's site II. According to a specific embodiment, the protein is HSA1. According to a specific embodiment, the binding affinity to Sudlow's site I or II is unharmed and even improved compared to the wild type protein e.g., wild type HSA.

FA7 (Sudlow's site I)—The hydrophobic cavity of subdomain IIA hosts the seventh FA binding site (i.e., FA7 or Sudlow's site I). This site binds preferentially bulky heterocyclic anions, the prototypical ligand being warfarin. This site is smaller than the analogous binding cavity in subdomain IIIA (i.e., FA3-FA4 or Sudlow's site II). The FA carboxylate is stabilized by polar interaction(s) with the Arg257 residue, thus providing a bridge between FA2 and FA7 sites. Drugs (e.g., warfarin) cluster in the center of Sudlow's site I Different compounds occupy the apolar compartments of Sudlow's site I to different extents, e.g., warfarin occupies the right-hand and the front sub-chambers.

FA3-FA4 (Sudlow's site II) FA3 and FA4 are composed of six helices and are located in a large cavity in subdomain IIIA that as a whole constitutes Sudlow's site II (FIG. 3). This cleft is preferred by aromatic carboxylates with an extended conformation, the non-steroidal anti-inflammatory drug ibuprofen representing the prototypical ligand.

According to a specific embodiment, the protein variant supports cell growth in culture, as further described hereinbelow.

According to a specific embodiment, the protein further comprises at least one mutation at albumin binding sites.

For instance, at least one of the mutations in the binding site of HSA:

mutations in the binding sites: V216I (also in HSA2 and HSA3), L250M, A254M (also in HSA2 and HSA3), G328A, V344T (also in HSA2 and HSA3), P384T, K402Y, V415M, V426L, M446L, A449I (also in HSA2 and HSA3), A528F (also in HSA2 and HSA3).

For instance, at least one of the mutations in the binding site of BSA:

mutations in the binding sites (all of these are present BSA2 and BSA3): V240I, H241Y, A253M, A260V, V344L, V414M, V425I, M445L, P485H, A527F, V546I, V551T.

According to a specific embodiment, the at least one mutation (e.g., at least 2, 3, 4, 5, 6, 7, 8. 9, 10, 11, 12, 13, 14, 15, 16, 17, 18, 19, 20, 21, 22, 23, 24, e.g., 16-25, 16-30) is selected from the group of mutations consisting of those in Table 2, where the coordinates are those of SEQ ID NO: 1.

According to a specific embodiment, the at least one mutation (e.g., at least 2, 3, 4, 5, 6, 7, 8. 9, 10, 11, 12, 13, 14, 15, 16, 17, 18, 19, 20, 21, 22, 23, 24, e.g., 16-25, 16-30) is selected from the group of mutations consisting of those in Table 3, where the coordinates are those of SEQ ID NO: 9.

According to a specific embodiment, the at least one mutation (e.g., at least 2, 3, 4, 5, 6, 7, 8. 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 50, 61, 62, 63, 64, 65, 66, 67, 68, 69, 70, 71, 72, e.g., 16-80. 16-75, 16-73, 16-70, 16-50) selected from the group of mutations consisting of those in Table 2, where the coordinates are those of SEQ ID NO: 1.

According to a specific embodiment, the at least one mutation (e.g., at least 2, 3, 4, 5, 6, 7, 8. 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 50, 61, 62, 63, 64, 65, 66, 67, 68, 69, 70, 71, 72, e.g., 16-80. 16-75, 16-73, 16-70, 16-50) selected from the group of mutations consisting of those in Table 3, where the coordinates are those of SEQ ID NO: 9.

According to a specific embodiment, the protein variant exhibits increased yield when compared to the wild type protein when expressed in bacteria.

As used herein "increased yield" refers to at least 5 fold, 10 fold, 15 fold, 20 fold, 25 fold, 30 fold, 40 fold, 50 fold, 70 fold, 100 fold, 500 fold, 1000 fold higher expression of the variant than that of wild type HSA or BSA (as described below). Commercial WT HSA and BSA are available from Sigma-Aldrich A1653 and A7638, respectively, which were used as control in the Examples section which follows.

As mentioned, the protein variant is characterized by increased thermostability as compared to wild type HSA (SEQ ID NO: 1).

As mentioned the protein variant is characterized by increased thermostability as compared to wild type BSA (SEQ ID NO: 9).

As used herein "increased thermostability" is increased thermal stability by at least 10° C., 15° C., 20° C., 25° C., 30° C., 35° C., 40° C., or more higher than that of wild type HSA or BSA (such as with respect to the controls used in the Examples section which follows).

For instance, HSA1, HSA2 and HSA3 showed 26-40° C. higher thermal stability relative to the commercial WT HSA (FIGS. 4-8). BSA2 and BSA3 designs had $T_M$ values of 70 and 85° C. respectively, 12-27° C. higher $T_M$ values than the WT BSA (FIGS. 9-12).

The solubility, functionality, thermal stability and/or high yield render the albumin variants of some embodiments of the invention, as described herein, highly suitable for recombinant expression.

Thus, according to an aspect of the invention there is provided a method of producing albumin, the method comprising expressing in bacteria a nucleic acid sequence encoding the protein variant as described herein, thereby producing albumin.

Accordingly there is provided a polynucleotide comprising a nucleic acid sequence encoding the protein variant as described herein.

To express exogenous nucleic acid sequences in cells, a polynucleotide sequence encoding the protein variant is preferably ligated into a nucleic acid construct suitable for mammalian cell expression. Such a nucleic acid construct includes a promoter sequence for directing transcription of the polynucleotide sequence in the cell in a constitutive or inducible manner.

A variety of prokaryotic can be used as host-expression systems to express the protein variants of some embodiments of the invention. These include, but are not limited to, microorganisms, such as bacteria transformed with a recombinant bacteriophage DNA, plasmid DNA or cosmid DNA expression vector containing the coding sequence.

According to a specific embodiment, the cell is a bacterial cell such as E. coli. The advantages of using E. coli include, but are not limited, to fast growth kinetics, high cell density cultures easily achieved, rich complex nedia can be made from readily available and inexpensive components and transformation with exogenous DNA is fast and easy.

Non-limiting examples of bacterial expression vectors include the pET series, pUC series, pQE vectors, ACYC and pBAD series of plasmid of E. coli expression vectors [Rosano Front. Microbiol., April 2014).

The skilled in the art would appreciate that the selection of vector depends on the origin of replication (e.g., pMB1, ColE1, p15A), promoters, selection markers and more.

Promoters—Numerous promoters are known in the art. According to a specific embodiment, the promoter is a constitutive promoter. According to a specific embodiment, the promoter is an inducible promoter. Following are some non-limiting examples: the lac promoter, a key component of the lac operon or its derivative lacUV5. Synthetic hybrids that combine the strength of other promoters and the advantages of the lac promoter are available. For example, the tac promoter consists of the −35 region of the trp (tryptophan) promoter and the −10 region of the lac promoter. This promoter is approximately 10 times stronger than lacUV5. Notable examples of commercial plasmids that use the lac or tac promoters to drive protein expression are the pUC series (lacUV5 promoter, Thermo Scientific) and the pMAL series of vectors (rac promoter, NEB). The T7 promoter system present in the pET vectors (pMIBI ori, medium copy number, Novagen) is commonly used for recombinant protein expression. In this system, the gene of interest is cloned behind a promr-ioter recognized by the phage T7 RNA polyinerase (T7 RNAP). This highly active polymerase should be provided in another plasmid or, most commonly, it is placed in the bacterial genome in a prophage (λDE3) encoding for the T7 RNAP under the transcriptional control of a lacUV5 promoter. Thus, the system can be induced by lactose or its non-hydrolyzable analog isopropyl β-D-1-thiogalactopyranoside (IPTG). Basal expression can be controlled by lacI$^Q$ but also by T7 lysozyme co-expression. T7 lysozyme binds to T7 RNAP and inhibits transcription initiation from the T7 promoter. In this way, if small amounts of T7 RNAP are produced because of leaky expression of its gene, T7 lysozyne will effectively control unintended expression of heterologous genes placed under the T7 promoter. T7 lysozyme is provided by a compatible plasmid (pLysS or pLysE). After induction, the amount of T7 RNAP produced surpasses the level of polymerase that T7 lysozyme can inhibit. The "free" T7 RNAP can thus engage in transcription of the recombinant gene. Yet another level of control lies in the insertion of a lacO operator downstream of the T7 promoter, making a hybrid 17/lac promoter. All three mechanisms (tight repression of the lac-inducible T7 RNAP gene by lacI$^Q$, T7 RNAP inhibition by T7 lysozyme and presence of a lacO operator after the T7 promoter) make the system ideal for avoiding basal expression.

Promoters that rely on positive control have lower background expression levels. This is the case of the araP$_{BAD}$ promoter present in the pBAD vectors. The AraC protein has the dual role of repressor/activator. In the absence of arabinose inducer, AraC represses translation by binding to two sites in the bacterial DNA. The protein—DNA complex forms a loop, effectively preventing RNA polymerase from binding to the promoter. Upon addition of the inducer, AraC switches into "activation mode" and promotes transcription from the car promoter. In this way, arabinose is absolutely needed for induction. Another widely used approach is to place a gene under the control of a regulated phage promoter. The strong leftward promoter (pL) of phage lambda directs expression of early lytic genes. The promoter is tightly repressed by the λcI repressor protein, which sits on the operator sequences during lysogenic growth. When the host SOS response is triggered by DNA damage, the expression of the protein RecA is stimulated, which in turn catalyzes the self-cleavage of λcI, allowing transcription of pL-controlled genes. This mechanism is used in expression vectors containing the pL promoter. The SOS response (and recombinant protein expression) can be elicited by adding nalidixic acid, a DNA gyrase inhibitor. Another way of activating the promoter is to control kcI production by placing its gene under the influence of another promoter. This two-stage control system has already been described for T7 promoter/T7 RNAP-based vectors. In the pLEX series of vectors (Life Technologies), the λcI repressor gene was integrated into the bacterial chromosome under the control of the trp promoter. In the absence of tryptophan, this promoter is always "on" and λcI is continuously produced. Upon addition of tryptophan, a tryptophan-TrpR repressor complex is formed that tightly binds to the trp operator, thereby blocking λcI repressor synthesis. Subsequently, the expression of the desired gene under the phL promoter ensues.

Transcription from all promoters described above is initiated by chemical cues. Systems that respond to physical signals (e.g., temperature or pH) are also available. The pL promoter is one example. A mutant λcI repressor protein (λcI$^{857}$) is temperature-sensitive and is unstable at temperatures higher than 37° C. E. coli host strains containing the λcI$^{857}$ protein (either integrated in the chromosome or into a vector) are first grown at 28-30° C. to the desired density, and then protein expression is induced by a temperature shift to 40-42° C. The industrial advantage of this system lies in part in the fact that during fermentation, heat is usually produced and increasing the temperature in high density cultures is easy. This temperature is suitable for expressing thermally stable proteins as in this case. On the other hand, genes under the control of the cold-inducible promoter cspA are induced by a downshift in temperature to 15° C., The pCold series of plasmids have a pUC118 backbone (a pUC18 derivative) with the cspA promoter.

Selection Markers—To deter the growth of plasmid-free cells, a resistance marker (gene) is added to the plasmid backbone. Thus, antibiotic resistance genes are habitually used for this purpose. Resistance to ampicillin is conferred by the bla gene whose product is a periplasmic enzyme that inactivates the β-lactam ring of β-lactam antibiotics. Other examples of genes that can be used are those which confer resistance to chloramphenicol, kanamycin and tetracycline.

Other elements can be included in the plasmids, and those are selected by the skilled artisan according to various parameters such as the host cell, the scale of production, the intended use of the resultant protein.

For isolating a purified soluble active recombinant protein, it is important to have means to (i) detect it along the expression and purification scheme, (ii) attain maximal solubility, and (iii) easily purify it from the cellular milieu (be it intracellular or secreted). The expression of a heterologous stretch of amino acids (peptide tag, referred to herein as "tag") or a large polypeptide (fusion partner) in tandem with the desired protein, in this case the albumin variant, to forirm a chimeric protein may allow these three goals to be straightforwardly reached.

Thus, according to an embodiment of the invention, the protein is an in-frame fusion with a heterologous tag, not naturally present in albumin.

Peptide tags are less likely to interfere when fused to the protein. Vectors are available that allow positioning of the tag on either the N-terminal or the C-terminal end (the latter option being advantageous when a signal peptide is positioned at the N-terminal end for secretion of the recombinant protein), Common examples of small peptide tags are the poly-Arg-, FLAG-, poly-His-, c-Myc-, S-, and Strep II-tags. Since commercial antibodies are available for all of them, the tagged recombinant protein can be detected by Western blot along expression trials, which is helpful when the levels of the desired proteins are not high enough to be detected by SDS-PAGE. Also, tags allow for one-step affinity purification, as resins that tightly and specifically bind the tags are available. For example, His-tagged proteins can be recovered by imrnobilized metal ion affinity chromatography using Ni$^{2+}$ or Co$^{2+}$-loaded nitrilotriacetic acid-agarose resins (see the Examples section which follows), while anti-FLAG affinity gels (Sigma-Aldrich) are used for capturing FLAG fusion proteins.

On the other hand, adding a non-peptide fusion partner has the extra advantage of working as solubility enhancers. The most popular fusion tags are the maltose-binding protein (M3P), N-utilization substance protein A (NusA), thioredoxin (Trx), glutathione S-transferase (GST), ubiquitin and SUMO, calcium binding protein Fh8

A different group of fusion tags which are also envisaged herein are stimulus-responsive tags, which reversibly precipitate out of solution when subjected to the proper stimulus. The addition of β roll tags to a recombinant protein allows for its selective precipitation in the presence of calcium. The final products present a high purity and the precipitation protocol only takes a couple of minutes, Another protein-based stimnulus-responsive purification tags are elastin-like polypeptides (FLPs), which consist of tandem repeats of the sequence VPGXG, where X is Val, Ala, or Gly in a 5:2:3 ratio. These tags undergo an inverse phase transition at a given temperature of transition (T$_t$). When the T$_t$ is reached, the ELP-protein fusion selectively and reversibly precipitates, allowing for quick enrichment of the recombinant protein by centrifugation. Precipitation can also be triggered by adjusting the ionic strength of the solution. These techniques represent an alternative to conventional chromatography-based purification methods and can save production costs, especially in large-scale settings.

According to some embodiments of the invention, affinity chromatography can be used to recover the protein from the expression system following expression.

Poly-His, MBP or GST can be used to purify the fused protein by affinity chromatography, as poly-His binds to nickel column, MBP binds to amylose-agarose and GST to gluathione-agarose. MBP is present in the pMAL series of vectors from NEB and GST in the pGEX series (GE). A peptide tag is preferably added to the fusion partner-containing protein if an affinity chromatography step is needed in the purification scheme. MBP and GST bind to their substrates non-covalently. On the contrary, the HaloTag7 (Promega) is based on the covalent capture of the tag to the resin, making the system fast and highly specific.

According to another embodiment, the protein variant is expressed tagless, i.e., without a tag. Alternatively, the tag is removed following expression and purification. Regardless, the resultant protein product is tagless (e.g., SEQ ID Nos: 3, 5, 7, 11, 13 and 15).

Thus, embodiments of the invention envisage isolating the protein from the bacteria or conditioned medium thereof once sufficient levels are achieved.

According to a specific embodiment the tag is removed to avoid interference with protein activity and/or structure, but on the other embodiments they can be left in place even for crystallographic studies. Tags can be eliminated by either enzymatic cleavage or chemical cleavage.

Recovery of the recombinant protein variant is effected following an appropriate time in culture. The phrase "recovering the recombinant polypeptide" refers to collecting the whole fermentation medium containing the polypeptide and need not imply additional steps of separation or purification. Alternatively the protein can be recovered from the intracellular space (e.g., cytosol) following lysis and optionally sonication (see Examples section which follows). Notwithstanding the above, proteins of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In some applications, particularly in applications where there is a desire to use non-animal origin components, it is advantageous to combine recombinantly produced albumin with some or all of the following compounds when they are produced recombinantly or naturally by microbial systems: insulin, transferrin, IGF1, EGF or other proteins, growth factors and metabolites.

Thus the protein variants can be used in cell culture media component in diagnostic kits, stabilizer of protein solutions applications within the pharmaceutical area such as blood expanders and excipients, digestive support, removal of toxins, imaging-radiologic or ultrasonic imaging, drug delivery, coating of surfaces e.g. medical devices, invitro fertilization-both as storage medium of egg alone, sperma alone, but also for culturing of egg+sperma.

The serum albumin according to the invention can replace albumin derived from any animal species, most particular from human or bovine sources, or recombinant animal albumins, at an equivalent or better function for all uses of albumin. The reasons for this includes: 1) The invention, as it is herein described, naturally creates beneficial species of small molecules bound to the albumin molecules, including, but not limited to, molecules such as fatty acids, vitamins, amino acids, phospholipids and cations; and 2) It does not contain the high amounts of caprylic acid and N-acetyl DL tryptophan that many manufacturers of native and recombinant albumin use as stabilizers. It is well known that fatty acid and cation binding to albumin produce conformational changes which further affect both cooperative and competitive interactions of fatty acids and drugs. Excessive amounts of caprylic acid and/or N-acetyl DL tryptophan often have unwanted or adverse effects in many albumin applications. The use of recombinant human albumin in critically ill patients has thus been shown to increase mortality. (Olsen H, Andersen A, Nordbo A, Kongsgaard U E, Bormer O P, 2004. Pharmaceutical grade albumin: impaired drug binding capacity in vitro. BMC Clinical Pharmacology, 4:4 doi:10: 1186/1472-69044-4; Keenan J, Dooley M, Pearson D, Clynes M. Recombinant human albumin in cell culture: Evaluation of growth promoting potential for NRK and Scc-9 cells in vitro. Cytotechnology 1997, 24:243-52; Zunszain, P A, Monie T, Konarev P V, Svergun D V, Curry S (2003). Structural analysis of conformational changes in human serum albumin associated with ligand binding and pH. www-hasylab(dot)desy(dot)de?science/annual_report/ 2003_report/part2/contrib./73/9-952(dot)pdf).

According to an aspect of the invention there is provided a composition comprising the protein variant.

According to some embodiments, the protein (with or without a tag, or as a chimera where it is fused to another active protein) can be purified such that it constitutes at least 50%, 60%, 70%, 80%, 90%, 95%, 99% of the proteins in the composition w/w or w/v.

When formulated with another protein (but not covalently) it can be present at any level even such as lower than 50% w/w or w/v.

Thus, according to an aspect of the invention, there is provided a composition comprising the protein variant and an active ingredient, which can also be referred to as "payload".

According to an embodiment of the invention, the active ingredient is a protein.

According to a specific embodiment, the proteinaceous active ingredient is a peptide, a growth factor, an antibody, a hormone, a cytokine or an interleukin.

According to a specific embodiment, the antibody is an intact antibody or a fragment thereof such as a Fac fragment or a single chain (ScFv) antibody.

For instance, the protein variant can be used to target to a tumor site or to increase the half-life of the active ingredient in the serum.

Antibody fragments such as ScFvs have a molecular mass lower than 25 KDa and are cleared rapidly from the circulation. A T84.66 ScFv-HAS fusion was shown to accumulate in tumors (reviewed in Fanali 2012 Molec. Aspects of Medicine 33 (209-290)).

According to another embodiment, the active ingredient is a non-proteinaceous agent such as a small molecule, a nucleic acid agent, a fatty acid or a lipid, an ion [e.g., HSA displays a wide variety of binding sites for several metal ions, including Mg(II), Al(III), Ca(II), Mn(II), Co(II/III), Ni(II), Cu(I/II), Zn(II), Cd(II), Pt(II), Au(I/II), Hg(II), and Tb(III)].

According to another embodiment, the active ingredient is a drug e.g., propranolol, salicylate, diazepam, valproic acid, and sulfafurazole, warfarin. Thus, the high affinity variants described herein can be used to modulate the pharmacokinetics of drugs.

According to some embodiments, the active ingredient is attached to the protein in a covalent or non-covalent manner.

According to a specific embodiment, the composition is shaped as a tube. Fanali 2012 supra describes organic nanotubes which have been modified to include albumin in the inner or outer surface of the tube and can be used as a carrier for payload binding.

When used in the clinic, the composition can be used as a pharmaceutical composition where the albumin is the active agent (e.g., in the case of reduced blood volume) or the drug-carrier.

On the basis of clinical evidence, the use of albumin can be indicated in acute conditions, in which it is necessary to expand the volume and maintain the circulation, and in some chronic states of low serum albumin; there are some widely shared and fully agreed indications for the appropriate use of human albumin and indications that are occasionally appropriate, that is, when other criteria are fulfilled. Albumin is also used in all cases in which there is a contraindication to the use of non-protein colloids.

The albumin protein variant of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the biological and/or pharmaceutical effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Due to expression in bacteria the protein preparations are devoid of xeno animal/eukaryotic contaminations rendering them beneficial for clinical applications as well as the food industry, biotechnological industry and research.

Further in vitro and in vivo applications of the protein variants according to the present invention include but are not limited to:

i) the culture of mammalian cells (e.g., lines or primary) for research, food (e.g., meat, milk industry), diagnostic or therapeutic purposes; the culture of genetically engineered or non-genetically engineered mammalian cells, including but not limited to CHO, Sp2/0, NS0, BHK, HEK 293, Namalwa and PERC.6, A431, hybridoma cells for the production of biopharmaceuticals, diagnostic reagents or native or recombinant proteins, or adenoviruses to be used for medical or cosmetic purposes, and culture media for the same; the culture of normal primary human cells, for example those offered commercially from Clonetics, Cascade or Cell Applications, and culture media for the same; the culture of stem cells, for example cells available from Stem Cell Technologies or patient derived samples for bone marrow trans-plants or myocardial infarct repair, and culture media for the same; the culture of mammalian fibroblasts with and without kerotinocytes, for example Dermagraft™ from Smith+Nephew, and the culture media for the same; the culture and expansion of mammalian tissue for implant and lesion repair, for example autologous chondrocyte implantation or myocyte implantation, and culture media for the same; (Yamane I. 1978. Development and application of a serum-free culture medium for primary culture. In H. Katsuta (ed), Nutritional Requirements of Cultured Cells. Baltimore, University Park Press, pp 1-21; U.S. Pat. No. 5,021,349; Iscove N N, Melchers F (1978). Complete replacement of serum by albumin, transferrin and soybean lipid in cultures of lipopolysaccharide-reactive B lymphocytes. J Exp Med 147: 928-33; U.S. Pat. Nos. 5,198,349; 5,250,421; Berntorp E (1997). Thrombosis Haemostasis 78: 256-60; McGrew J T, Richards C L, Smidt P, Dell B and Price V. 1998. Lipid requirements of a recombinant Chinese Hamster Ovary Cell Line (CHO), ibidem, pp 205-207; Yamane I. 1978. Role of bovine albumin in a serum-free culture medium and its application. Natl Cancer Inst Monogr 48:131-133; Sato J D, Kawamoto T, McClure D B and Sato G H. 1984. Cholesterol requirement of NS-1 mouse myeloma cells for growth in serum-free medium. Mol Biol Med 2(2):121-134; Kovar J. Hybridoma cultivation in defined serum-free media: growth-supporting substances. IV. Lipids and serum albumin. Folia Biol (Praha). 1987, 33(6):377-84; Jaeger, V, Lehmann J, Friedl P. Serum-free growth medium for the cultivation of a wide spectrum of mammalian cells in stirred bioreactors. Cytotechnology 1988, 1:319-29; Glassy C M, Tharakan J P, Chau, P C. Serum-free media in hybridoma culture and monoclonal antibody production. Biotech Bioeng 1988, 32:1015-28).

ii) use as a cryoprotectant for mammalian cells; (Somlo G, et al (1997). Effect of CD34+ selection and various schedules of stem cell reinfusion and granulocyte colony stimulating factor priming on hematopoetic recovery after high-dose chemotherapy for breast cancer. *Blood* 89: 1521-8; U.S. Pat. No. 6,548,297; WO01/37655; JRH Biosciences Catalog, 2004. Section on general cell culture techniques.

iii) use in or for process solutions used in mammalian assisted reproduction techniques; (Armstrong J S, Rajasekaran M, Hellstom W J G, Sikka S C (1998). Antioxidant potential of human serum albumin: role in recovery of high quality spermatozoa for assisted reproductive technology. J Androl 19:412-9; Vande-Voort C A (2004). High quality sperm for non-human primate ART: Production and assessment. Reproduct Biol Endocrinol, 2: 33-8; Lane M, Maybach J M, Hooper K, Hasler J F, Gardner D K (2002). Cryo-survival and development of bovine blastocysts are enhanced by culture with recombinant albumin and hyaluronan Molecular Reproduction & Development 64: 70-8; Gardner, D K (2004). U.S. Pat. No. 6,762, 053. Mammalian gamete and embryo culture media and culture media supplements.

iv) use in solutions for the preservation of donor organs; (US patent application 20040029096).

v) use in ocular applications; (Shimmura S, Ueno R, Matsumoto Y, Goto E, Higuchi A, Shimazaki J, Tsubota K (2003). Albumin as a tear supplement in the treatment of severe dry eye. Brit J Opthalmology 87:1279-83; U.S. Pat. No. 6,043,213).

vi) use in therapeutic applications as a plasma expander or for osmotic control, similar to the products Buminate (Baxter Intl), Plasbumin (Bayer Corp.) and Hextend (BioTime); (Woodruff L M, Gibson S T (1942). The clinical evaluation of human albumin. *US Navy Med Bull* 40:791-6; Heyl J T, Gibson J G II, Janeway C A (1943). Studies on the plasma proteins. V. The effect of concentrated solutions of human and bovine serum albumin on blood volume after acute blood loss in man. *J Clin Invest* 22: 763-73; Alderson P, Bunn F, Lefebvre C, Li Wn Po A, Li L, Roberts I, Schierhout G (2004). Human albumin solutions for resuscitation and volume expansion in critically ill patients. *The Cochrane Database of Systematic Reviews*, Issue 4. Art No. CD001208.pub2.DOI: 10.1002/14651858.CD001208.pub2)

vii) use as an excipient in the manufacture or formulation of pharmaceuticals or as a carrier, protecting agent, stabilizer or other use involving non-covalent association of another molecule, such as a drug, peptide or protein with the albumin (for example albumin-bound paclitxel suspension), for diagnostic or therapeutic use, including hormones (for example IGF-1 or insulin) and cytokines; (Tarelli E, et al (1998). Recombinant human albumin as a stabilizer for biological materials and for the preparation of international reference reagents. *Biologicals* 26: 33146; Paul W, Sharma C P (2005). Bioceramics, Towards Nano-enabled Drug Delivery: A mini Review. Trends Biomater. Artif Organs, 19: 7-11; Roddie, P H, Ludlam C A (1997). Blood Reviews 11:169-77).

viii) use in cosmetics or medical cosmetic procedures; (Sidle D M, Loos B M, Ramirez A L, Kabaker S S, Maas C S (2005). Use of BioGlue Surgical Adhesive for brow fixation in endoscope browplasty. Arch Facial Plast Surg 7: 393-7).

ix) use for inclusion in, on, or in the manufacturing of medical devices, including dental or dental implant applications, bone repair materials and biocompatible substances; (Kinnari T J, Rihkanen H, Laine T, Salonen, E-M, Jero, J (2004). Albumin-coated tympanostomy tubes: Prospective, double-blind clinical study. Laryngoscope 114: 2038-43; US patent application 20030004105.

x) use as a reagent in diagnostic procedures, kits or methods, for the purposes including but not limited to blocking non-specific adsorption of substances to surfaces, for local pH and osmolarity control in solution, to increase temperature stability of diagnostic or assay reagents, as a non-specific enzyme or small molecule stabilizer, as a stabilizer in the freezing or freeze-drying of small molecule, peptide and protein reagents.

xi) in the manufacture of human or veterinary vaccines, for example in Merck's MMR-II and MUMPSVAX vaccines, rabies vaccines, hepatitis A vaccine, the immunostabilization of virus in polymerized albumin; (U.S. Pat. No. 6,884,422; The BSE Inquirey: The Report (2000). Volume 16 chapter 4. www(dot)bseinquirey(dot)gov(dot)uk).

xii) use as a standard or reference material; (Bradford M (1976). A rapid and sensitive method for the quantitation of microgram quantities of protein utilizing the principle of dye-binding. Anal Biochem 72: 248-54).

xiii) use in or for adhesives or sealants, similar to CryoLife BioGlue C or albumin fixatives; (Fuerst W, Banedjee A (2005). Release of glutaraldehyde from an albumin-glutaraldehyde tissue adhesive causes significant in vitro and in vivo toxicity. Ann Thorac Surg 79:1522-8; Passage J, Tam R, Windsor M, O'Brien M (2005). BioGlue: A review of the use of this new surgical adhesive in thoractic surgery. ANZ J Surg 75:315-8; Hoffman G T, et al (2004). Composites containing albumin protein or cyanoacrylate adhesives and biodegradable scaffolds: I. Acute wound closure study in a rat model. Proc SPIE, 5312:117-23); Medical Adhesives & Sealants (2003). Study #1681. The Freedonia Group).

xiv) use in the removal of toxins (Cole and Lirenman, 1978, *J. Pediatr.* 92:955-957). xv) use in molecular biology applications, such as in restriction reactions or reactions done in extreme temperatures, such as PCR reactions, since their apparent melting temperatures are 70-100° C.

xvi) all other human or non-human applications and uses where an extracted or a recombinant mammalian albumin could be employed.

As such also provided herein are research compositions which comprise the albumin. Thus, according to an aspect there is provided a composition comprising a research reagent and the albumin protein as described herein.

According to some embodiments, the research reagent is selected from the group consisting of a buffer, an enzyme (e.g., restriction enzyme, polymerase) and a cell culture medium.

Examples of buffers includes, PBS, DPBS, HEPES, Tris, RIPA, MOPS, ME, MOPSO, ACES, TAPS, Bicine or Tricine.

In some applications, particularly applications where albumin is used as a cell culture ingredient which can be combined into a base culture medium, it is advantageous to load the albumin molecule with one or more ligands, including but not limited to fatty acids, vitamins, hormones and ions—e.g. copper, zinc etc.

Examples of base media for tissue culturing include, but are not limited to, MEM DMEM, RPMI-1640, IMDM, F12, Ham's F12, EMEM.

Typically albumin is added at an amount of 0.1-10 gr/L medium (e.g., 1 gr/L).

According to a particular embodiment, there is provided a method of cell culturing, the method comprising culturing cells in the presence of an albumin protein variant as described herein.

Any type of cell culturing method is envisaged herein, e.g., D2, 3D, large scale, small scale, suspension (without any matrix adherence) or adherent cultures.

According to a specific embodiment, said culturing is in serum-free medium or in the presence of serum up to 2%.

According to a specific embodiment, said cells are eukaryotic cells and optionally mammalian cells.

According to a specific embodiment, said cells are hybridoma cells.

According to a specific embodiment, said cells are bovine cells, chicken cells, duck cells, fish cells or pig cells.

According to a specific embodiment, said cells are stem cells or progenitor cells.

According to a specific embodiment, said cells are differentiated cells.

According to a specific embodiment, the albumin protein is formulated with any of a fatty acid, a vitamin, a hormone or an ion.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Computational design. HSA and BSA proteins (SEQ ID Nos: 1 and 9, respectively) were stabilized using a proprietary algorithm. For HSA, design was performed on two structures: pdb ID 2bx8—with 2 azopropazone ligands, and pdb ID 2bxi—with 7 myristate ligands and 2 azopropazone ligands. Positions interacting with ligands were restricted to design. Three designs with reduced sets of mutations were constructed, based on a proprietary algorithm design7 (SEQ ID NO: 17).

For BSA, design was performed on three structures (having different ligands and thus different conformations): pdb ID 6qs9 (with ketoprofen), 4jk4 (with 2-hydroxy 3,5-diiodobenzoic acid), and 4or0 (with naproxen). As in the case of HSA, three designs were tested experimentally, all based on design6 coming from 4or0 run (SEQ ID NO: 18).

Protein expression andpurification. Several constructs of HSA and BSA were tested. WT HSA and BSA (SEQ ID Nos: 1 and 9, respectively), and the designed genes (SEQ ID Nos: 2 and 10, respectively) were ordered from Twist Bioscience and cloned into a pET29b vector with C-terminal 6×His tag (His-tag version). HSA1 and BSA2 variants (SEQ ID Nos: 4 and 14, respectively) were also cloned into a pET28-SUMO vector with cleavable N-terminal bdSUMO tag (SUMO version), and HSA3 variant (SEQ ID NO: 8) was also cloned into a pET29b vector with deleted 6-His tag (no-His version). The His tag was added at C-term, SUMO tag was added at N-term.

All the variants were transformed into SHuffle T7 cells (NEB) and plated on LB plates with kanamycin (kana) and spectinomycin (spec). 10 ml of 2YT medium supplemented with 50 ug/ml kana and 50 ul/ml spec were inoculated with a single colony and grown overnight at 37° C. Then, 2YT medium supplemented with kana and spec (50-1500 ml of 2YT medium) was inoculated 1:100 with the overnight culture and grown at 37° C. until OD of ~0.6. Overexpression was induced with 0.3 mM IPTG, with which the cultures were grown for 18-20 h/20° C., harvested (5000 rpm/10 min/4° C.) and the pellet was frozen at −20° C. The cells were dispersed in lysis buffer (phosphate buffer saline (PBS)+1:10000 benzonase (Sigma-Aldrich #E1014)) and lysed by sonication.

His-tagged variants purification: The supernatant obtained after centrifugation (10,000 rpm/20 min/4° C.) was supplemented with 10 mM imidazole and mixed with Ni-Nta resin (2-3 h/4° C.), washed with 20 mM imidazole in PBS and the protein was eluted with 250 mM imidazole in PBS.

SUMO-tagged variants purification: The supernatant was purified on Ni-Nta resin as described before, but the elution was done by mixing overnight at 4° C. in PBS+1 mM DTT with 5 μg/ml bdSENP1 protease (19). The unbound fraction contained the tagless BSA/HSA variant.

No-His variants purification: The supernatant of HSA3 was incubated for 10 min at 90° C. and cleared by centrifugation (10,000 rpm/15 min/4° C.).

At the final stage, all the variants were purified by gel filtration chromatography, using HiLoad Superdex 200 column for preps coming from large scale expression (>500 ml culture) and HiLoad Superdex 75 column for preps coming from medium scale expression (50-500 ml culture).

Thermal stability measurements. Thermal stability of BSA and HSA variants (His-tagged form) and of commercial WT HSA and BSA (Sigma-Aldrich A1653 and A7638, respectively) was measured by nanoscale differential scanning fluorimetry (nanoDSF), in Prometheus NT.48 instrument (NanoTemper). The temperature was increased from 20° C. to 95° C. at 1° C./min ramp. Thermal stability of HSA variants was also measured by differential scanning calorimetry (DCS) in VP-DSC instrument (Malvern), with heating from 20° C. to 95° C. at 1° C./min and cooling at the same rate.

Ligand binding measurements. Ligand binding to commercial WT HSA (non-defatted, Sigma-Aldrich A1653) and to HSA1 variant (His-tagged) was measured at 25° C. by isothermal titration calorimetry (ITC, MicroCal iTC instrument, Malvern), in PBS supplemented with 1% DMSO.

HSA concentration was maintained at 40 μM in the cell, and 400 μM of warfarin (Sigma-Aldrich A2250) or ketoprofen (Sigma-Aldrich K1751) were loaded into the injector. The proteins were titrated with 10 ul ligands with a 3-min equilibration time. Titration of ligand to buffer (PBS with 1% DMSO) was used as a blank control, and one-site model was used to calculate the binding constants.

Crystallization and structure determination of HSA1 and Warfarin. Tagless HSA1 protein obtained from SUMO-HSA production was concentrated to 100 mg/ml in Tris buffer pH 7.0 and supplemented with 1 mM warfarin from 100 mM stock in DMSO. Crystals of HSA1 and warfarin were obtained using the hanging-drop vapor diffusion method with a Mosquito robot (TTP LabTech). All datasets were collected under cryogenic conditions at the European Synchrotron Radiation Facility (ESRF), Grenoble, France at beamline ID30B. The crystals were grown from 0.05 M NaCl, 10% PEG 4000 and 0.05 Tris pH=8.0. The crystals formed in the space group P1, with two monomers per asymmetric unit and diffracted to 2.0 Å resolution. The integrated reflections were scaled using the AIMLESS program (20) from the CCP4i2 program suite (21). HSA1 structure determined by molecular replacement with PHASER (22) using the structure of human serum albumin in complex with aristolochic acid (PDB code 6HSC). All steps of atomic refinement were carried out with the CCP4i2/REFMAC5 program (23) and by PHENIX.refine (24). The models were built into 2 mFobs-DFcalc, and mFobs-DFcalc maps by using the COOT program (25). The model was optimized using PDB_REDO (25, 26) and was evaluated with MOLPROBITY (27). Electron density revealed unambiguous density for the bound warfarin. Details of the refinement statistics of HSA1 and Warfarin structure are described in Table 1.

TABLE 1

| Data Collection | |
| --- | --- |
| PDB code | Not shown |
| Space group | P1 |
| Cell dimensions: | |
| a, b, c (Å) | 38.26 92.13 95.55 |
| α, β, γ (°) | 74.3, 89.3, 80.0 |
| No. of copies in a.u. | 2 |
| Resolution (Å) | 46.02-2.00 |
| Upper resolution shell (Å) | 2.04-2.00 |
| Unique reflections | 74,409 (4,259) |
| Completeness (%) | 89.1 (83.4) |
| Multiplicity | 10.2 (10.2) |
| Average I/σ(I) | 5.7 (1.1) |
| R-pim | 0.05816 (0.2589) |
| CC1/2 | 0.945 (0.86) |
| Refinement | |
| Resolution range (Å) | 46.02-2.00 |
| No. of reflections | 70,736 |
| No. of reflections in test set | 3,634 |
| R-working/R-free | 0.2258/0.2684 |
| No. of protein atoms | 8923 |
| No. of water molecules | 12 |
| Overall average B factor (Å²) | 42.98 |
| Root mean square deviations: | |
| bond length (Å) | 0.017 |
| bond angle (°) | 2.17 |
| Ramachandran Plot | |
| Most favored (%) | 96.55 |
| Additionally allowed (%) | 3.36 |
| Disallowed (%) | 0.09 |

* Values in parentheses refer to the data of the corresponding upper resolution shell

The crystal structure was deposited in the PDB-ID code 8A9Q.

Cell culture experiments. Tagless albumin variants were used for all the cell culture experiments. Hybridoma cells producing anti-GST monoclonal antibody (IgG1, Igk) were cultured for 2-4 days in the presence of 1% horse serum with or without 1 mg/ml of the following proteins: commercial HSA, HSA1, HSA3, commercial BSA, and BSA2. The number of live cells and the levels of produced antibody were analyzed via flow cytometry and ELISA respectively. For flow cytometry, cells were collected every 24 hours stained with NucBlue™ Live Cell Stain (ThermoFisher LTD), according to manufacturer protocol and analyzed using LSRII cell analyzer plate reader. For ELISA, sups were collected every 24 hours and binding to GST was assessed using standard anti GST produced in our facility.

HEK293T adherent cells were grown in DMEM supplemented with GlutaMAX, NEAA and 5% FBS (all from Gibco) at 37° C., 5% $CO_2$. To test the viability of the cultured cells in the presence of PROSS BSA2, HSA1 and HSA3 in comparison to the commercial BSA or HSA, respectively, cells ($\sim 3 \times 10^3$) were seeded in 24-well plate and followed each day for 5 days. All the albumin variants were added to the cells at 1 mg/ml in duplicates, and their effect was analyzed. As a control, no protein was added to the growth medium. In each time point, cells were collected and the number of total cells, live cells and % of viable cells were determined automatically using Brightfield Cell Counter DeNovix.

DNA Restriction. pET29b vector with 900 bp insert was restricted with NcoI and XhoI enzymes (NEB) overnight at 37° C., using the following buffers: rCutsmart buffer (NEB, contains 0.1 mg/ml rBSA), buffer 4 (NEB, identical composition to rCutsmart buffer, but no BSA), and buffer 4 supplemented with HSA1, BSA2, and HSA3 variants (tagless, after gel filtration and ion exchange purification) at 0.1 mg/ml.

Samples of pET28b(+) vector (1.5 µg) were restricted by BsiEI (10U, NEB) in 15 µl reaction volumes containing the Cutsmart buffer (NEB) or a reconstituted equivalent (50 mM Potassium acetate, 20 mM Tris-acetate, Mg-acetate, pH 7.9) supplemented with 0.1mg/ml of either commercial BSA (Sigma), HSA1, BSA2, or HSA3 variants (tagless, after gel filtration and ion exchange purification) at temperatures of 60-80° C. for 15 min using a gradient PCR (SensoQuest). Samples were then supplemented with 5 µl DNA sample buffer (150 mM TrisHCl pH 7.4, 5% SDS, 50% Glycerol, 0.05% Bromophenol Blue), heated (60° C., 10 min), and resolved on a 2% agarose-TAE gel containing 0.5 µg/mL Ethidium Bromide for 1.5h at 120V.

Example 1

Computational Design

In the most conservative design (HSA1 and BSA1=design 1), the present inventors allowed mutations only in the protein core and away from any of its binding sites. In the next design (HSA2 and BSA2=design 2), the present inventors also enabled design in surfaces outside the binding pockets. Binding pockets are amino acids in contact with small molecule ligands, which were observed in the crystal structures. Specifically, it is Sudlow sites I and II, and binding sites of myristate molecules, and in HSA3 and BSA3 (also termed design 3), mutations were allowed throughout the protein (FIGS. 2A-B, Tables 2, 3 and 4). It is envisioned that design 1 may find uses in settings in which all solvent-accessible surfaces must remain intact, such as in raising albumin-targeting antibodies. Design 2 can be used when only the ligand binding sites need to be conserved, and design 3 in those cases in which albumin is used for its osmotic or surface-binding properties. Furthermore, crystallographic analyses reveal two major conformations for albumin (compact and myristate-bound), and the present inventors used both in the design process, selecting mutations that are observed in both structures.

TABLE 2

| | | List of mutations in HSA variants | | | |
|---|---|---|---|---|---|
| Position # | Wild Type # mutations | HSA1-Conserved (no surface, no binding site mutations) 16 | HSA2-No surface mutations 25 | HSA3 - raw 73 | HSA_design_7 74 |
| 33 | Q | | | K | K |
| 38 | D | | | E | E |
| 39 | H | L | L | L | L |
| 42 | L | M | M | M | M |
| 44 | N | | | K | K |
| 52 | T | | | K | K |
| 58 | S | | | T | T |
| 76 | T | | | Q | Q |
| 95 | E | | | D | D |
| 99 | N | | | H | H |
| 116 | V | | | E | E |
| 120 | V | P | P | | |
| 125 | T | | | K | K |
| 136 | K | | N | N | N |
| 156 | F | Y | Y | Y | Y |
| 163 | A | | | K | K |
| 172 | A | | | E | E |
| 184 | E | | | A | A |
| 187 | D | E | E | E | E |
| 191 | A | | | E | E |
| 198 | L | H | H | Y | Y |
| 202 | S | I | I | I | I |

TABLE 2-continued

| | | List of mutations in HSA variants | | | |
|---|---|---|---|---|---|
| Position # | Wild Type # mutations | HSA1- Conserved (no surface, no binding site mutations) 16 | HSA2- No surface mutations 25 | HSA3 - raw 73 | HSA_design_7 74 |
| 210 | A | | | | V |
| 216 | V | | I | I | I |
| 227 | E | | | P | P |
| 229 | A | | | E | E |
| 231 | V | | | I | I |
| 243 | T | | | K | K |
| 244 | E | | | | A |
| 250 | L | | | M | M |
| 254 | A | | M | M | M |
| 259 | D | | | K | K |
| 286 | K | | | R | R |
| 297 | E | | | D | D |
| 298 | M | | | K | K |
| 300 | A | | | E | E |
| 304 | S | | | P | P |
| 310 | V | I | I | | |
| 328 | G | | | A | A |
| 329 | M | | | R | R |
| 344 | V | | T | T | T |
| 349 | L | | | I | I |
| 355 | T | | | D | D |
| 362 | A | | | K | K |
| 364 | A | | | E | E |
| 371 | A | S | S | | |
| 374 | F | | | E | E |
| 375 | D | | | E | E |
| 379 | P | | | K | K |
| 381 | V | I | I | | |
| 384 | P | | | T | T |
| 397 | Q | | | K | K |
| 402 | K | | | Y | Y |
| 409 | V | I | I | I | I |
| 415 | V | | | M | M |
| 419 | S | | | P | P |
| 421 | P | | | D | D |
| 426 | V | | | L | L |
| 427 | S | A | A | T | T |
| 440 | H | | L | L | L |
| 443 | A | | | E | E |
| 446 | M | | | L | L |
| 449 | A | | I | I | I |
| 455 | V | I | I | I | I |
| 470 | S | | N | N | N |
| 486 | P | | | H | H |
| 513 | I | | | L | L |
| 519 | K | E | E | E | E |
| 524 | K | | | M | M |
| 527 | T | | | K | K |
| 528 | A | | F | F | F |
| 541 | K | | | E | E |
| 547 | V | | I | | |
| 552 | A | S | S | T | T |
| 562 | D | | | E | E |
| 564 | K | | | P | P |
| 573 | K | | | S | S |
| 576 | V | I | I | I | I |
| 578 | A | | | K | K |

TABLE 3

| | | | BSA2 - no | | |
| | | BSA1 - | surface | BSA3 - | |
| | Wild Type | conserved | mutations | raw | |
| Position # | # mutations | 16 | 29 | 72 | BSA_4or0_design_6 |
|---|---|---|---|---|---|
| 21 | G | A | A | A | |
| 28 | S | A | A | A | A |
| 33 | Q | | | K | K |
| 39 | H | L | L | L | L |
| 42 | L | M | M | M | |
| 45 | E | | | D | D |
| 52 | T | | | K | K |
| 60 | A | | | P | P |
| 63 | E | | | S | S |
| 74 | L | | | | I |
| 78 | A | | | E | E |
| 79 | S | | | E | E |
| 92 | E | | | S | S |
| 109 | S | | | N | N |
| 124 | D | | | K | K |
| 128 | A | | | E | E |
| 138 | L | I | I | I | I |
| 158 | N | | | K | A |
| 162 | G | | | K | K |
| 163 | V | I | I | I | |
| 174 | G | A | A | A | A |
| 183 | T | | | A | A |
| 184 | M | I | I | I | I |
| 189 | L | | | K | K |
| 202 | I | L | L | L | L |
| 214 | S | | | | F |
| 226 | E | | | P | P |
| 228 | V | | | E | E |
| 230 | V | I | I | I | I |
| 240 | V | | I | I | I |
| 241 | H | | Y | Y | Y |
| 253 | A | | M | M | M |
| 258 | D | | | K | K |
| 260 | A | | V | V | V |
| 285 | K | | | R | R |
| 292 | V | | | | L |
| 294 | K | | | N | F |
| 296 | A | | | D | D |
| 300 | N | | | D | D |
| 305 | T | | | | V |
| 309 | A | L | L | L | L |
| 321 | A | | | D | D |
| 328 | S | | | R | R |
| 344 | V | | L | L | L |
| 351 | E | | | | V |
| 361 | A | | | K | K |
| 371 | T | | | R | R |
| 374 | D | | | E | E |
| 378 | H | | | K | K |
| 379 | L | | | H | H |
| 380 | V | I | I | I | I |
| 385 | N | | | E | |
| 387 | I | | | | V |
| 408 | V | I | I | I | I |
| 412 | R | | | K | K |
| 414 | V | | M | M | M |
| 418 | S | | | P | P |
| 420 | P | | | D | D |
| 425 | V | | I | I | |
| 426 | S | T | T | T | |
| 438 | T | | | Q | Q |
| 439 | K | | L | L | L |
| 442 | S | | | E | E |
| 443 | E | | | K | K |
| 445 | M | | L | L | L |
| 485 | P | | H | H | H |
| 500 | A | | | P | P |
| 503 | E | | | P | P |
| 517 | D | | | P | P |
| 518 | T | E | E | E | E |
| 520 | K | | | | L |
| 526 | T | | | K | K |
| 527 | A | | F | F | F |

TABLE 3-continued

| | | | | List of mutations in BSA variants | |
|---|---|---|---|---|---|
| Position # | Wild Type # mutations | BSA1 - conserved 16 | BSA2 - no surface mutations 29 | BSA3 - raw 72 | BSA_4or0_design_6 |
| 546 | V | | I | I | |
| 551 | V | | T | T | T |
| 553 | F | | | | M |
| 559 | A | | | K | K |
| 561 | D | | | E | E |
| 569 | V | | | E | E |
| 575 | V | I | I | I | I |
| 576 | V | | | E | E |
| 577 | S | | | K | K |
| 580 | T | | | A | A |

TABLE 4

Number of mutations, stability, expression levels
and binding affinities of HSA and BSA variants.

| Protein | # mutations (% protein mutated) | Melting temperature nanoDSF (DSC), ° C. | Bacterial expression, mg/L culture (see for comparison Z. Chen et al, Biochimica et Biophysica Acta 2013, 1830: 5515-5525 | Binding affinity, μM |
|---|---|---|---|---|
| HSA WT (commercial) | 0 | 60 | <2 | Warfarin: 19.4 ± 6.0 Ketoprofen: 32.7 ± 10.1 (SEE FOR COMPARISON Petitpas I. et al 2001, Journal of Biological Chemistry 276(35): 22804-22809) |
| HSA1 (no surface, no binding site mutations) | 16 (2.7) | 86 | 10-15 | Warfarin: 3.9 ± 0.1 Ketoprofen: 7.4 ± 1.6 |
| HSA2 (no surface mutations) | 25 (4.3) | 90 | ~40 | |
| HSA3 (mutations all over the protein) | 73 (12.5) | >95 (100.5) | ~100 | |
| BSA WT (commercial) | 0 | 58 | <2 | |
| BSA1 (no surface, no active site mutations) | 16 (2.7) | | <2 | |
| BSA2 (no surface mutations) | 29 (5.0) | 70 | ~20 | |
| BSA3 (mutations all over the protein) | 72 (12.3) | 85 | ~100 | |

Example 2

Expression and Thermal Stability of HSA and BSA Designs

As expected, WT HSA did not express in a soluble manner, but the designed HSA variants were soluble, and the expression levels increased with the number of stabilizing mutations (not shown), from ~10 mg/L culture for HSA1 to ~100 mg/L culture for HSA3. A similar behavior was obtained for BSA variants, but WT BSA had some soluble expression, and BSA1 showed only a modest increase in expression level. Size exclusion chromatography demonstrated that the His-tagged proteins are monomeric (FIGS. 17-26).

The thermal stability of HSA and BSA variants was tested by nanoDSF, and compared to that of commercial (WT) HSA and BSA samples (Table 4). As expected, thermal stability increased with the number of stabilizing mutations. HSA variants had $T_M$ values of 86-101° C., an increase of 26-40° C. relative to the commercial WT HSA (FIGS. 4-8). BSA1 variant didn't melt, and BSA2 and BSA3 designs had $T_M$ values of 70 and 85° C. respectively, 12-27° C. higher $T_M$ values than the WT BSA (FIGS. 9-12).

Encouraged by the soluble expression and the increased thermostability of HSA and BSA variants, the present inventors proceeded to further functional characterization with the most conserved improved variants, HSA1 and BSA2. To obtain tagless proteins, the present inventors have expressed the HSA1 and BSA2 in fusion with the SUMO tag (Frey and Görlich (2014) J. Chromatogr. A. 1337, 95-105), which was cleaved without any damage to the protein during purification. Gel filtration profiles demonstrated that HSA1 protein purified from SUMO-fused constructs was completely monomeric, and BSA2 protein in some preps had similar proportions of monomeric and dimeric fractions (FIGS. 23-25). Dimerization of albumin is a known process in mammalian albumins (28), and since no aggregates were observed, it was concluded that the present recombinant HSA1 and BSA2 could be purified in a tagless form.

Example 3

Ligand Binding by HSA1

Binding of various ligands is the primary biological activity of HSA. Ligand binding capacity of HSA1, the variant with no mutations in the active sites, was compared to that of the commercial WT HSA. Binding of two site-specific drug ligands, warfarin, which binds to Sudlow site I, and ketoprofen, which binds to Sudlow site II (Rabbani and Ahn International journal of biological macromolecules 123 (2019): 979-990), was measured by ITC. Binding affinities of HSA1 for these ligands were similar and even better than those obtained for the commercial WT HSA (Table 4, FIGS. 13-16). This indicates that the stabilized HSA1 variant retained the ligand binding capacity in the two primary binding sites.

Example 4

Crystal Structure of HSA1

In order to validate the structure of HSA1 variant, it was crystallized in complex with warfarin. The crystals had two monomers per asymmetric unit and diffracted to 2.0 Å resolution. The warfarin is indeed occupying its binding site (FIG. 3), as in the plasma-derived WT HSA structure (pdb ID 2bxd). In addition, four molecules of myristate fatty acid are present in the structure, in the same locations as in the structure of WT HSA (pdb ID 2bxi). Since no myristate was added during protein production, the source of myristate the 2YT medium, and/or the *E. coli* bacteria. The overall structure of HSA1 overlaps well with the open conformation structure of plasma-derived WT HSA with myristate (pdb ID 2bxd, rmsd 0.82 Å). All the 17 disulfide bonds were identified in the structure, as well as the free Cys34, and no significant changes in the side chain conformations were observed. These results demonstrate that stabilized HSA expressed in *E. coli* is folded to the same structure as the HSA from blood serum, with the capacity of myristate binding, as well as other ligands of HSA.

Example 5

Stabilized HSA and BSA variants in cell culture and in vitro applications

Figure 27A:
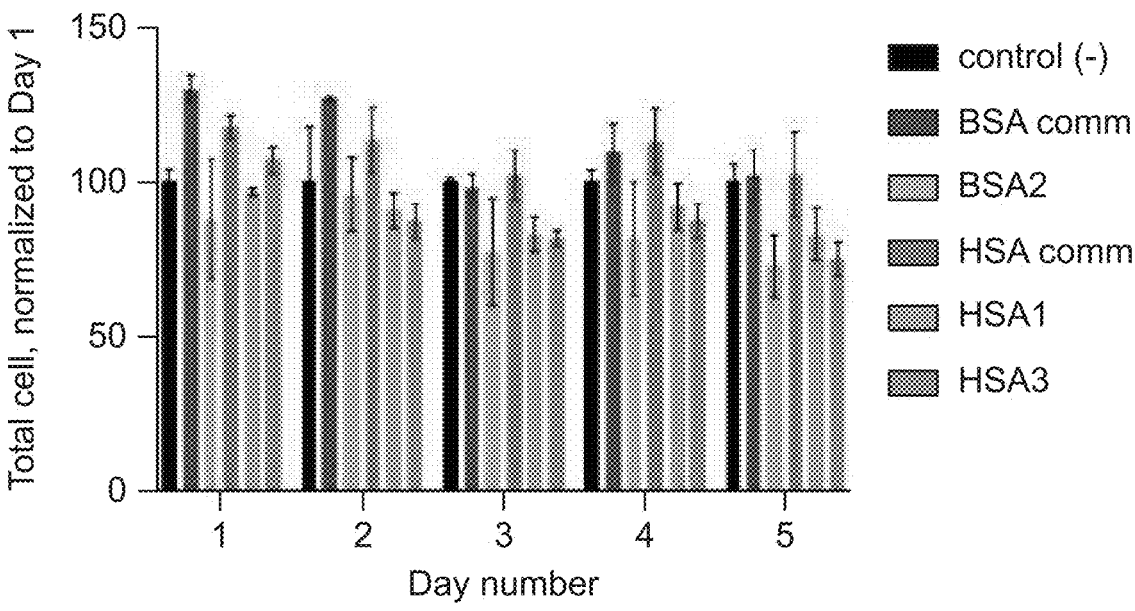
Figure 27B:
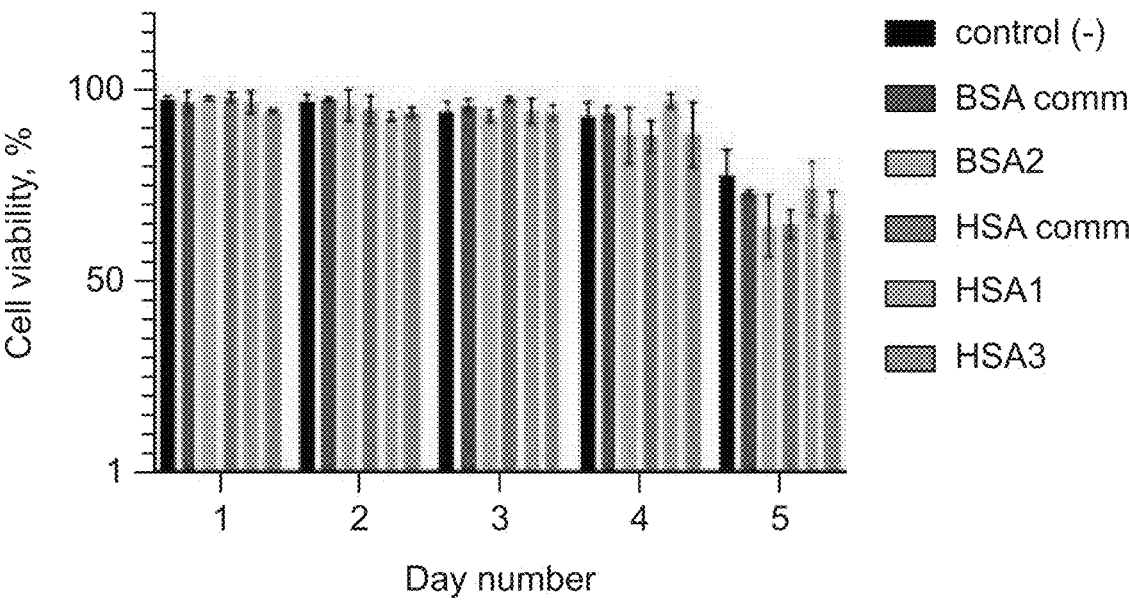
Figures 27C, 27D:
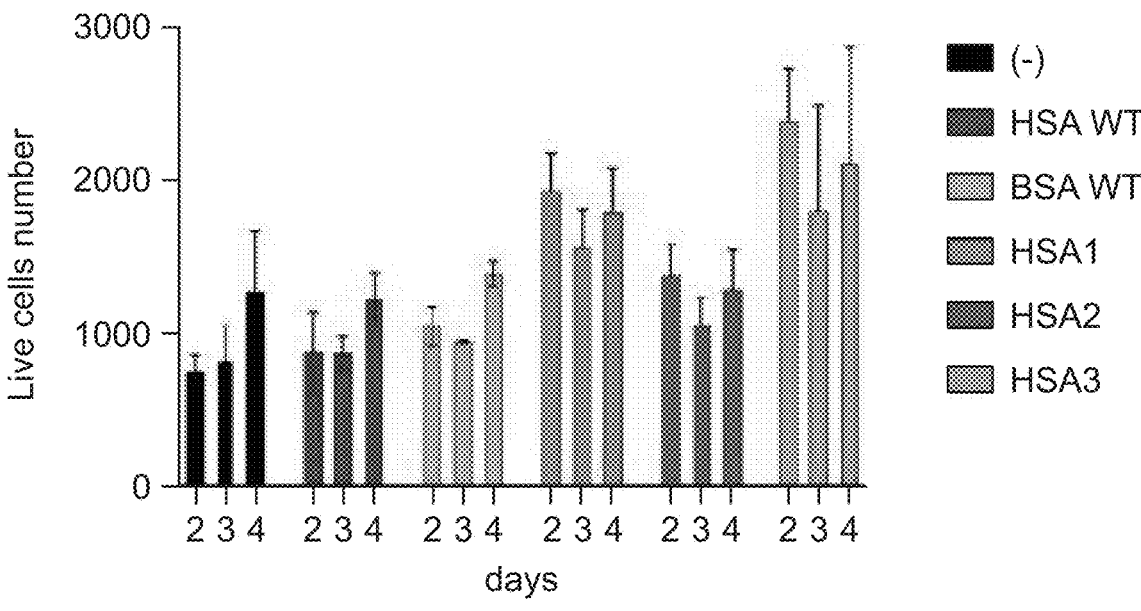

To test whether the albumin designs are not toxic to human cells and can be used in cell culture medium, they were added to the growth medium of HEK293T cells and hybridoma cells. In the case of HEK293T cells, there was no adverse effect of HSA1, HSA3, or BSA2 variants, as well as of the commercial plasma derived HSA and BSA, on both the number of cells and their viability (FIGS. 27A-B). Similarly, all the HSA and BSA design did not have any adverse effect on the number of live hybridoma cells, as well as on the produced antibody titers (FIGS. 27C-D). Based on these results, it can be concluded that the stabilized recombinant albumin variants are not toxic to HEK and hybridoma cells and could be considered for use in cell culture media.

To test whether the designed albumins can be used in molecular biology applications, restriction reactions were performed in which a buffer containing commercial BSA was compared to a buffer supplemented with stabilized albumins, HSA1, HSA3, or BSA2. In one case, pET28b(+) plasmid was digested using the enzyme BsiEI (FIGS. 28A-B), and in another case, pET29b(+) plasmid was digested with NcoI and XhoI enzymes (not shown). In both cases, the designs and commercial BSA performed equally well, producing the same restriction pattern with the same efficiency. The albumin designs can be used in reactions performed at extreme temperatures, such as PCR reactions, since their apparent melting temperatures are 70-100° C.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

1. Bujacz, A. (2012) Structures of bovine, equine and leporine serum albumin. Acta Crystallographica Section D Biological Crystallography. 68, 1278-1289
2. Albumin: Structure, Function and Uses (1977) 10.1016/c2013-0-02701-6
3. Rabbani, G., and Ahn, S. N. (2019) Structure, enzymatic activities, glycation and therapeutic potential of human serum albumin: A natural cargo. International Journal of Biological Macromolecules. 123, 979-990
4. Fanali, G., di Masi, A., Trezza, V., Marino, M., Fasano, M., and Ascenzi, P. (2012) Human serum albumin: from bench to bedside. Mol. Aspects Med. 33, 209-290
5. Kragh-Hansen, U., Chuang, V. T. G., and Otagiri, M. (2002) Practical Aspects of the Ligand-Binding and Enzymatic Properties of Human Serum Albumin. Biological and Pharmaceutical Bulletin. 25, 695-704
6. Chuang, V. T. G., Kragh-Hansen, U., and Otagiri, M. (2002) Pharmaceutical Research. 19, 569-577
7. Pace, C. N., Nick Pace, C., Vajdos, F., Fee, L., Grimsley, G., and Gray, T. (1995) How to measure and predict the molar absorption coefficient of a protein. Protein Science. 4, 2411-2423
8. Stout, A. J., Mirliani, A. B., White, E. C., Yuen, J. S. K., Jr, and Kaplan, D. L. (2021) Simple and effective serum-free medium for sustained expansion of bovine satellite cells for cell cultured meat. bioRxiv. 10.1101/2021.05.28.446057
9. Chen, Z., He, Y., Shi, B., and Yang, D. (2013) Human serum albumin from recombinant DNA technology: Challenges and strategies. Biochimica et Biophysica Acta (BBA)
General Subjects. 1830, 5515-5525
10. He, Y., Ning, T., Xie, T., Qiu, Q., Zhang, L., Sun, Y., Jiang, D., Fu, K., Yin, F., Zhang, W., Shen, L., Wang, H., Li, J., Lin, Q., Sun, Y., Li, H., Zhu, Y., and Yang, D. (2011) Large-scale production of functional human serum albumin from transgenic rice seeds. Proceedings of the National Academy of Sciences. 108, 19078-19083
11. Zhu, W., Gong, G., Pan, J., Han, S., Zhang, W., Hu, Y., and Xie, L. (2018) High level expression and purification of recombinant human serum albumin in Pichia pastoris. Protein Expr. Purif. 147, 61-68
12. Lawn, R. M., Adelman, J., Bock, S. C., Franke, A. E., Houck, C. M., Najarian, R., Seeburg, P. H., and Wion, K. L. (1981) The sequence of human serum albumin cDNA and its expression in *E. coli*. Nucleic Acids Research. 9, 6103-6114
13. Latta, M., Knapp, M., Sarmientos, P., Bréfort, G., Becquart, J., Guerrier, L., Jung, G., and Mayaux, J.-F. (1987) Synthesis and Purification of Mature Human Serum Albumin from *E. Coli*. Nature Biotechnology. 5, 1309-1314
14. Nguyen, M. T., Heo, Y., Do, B. H., Baek, S., Kim, C. J., Jang, Y. J., Lee, W., and Choe, H. (2020) Bacterial overexpression and purification of soluble recombinant human serum albumin using maltose-binding protein and protein disulphide isomerase. Protein Expr. Purif. 167, 105530
15. Sharma, A., and Chaudhuri, T. K. (2017) Revisiting *Escherichia coli* as microbial factory for enhanced production of human serum albumin. Microbial Cell Factories. 10.1186/s12934-017-0784-8
16. Goldenzweig, A., Goldsmith, M., Hill, S. E., Gertman, O., Laurino, P., Ashani, Y., Dym, O., Unger, T., Albeck, S., Prilusky, J., Lieberman, R. L., Aharoni, A., Silman, I., Sussman, J. L., Tawfik, D. S., and Fleishman, S. J. (2018) Automated Structure- and Sequence-Based Design of Proteins for High Bacterial Expression and Stability. Mol. Cell. 70, 380
17. Peleg, Y., Vincentelli, R., Collins, B. M., Chen, K.-E., Livingstone, E. K., Weeratunga, S., Leneva, N., Guo, Q., Remans, K., Perez, K., Bjerga, G. E. K., Larsen, Ø., Vaněk, O., Skořepa, O., Jacquemin, S., Poterszman, A., Kjær, S., Christodoulou, E., Albeck, S., Dym, O., Ainbinder, E., Unger, T., Schuetz, A., Matthes, S., Bader, M., de Marco, A., Storici, P., Semrau, M. S., Stolt-Bergner, P., Aigner, C., Suppmann, S., Goldenzweig, A., and Fleishman, S. J. (2021) Community-Wide Experimental Evaluation of the PROSS Stability-Design Method. J. Mol. Biol. 433, 166964
18. Weinstein, J. J., Goldenzweig, A., Hoch, S.-Y., and Fleishman, S. J. (2020) PROSS 2: a new server for the design of stable and highly expressed protein variants. Bioinformatics. 10.1093/bioinformatics/btaa1071
19. Frey, S., and Görlich, D. (2014) A new set of highly efficient, tag-cleaving proteases for purifying recombinant proteins. J. Chromatogr. A. 1337, 95-105
20. Read, R. J., Oeffner, R. D., and McCoy, A. J. (2020) Measuring and using information gained by observing diffraction data. Acta Crystallographica Section D Structural Biology. 76, 238-247
21. Potterton, L., Agirre, J., Ballard, C., Cowtan, K., Dodson, E., Evans, P. R., Jenkins, H. T., Keegan, R., Krissinel, E., Stevenson, K., Lebedev, A., McNicholas, S. J., Nicholls, R. A., Noble, M., Pannu, N. S., Roth, C., Sheldrick, G., Skubak, P., Turkenburg, J., Uski, V., von Delft, F., Waterman, D., Wilson, K., Winn, M., and Wojdyr, M. (2018) CCP4i2: the new graphical user interface to the CCP4 program suite. Acta Crystallographica Section D Structural Biology. 74, 68-84
22. McCoy, A. J., Grosse-Kunstleve, R. W., Adams, P. D., Winn, M. D., Storoni, L. C., and Read, R. J. (2007) Phaser crystallographic software. J. Appl. Crystallogr. 40, 658-674
23. Vagin, A. A., Steiner, R. A., Lebedev, A. A., Potterton, L., McNicholas, S., Long, F., and Murshudov, G. N. (2004) REFMAC5 dictionary: organization of prior chemical knowledge and guidelines for its use. Acta Crystallographica Section D Biological Crystallography. 60, 2184-2195
24. Headd, J. J., Echols, N., Afonine, P. V., Grosse-Kunstleve, R. W., Chen, V. B., Moriarty, N. W., Richardson, D. C., Richardson, J. S., and Adams, P. D. (2012) Use of knowledge-based restraints in phenix.refine to improve macromolecular refinement at low resolution. Acta Crystallographica Section D Biological Crystallography. 68, 381-390
25. Emsley, P., and Cowtan, K. (2004) Coot: model-building tools for molecular graphics. Acta Crystallogr. D Biol. Crystallogr. 60, 2126-2132
26. Joosten, R. P., Long, F., Murshudov, G. N., and Perrakis, A. (2014) The PDB_REDO server for macromolecular structure model optimization. IUCrJ. 1, 213-220

27. Chen, V. B., Arendall, W. B., 3rd, Headd, J. J., Keedy, D. A., Immormino, R. M., Kapral, G. J., Murray, L. W., Richardson, J. S., and Richardson, D. C. (2010) Mol-Probity: all-atom structure validation for macromolecular crystallography. Acta Crystallogr. D Biol. Crystallogr. 66, 12-21

28. Chubarov, A., Spitsyna, A., Krumkacheva, O., Mitin, D., Suvorov, D., Tormyshev, V., Fedin, M., Bowman, M. K., and Bagryanskaya, E. (2020) Reversible Dimerization of Human Serum Albumin. Molecules. 10.3390/molecules26010108

What is claimed is:

1. An albumin protein variant comprising:

the amino acid sequence set forth in SEQ ID NO: 3, 5 or 7; and wherein the albumin protein variant is soluble when expressed in bacteria and characterized by increased thermostability as compared to wild type human serum albumin (HSA) of SEQ ID NO: 1.

2. A polynucleotide comprising a nucleic acid sequence encoding the protein of claim 1.

3. A cell comprising the protein of claim 1.

4. A composition comprising the protein of claim 1 and an active ingredient.

5. The composition of claim 4, wherein said active ingredient is attached to the protein.

6. A method of producing albumin, the method comprising expressing in bacteria a nucleic acid sequence encoding the protein of claim 1, thereby producing albumin.

7. A method of cell culturing, the method comprising culturing cells in the presence of an albumin protein of claim 1.

* * * * *

SEQUENCE LISTING

```
Sequence total quantity: 18
SEQ ID NO: 1            moltype = AA  length = 586
FEATURE                 Location/Qualifiers
source                  1..586
                        mol_type = protein
                        note = Amino Acid sequence of mature HSA
                        organism = Homo sapiens
SEQUENCE: 1
MDAHKSEVAH RFKDLGEENF KALVLIAFAQ YLQQCPFEDH VKLVNEVTEF AKTCVADESA   60
ENCDKSLHTL FGDKLCTVAT LRETYGEMAD CCAKQEPERN ECFLQHKDDN PNLPRLVRPE  120
VDVMCTAFHD NEETFLKKYL YEIARRHPYF YAPELLFFAK RYKAAFTECC QAADKAACLL  180
PKLDELRDEG KASSAKQRLK CASLQKFGER AFKAWAVARL SQRFPKAEFA EVSKLVTDLT  240
KVHTECCHGD LLECADDRAD LAKYICENQD SISSKLKECC EKPLLEKSHC IAEVENDEMP  300
ADLPSLAADF VESKDVCKNY AEAKDVFLGM FLYEYARRHP DYSVVLLLRL AKTYETTLEK  360
CCAAADPHEC YAKVFDEFKP LVEEPQNLIK QNCELFEQLG EYKFQNALLV RYTKKVPQVS  420
TPTLVEVSRN LGKVGSKCCK HPEAKRMPCA EDYLSVVLNQ LCVLHEKTPV SDRVTKCCTE  480
SLVNRRPCFS ALEVDETYVP KEFNAETFTF HADICTLSEK ERQIKKQTAL VELVKHKPKA  540
TKEQLKAVMD DFAAFVEKCC KADDKETCFA EEGKKLVAAS QAALGL              586

SEQ ID NO: 2            moltype = DNA  length = 1758
FEATURE                 Location/Qualifiers
source                  1..1758
                        mol_type = other DNA
                        note = Nucleic Acid sequence of mature HSA
                        organism = Homo sapiens
SEQUENCE: 2
atggacgcac acaagagcga ggttgcccac cgtttcaagg acttaggaga ggagaatttc   60
aaggcattag tccttatcgc attcgcccaa tacttacaac aatgtccctt cgaggaccac  120
gttaagctcg taaatgaggt tacggagttc gccaagacgt gtgttgccga cgagagtgca  180
gagaattgtg acaagtcatt gcacacgtta ttcggtgaca agttgtgtac ggttgccact  240
cttcgtgaga catacgggga gatggccgac tgttgtgcca agcaagagcc agagcgtaat  300
gagtgtttct tacaacacaa ggacgacaat ccaaatttac ctcgtctcgt ccgtcctgag  360
gttgacgtaa tgtgtacggc tttccacgac aatgaggaga cgttcctcaa gaagtacttg  420
tacgagatcg cgcgccgtca cccatacttt tacgctccag agttactttt cttcgcaaag  480
cgttacaagg ccgctttcac tgagtgttgt caagccgccg acaaggccgc ctgtctctta  540
cccaagcttg acgagttgcg tgacgagggg aaggcaagtt ccgcaaagca acgtttaaag  600
tgtgcttcac tgcaaaagtt cggagagcgt gccttcaagg cttgggcagt tgcccgtttg  660
tctcaacgtt tcccaaaggc agagttcgca gaggtaagta agcttgtcac ggacttgaca  720
aaggttcaca cggagtgttg ccacggagac ctcttggagt gtgcagacga ccgtgcagac  780
cttgcaaagt acatctgtga gaatcaagac tcaatctcgt ctaagttaaa ggagtgttgt  840
gaaaagccct tgcttgaaaa gagtcactgt atcgcagagg tagagaatga cgagatgccc  900
gctgacttac cctcattggc cgcagacttc gtagagtcga aggacgtttg taagaattac  960
gccgaggcca aggacgtttt cttaggtatg ttcttgtacg agtacgcacg tcgtcacccc 1020
gactactcgg ttgtccttct cttacgttta gctaagacgt acgagacgac attggaaaag 1080
tgttgtgccg ctgccgaccc tcacgagtgt tacgctaagg tcttcgacga gttcaagcca 1140
ttggtagagg agccacaaaa tttaatcaag caaaattgtg agttattcga gcaactcggt 1200
gagtacaagt tccaaaatgc actcctcgta cgttacacga agaaggtacc ccaagtctct 1260
acgccaactc ttgttgaggt atcccgtaat cttgggaagg tcggaagtaa gtgttgtaag 1320
caccccgagg ctaagcgtat gccttgtgca gaggactact tatcagtagt cctcaatcaa 1380
ttgtgtgttt tgcacgaaaa gacgccagtt tccgaccgtg tcacaaagtg ttgtacagag 1440
agtctcgtta atcgtcgtcc ctgtttcagt gcattggaag tcgacgagac gtacgttcca 1500
aaggagttca tgcagagac tttcacattc cacgccgaca tctgtactct tagtgaaaag 1560
gagcgtcaaa tcaagaagca aacagccttg gtcgagcttg tcaagcacaa gcccaaggcc 1620
acgaaggagc aattaaaggc cgtaatggac gacttcgcag ccttcgtaga aaagtgttgt 1680
aaggccgacg acaaggagac ttgtttcgcc gaggaaggta agaagcttgt agccgctagt 1740
caagccgcct tgggcctg                                              1758

SEQ ID NO: 3            moltype = AA  length = 586
FEATURE                 Location/Qualifiers
source                  1..586
                        mol_type = protein
                        note = Albumin Synthetic variant
                        organism = synthetic construct
SEQUENCE: 3
MDAHKSEVAH RFKDLGEENF KALVLIAFAQ YLQQCPFEDL VKMVNEVTEF AKTCVADESA   60
ENCDKSLHTL FGDKLCTVAT LRETYGEMAD CCAKQEPERN ECFLQHKDDN PNLPRLVRPE  120
PDVMCTAFHD NEETFLKKYL YEIARRHPYF YAPELLYFAK RYKAAFTECC QAADKAACLL  180
PKLDELREEG KASSAKQRHK CAILQKFGER AFKAWAVARL SQRFPKAEFA EVSKLVTDLT  240
KVHTECCHGD LLECADDRAD LAKYICENQD SISSKLKECC EKPLLEKSHC IAEVENDEMP  300
ADLPSLAADF IESKDVCKNY AEAKDVFLGM FLYEYARRHP DYSVVLLLRL AKTYETTLEK  360
```

-continued

```
CCAAADPHEC YSKVFDEFKP LIEEPQNLIK QNCELFEQLG EYKFQNALLI RYTKKVPQVS   420
TPTLVEVARN LGKVGSKCCK HPEAKRMPCA EDYLSIVLNQ LCVLHEKTPV SDRVTKCCTE   480
SLVNRRPCFS ALEVDETYVP KEFNAETFTF HADICTLSEE ERQIKKQTAL VELVKHKPKA   540
TKEQLKAVMD DFSAFVEKCC KADDKETCFA EEGKKLIAAS QAALGL               586

SEQ ID NO: 4             moltype = DNA   length = 1758
FEATURE                  Location/Qualifiers
source                   1..1758
                         mol_type = other DNA
                         note = Albumin Synthetic variant
                         organism = synthetic construct
SEQUENCE: 4
atggatgcac ataaaagcga ggtggcacat cgtttttaagg atctgggcga ggagaacttt   60
aaagcactgg tgttgattgc tttcgctcag tatctccaac aatgcccgtt cgaagacttg   120
gttaagatgg taaatgaagt cacagaattt gcgaaaacct gtgtggctga tgagtcggcc   180
gagaattgcg acaaaagtct tcacacgctg tttggtgaca aactgtgcac tgttgctact   240
ctccgggaaa cttatggcga aatggcggac tgttgcgcaa aacaagagcc agagcgtaac   300
gagtgtttct tacagcacaa agacgacaac ccgaacctgc cgcgccctcgt ccgtccggaa   360
ccggatgtca tgtgtactgc gtttcatgac aatgaagaaa cattttttgaa aaagtatctg   420
tatgaaatcg ctcgccgcca cccgtacttt tacgccccag agttgctcta ttttgctaaa   480
cgttacaagg ccgcatttac ggaatgttgt caggcggctg ataaagcggc ttgtttgctg   540
ccgaaacttg atgagctgcg tgaggaaggg aaagcttcta gcgccaagca gcgtcataaa   600
tgtgccattc tccagaagtt tggcgaacgg gccttcaaag cgtgggcagt cgcacgtctg   660
agccaacgtt tcccgaaggc ggaatttgcc gaagtcagca aattggtgac agatctcact   720
aaagttcaca ccgagtgctg tcatggcgac ctgcttgaat gcgcggatga ccgggccgac   780
ctggctaaat atatctgcga aaaccaggat tcaattagct ccaaactgaa agaatgttgc   840
gagaaacccct tgctggagaa atcccattgc attgctgaag ttgaaaatga tgagatgccg   900
gccgatttgc cgagcctggc agctgatttc attgagtcaa aggacgtgtg caagaactat   960
gcagaagcca aagacgtttt tctgggtatg ttcctgtatg aatatgcccg ccgtcatccc   1020
gactatagcg tcgtgctgtt attgcgcctg gccaagactt atgagacgac cctggagaaa   1080
tgctgcgccg ctgctgatcc tcatgaatgc tattccaaag tattcgacga gttcaaaccg   1140
ttgatcgaag aaccgcaaaa tcttattaaa caaaattgcg aattgtttga caactgggc   1200
gagtacaaat ttcaaaatgc tctcttaatt cgttatacta agaaagtgcc gcaagtctcc   1260
acgcctacgc tggtagaagt cgcccgtaac ctgggtaaag taggctctaa atgctgtaag   1320
caccctgagg ccaagcggat gccttgcgcc gaagactact tgagcatcgt attgaatcag   1380
ctctgtgtgt tacacgagaa aaccccggtg tcagaccgtg tcacgaaatg ttgtaccgag   1440
agccttgtga accgtcgtcc atgcttctca gcactggaag ttgacgaaac atacgtgcca   1500
aaagagttta acgctgaaac ttttactttt catgcagaca tctgcacgtt gagcgaagaa   1560
gaacgtcaga ttaaaaagca gactgcgctg gtggagttag tgaaacataa acccaaagct   1620
actaaagaac agctcaaagc ggtcatggac gacttcagcg cctttgttga gaaatgctgc   1680
aaggcggacg ataaagagac ctgttttgcg gaagaaggta agaaactgat tgccgcaagc   1740
caggcagcac tggggctg                                               1758

SEQ ID NO: 5             moltype = AA   length = 586
FEATURE                  Location/Qualifiers
source                   1..586
                         mol_type = protein
                         note = Albumin Synthetic variant
                         organism = synthetic construct
SEQUENCE: 5
MDAHKSEVAH RFKDLGEENF KALVLIAFAQ YLQQCPFEDL VKMVNEVTEF AKTCVADESA   60
ENCDKSLHTL FGDKLCTVAT LRETYGEMAD CCAKQEPERN ECFLQHKDDN PNLPRLVRPE   120
PDVMCTAFHD NEETFLNKYL YEIARRHPYF YAPELLYFAK RYKAAFTECC QAADKAACLL   180
PKLDELREEG KASSAKQRHK CAILQKFGER AFKAWAIARL SQRFPKAEFA EVSKLVTDLT   240
KVHTECCHGD LLECMDDRAD LAKYICENQD SISSKLKECC IAEVENDEMP   300
ADLPSLAADF IESKDVCKNY AEAKDVFLGM FLYEYARRHP DYSVTLLLRL AKTYETTLEK   360
CCAAADPHEC YSKVFDEFKP LIEEPQNLIK QNCELFEQLG EYKFQNALLI RYTKKVPQVS   420
TPTLVEVARN LGKVGSKCCK LPEAKRMPCI EDYLSIVLNQ LCVLHEKTPV NDRVTKCCTE   480
SLVNRRPCFS ALEVDETYVP KEFNAETFTF HADICTLSEE ERQIKKQTFL VELVKHKPKA   540
TKEQLKAIMD DFSAFVEKCC KADDKETCFA EEGKKLIAAS QAALGL               586

SEQ ID NO: 6             moltype = DNA   length = 1758
FEATURE                  Location/Qualifiers
source                   1..1758
                         mol_type = other DNA
                         note = Albumin Synthetic variant
                         organism = synthetic construct
SEQUENCE: 6
atggatgcac ataaaagcga ggtggcacat cgtttttaaag atctgggcga agaaaatttt   60
aaagcgttag tgttgatcgc gttcgctcag tatttacaac aatgcccgtt cgaggatttg   120
gtcaaaatgg ttaacgaagt aacagagttt gcaaaaacct gtgtcgccga tgagtcagca   180
gagaactgcg ataaaagcct gcacacgctt ttcggcgata aactgtgcac tgtggctaca   240
ctccgcgaaa cgtatggtga aatggccgat tgttgcgcga acaggagcc ggaacgcaat   300
gaatgttttt tgcagcataa agatgataat ccaaatctcc cacggcctcgt tcgcccggag   360
cctgatgtta tgtgtaccgc attccacgac aatgaagaaa cgtttctcaa taagtacctg   420
tatgagattg ctcgtcgtca tccatacttt tacgctccgg aattactgta cttcgctaag   480
cgttacaagg cagcctttac agagtgctgt caagcggcag acaaagcggc ctgcttgctt   540
ccgaaacttg acgaacttcg cgaagaaggg aaagcctcgt ccgccaaaca acggcacaaa   600
tgtgccattc tccagaagtt tggtgagcgc gcatttaaag cgtgggccat tgcgcggctg   660
```

```
tcacagcgtt tcccgaaagc ggaatttgcg gaagtgagta aactggtgac tgatttgacg   720
aaagtgcata ccgaatgttg tcatggcgat ttgttggaat gcatggatga tcgtgcagat   780
ttagccaaat atatttgcga aaatcaggat agcatttcta gcaagctgaa agaatgttgt   840
gagaaacctc tgctggagaa atctcattgc atcgcggagg ttgaaaatga tgaaatgccg   900
gcggatctgc ctagtctggc agcggatttc attgaaagca aagatgtctg caagaattat   960
gcggaagcga aagatgtatt tttaggtatg tttctttacg agtatgctcg ccgtcacccg  1020
gattacagtg tcaccctgtt gctgcgctta gccaaacgt atgaaccac gctggaaaag  1080
tgttgcgccg cggcggaccc tcacgaatgt tattcgaaag tttttgatga gtttaaacct  1140
cttatcgagg agcccaaaa tctcattaaa caaaactgcg aactgtttga gcaactgggg  1200
gaatacaaat tccagaacgc tttattgatt cgctatacta agaaagtgcc ccaagtgtca  1260
acgccgacgc tggtagaagt tgcccgcaac ttagggaagg tgggcagcaa atgctgtaaa  1320
cttccagaag ctaagcgtat gccatgtatc gaagattatc tgtccattgt tctgaatcag  1380
ttatgtgtgc tccatgaaaa aaccctgtc aatgatcggg ttaccaagtg ctgcacggaa  1440
tccctcgtca atcgtcgccc atgctttagc gcccttgaag tagacgaaac atacgtcccg  1500
aaagagttca atgccgaaac gtttacctt catgcagaca tttgcaccct cagcgaggaa  1560
gaacgccaaa tcaaaaagca gaccttcctt gtggaacttg tgaagcataa accaaaagcg  1620
acgaaagaac agctgaaagc gattatggat gatttcagtg cctttgtaga aaagtgctgt  1680
aaagccgacg acaaagaaac atgctttgcg gaggagggca gaagctcat tgccgcaagc  1740
caggcagcac tggggctg                                                  1758
```

SEQ ID NO: 7       moltype = AA   length = 586
FEATURE            Location/Qualifiers
source             1..586
                    mol_type = protein
                    note = Albumin Synthetic variant
                    organism = synthetic construct
SEQUENCE: 7

```
MDAHKSEVAH RFKDLGEENF KALVLIAFAQ YLQKCPFEEL VKMVKEVTEF AKKCVADETA   60
ENCDKSLHTL FGDKLCQVAT LRETYGEMAD CCAKQDPERH ECFLQHKDDN PNLPRLERPE  120
VDVMCKAFHD NEETFLNKYL YEIARRHPYF YAPELLYFAK RYKKAFTECC QAEDKAACLL  180
PKLDALREEG KESSAKQRYK CAILQKFGER VFKAWAIARL SQRFPKAPFE EISKLVTDLT  240
KVHKACCHGD MLECMDDRAK LAKYICENQD SISSKLKECC EKPLLERSHC IAEVENDDKP  300
EDLPPLAADF VESKDVCKNY AEAKDVFLAR FLYEYARRHP DYSVTLLLRI AKTYEDTLEK  360
CCKAEDPHEC YAKVEEEFKK LVEETQNLIK QNCELFEKLG EYYFQNALLI RYTKKMPQVP  420
TDTLVELTRN LGKVGSKCCK LPEEKRLPCI EDYLSIVLNQ LCVLHEKTPV NDRVTKCCTE  480
SLVNRRHCFS ALEVDETYVP KEFNAETFTF HADLCTLSEE ERQIMKQKFL VELVKHKPKA  540
TEEQLKAVMD DFTAFVEKCC KAEDPETCFA EEGSKLIAKS QAALGL                 586
```

SEQ ID NO: 8       moltype = DNA   length = 1758
FEATURE            Location/Qualifiers
source             1..1758
                    mol_type = other DNA
                    note = Albumin Synthetic variant
                    organism = synthetic construct
SEQUENCE: 8

```
atggatgcac ataaaagcga ggtggcacat cgttttaaag atttaggtga agaaaacttt   60
aaagctctcg ttctgatcgc gtttgcccag taccttcaga aatgcccgtt cgaagagctc  120
gttaaaatgg tcaaagaggt aacggagttc gcgaagaaat gcgtagcaga tgaaactgcg  180
gaaaactgtg ataagtcttt acacactctt tttggagata agttatgcca agttgccacg  240
ctgcgtgaga cgtacggtga gatggcggat tgctgcgcaa aacaagatcc ggagcgtcac  300
gaatgctttt tgcagcacaa agatgacaac ccaaatttac cgcgtttgga gcgtccggaa  360
gtggatgtta tgtgtaaagc cttccacgat aacgaagaga cgtttttaaa taaatacctg  420
tacgaaattg cgcggcgtca tccatatttc tatcgcgccgg agcttctgta ttttgccaaa  480
cgttacaaga aggcttttac tgaatgctgc aggcggaag ataaagccgc gtgcttgctc  540
cctaagctgg atgccttgcg tgaggaaggt aaagaatctt cggccaaaca gcgctataaa  600
tgcgcgatcc tccagaaatt tggagagcgc gtctttaaag cgtgggccat tgcgcggctt  660
tcacagcgtt ttcctaaagc gccgtttgaa gagatctcga aactggttac cgatctgaca  720
aaagttcaca agcttgctg tcatggtgat atgctggaat gcatggacga tcgtgcgaaa  780
ctcgcgaaat atatttgcga aaatcaggat tcgattagtt ccaagcttaa agaatgctgc  840
gagaaaccgc tgttggaacg cagtcactgt attgcggaag tggagaacga tgataaaccg  900
gaggatctgc cgccattagc cgcagatttt gtggagagca agacgtctg caagaattat  960
gccgaggcaa aggatgtctt tctggctcgt ttccttatcg aatatgcgcg tcggcacccg  1020
gattactccg ttacctctt attgcgtatt gccaaaacgt atgaagatac cctggagaag  1080
tgctgcaagg cggaagatcc tcatgaatgt tacgcgaagg tcgaggagga atttaaaaag  1140
ctggtagaag aaacgcaaaa cttaatcaag caaaattgcg aattatttga aaactgggt  1200
gaatattatt ttcaaaacgc cctgctcatt cgctatacta agaaaatgcc gcaggtccca  1260
acggacacgc tcgtcgaatt gacccggaac ttaggcaaag tgggatcgaa atgctgtaaa  1320
cttccggaag agaaacgcct gccgtgcatc gaagattacc tctctatcgt gctcaaccag  1380
ctgtgtgttc tgcatgagaa gaccccggtg aatgatcgtg ttaccaagtg ctgtacggaa  1440
tcactggtta atcgtcgcca ttgctttagt gccctggaag tcgatgaaac ttatgtccca  1500
aaagagttca cgccgaaac atttacctt catgcggatt tgtgcaccct ttccgaagaa  1560
gaacgtcaga tcatgaaaca gaaatttctt gtcgagctgg tcaaacacaa accgaaagcc  1620
accgaagaac agctgaaagc agttatggac gatttcaccg cctttgttga aaatgctgt  1680
aaagccgaag atcctgaaac ctgctttgcg gaagaaggtt cgaaactgat tgccgcaagc  1740
caggcagcac tggggctg                                                  1758
```

SEQ ID NO: 9       moltype = AA   length = 584
FEATURE            Location/Qualifiers
source             1..584

-continued

```
                              mol_type = protein
                              note = Amino Acid sequence of mature BSA
                              organism = Bos taurus
SEQUENCE: 9
MDTHKSEIAH RFKDLGEEHF KGLVLIAFSQ YLQQCPFDEH VKLVNELTEF AKTCVADESH  60
AGCEKSLHTL FGDELCKVAS LRETYGDMAD CCEKQEPERN ECFLSHKDDS PDLPKLKPDP  120
NTLCDEFKAD EKKFWGKYLY EIARRHPYFY APELLYYANK YNGVFQECCQ AEDKGACLLP  180
KIETMREKVL TSSARQRLRC ASIQKFGERA LKAWSVARLS QKFPKAEFVE VTKLVTDLTK  240
VHKECCHGDL LECADDRADL AKYICDNQDT ISSKLKECCD KPLLEKSHCI AEVEKDAIPE  300
NLPPLTADFA EDKDVCKNYQ EAKDAFLGSF LYEYSRRHPE YAVSVLLRLA KEYEATLEEC  360
CAKDDPHACY STVFDKLKHL VDEPQNLIKQ NCDQFEKLGE YGFQNALIVR YTRKVPQVST  420
PTLVEVSRSL GKVGTRCCTK PESERMPCTE DYLSLILNRL CVLHEKTPVS EKVTKCCTES  480
LVNRRPCFSA LTPDETYVPK AFDEKLFTFH ADICTLPDTE KQIKKQTALV ELLKHKPKAT  540
EEQLKTVMEN FVAFVDKCCA ADDKEACFAV EGPKLVVSTQ TALA  584

SEQ ID NO: 10            moltype = DNA   length = 1752
FEATURE                  Location/Qualifiers
source                   1..1752
                         mol_type = other DNA
                         note = Nucleic Acid sequence of mature BSA
                         organism = Bos taurus
SEQUENCE: 10
atggataccc ataagagtga aattgcccat cgatttaagg acctcggtga agaacacttt  60
aaggggcttg tgttaatagc attctcgcag tatcttcagc aatgtccgtt tgatgaacac  120
gttaaattag tgaacgaatt aactgagttc gccaaaacgt gcgtagcgga cgaaagtcat  180
gcgggatgcg agaagagcct tcatacgctg tttggtgacg aactgtgcaa ggtggcgagt  240
ctgcgtgaaa cgtacgggga catggctgat tgctgcgaaa aacaggaacc ggaacgcaac  300
gagtgcttcc tgtctcataa agatgattcc ccggatcttc ccaaattgaa acctgacccc  360
aatacattgt gcgatgaatt taaggctgat gaaaagaaat ttgggggcaa gtatctgtat  420
gaaatcgcgc ggagacatcc ttatttctac gcaccggaac tgctgtacta cgcgaacaag  480
tataatgggg tatttcagga atgttgccag gcagaagata aaggagcctg cctgctcccc  540
aaaattgaaa ctatgcgtga gaaggtgctg acatctagcg cacggcaacg tttacgatgc  600
gcgtcaatac aaaaatttgg agaacgcgct cttaaagctt ggtctgttgc acgtctgtca  660
cagaaatttc caaaagccga gtttgtcgaa gttaccaagc tggtgacgga tcttacgaag  720
gtacataagg agtgctgtca cggcgatctg ctggagtgtg cagatgatag agctgacctt  780
gcaaagtaca tttgcgacaa tcaagatacc ataagttcga agcttaaaga gtgttgcgac  840
aaaccgctgc ttgaaaaaag ccattgtatc gcagaggtcg aaaaagatgc tatccccgaa  900
aacttaccgc cactgaccgc ggacttcgca gaggacaaag atgtttgtaa aaattatcag  960
gaggccaaag atgcatttct tgggtccttt ttgtatgagt attcacggcg acatccagaa  1020
tacgctgtct ctgtcctgct ccggctggct aaagaatatg aagcaacttt agaagaatgt  1080
tgcgccaaag atgatccgca tgcttgttac agtacggtgt ttgataaact gaaacacctc  1140
gtggatgaac ctcagaactt gataaagcaa aattgcgatc agttcgaaaa attaggtgag  1200
tacggggtcc agaatgcact gatcgttcgg tatacgcgta aagttccgca agttagcact  1260
ccaactctgg ttgaggtatc ccgcagtctc ggtaaagtcg gaactcgctg ttgcactaaa  1320
ccggaaagtg agagaatgcc gtgtactgaa gattacctga gtctgattct taatcggtta  1380
tgcgtgctgc atgaaaagac ccctgtgagt gagaaagtta ccaaatgttg tactgaatcc  1440
ctggtcaacc gccgtccgtg ctttagcgca ctcaccccag atgaaactta tgtgcctaag  1500
gcattcgatg agaaactgtt tacctttcat gcagatatct gtaccctgcc tgatactgag  1560
aaacagatta gaaacagac agctctggtg gaactcctga acataagcc aaaagccacg  1620
gaggaacagc ttaaaaccgt tatggagaat ttcgtggctt ttgtcgataa gtgttgtgcg  1680
gcggatgata agaggcgtg ctttgccgtt gaaggtccta aacttgtagt ctcaacccaa  1740
acagcgctgg ca  1752

SEQ ID NO: 11            moltype = AA   length = 584
FEATURE                  Location/Qualifiers
source                   1..584
                         mol_type = protein
                         note = Albumin Synthetic variant
                         organism = synthetic construct
SEQUENCE: 11
MDTHKSEIAH RFKDLGEEHF KALVLIAFAQ YLQQCPFDEL VKMVNELTEF AKTCVADESH  60
AGCEKSLHTL FGDELCKVAS LRETYGDMAD CCEKQEPERN ECFLSHKDDS PDLPKLKPDP  120
NTLCDEFKAD EKKFWGKYIY EIARRHPYFY APELLYYANK YNGIFQECCQ AEDKAACLLP  180
KIETIREKVL TSSARQRLRC ASLQKFGERA LKAWSVARLS QKFPKAEFVE ITKLVTDLTK  240
VHKECCHGDL LECADDRADL AKYICDNQDT ISSKLKECCD KPLLEKSHCI AEVEKDAIPE  300
NLPPLTADFL EDKDVCKNYQ EAKDAFLGSF LYEYSRRHPE YAVSVLLRLA KEYEATLEEC  360
CAKDDPHACY STVFDKLKHL IDEPQNLIKQ NCDQFEKLGE YGFQNALIIR YTRKVPQVST  420
PTLVEVTRSL GKVGTRCCTK PESERMPCTE DYLSLILNRL CVLHEKTPVS EKVTKCCTES  480
LVNRRPCFSA LTPDETYVPK AFDEKLFTFH ADICTLPDEE KQIKKQTALV ELLKHKPKAT  540
EEQLKTVMEN FVAFVDKCCA ADDKEACFAV EGPKLIVSTQ TALA  584

SEQ ID NO: 12            moltype = DNA   length = 1752
FEATURE                  Location/Qualifiers
source                   1..1752
                         mol_type = other DNA
                         note = Albumin Synthetic variant
                         organism = synthetic construct
SEQUENCE: 12
atggataccc ataagagtga aattgcccat cgttttaagg atttaggcga ggaacatttt  60
```

-continued

```
aaagctctcg tgctgattgc ctttgcacaa taccttcagc aatgtccatt cgatgaactg   120
gttaagatgg ttaatgaact taccgagttc gcaaagacgt gtgtggcgga tgaatctcac   180
gcaggttgcg aaaaaagcct gcatactctt tttggtgatg aattgtgtaa agtagcaagc   240
cttcgtgaaa cctatggtga tatggcagat tgttgcgaaa aacaagaacc ggagagaaat   300
gaatgtttct tgagtcataa ggacgattca ccggatctgc cgaagttgaa acctgaccca   360
aatacccttt gcgatgaatt taaagccgat gaaaaaaaat tctgggggaa atatatctat   420
gaaattgcta gacgccatcc ttatttttat gcgccagaat tgttgtacta cgcaaataaa   480
tacaacggga tattccagga gtgttgtcag gcagaagata aggccgcctg tctcctgcct   540
aaaatcgaga ctataagaga aaaggtcttg acttcttctg ctcgtcagag actgagatgt   600
gcaagtcttc agaaatttgg ggaaagagca ctgaaagcct ggagtgttgc acgattaagc   660
cagaaatttc ctaaagccga gtttgttgag atcacgaaac ttgtcactga ccttacgaaa   720
gttcataaag aatgttgcca cggagatctg ctggaatgtg cggatgatcg tgccgatctt   780
gctaaatata tctgtgataa ccaagataca atctcttcaa agctgaaaga atgttgtgac   840
aaacctttgt tagagaaatc acattgtatt gccgaagttg agaaagatgc cataccggaa   900
aacctcccac cgttgaccgc agactttctg gaggataagg acgtatgcaa aaattaccag   960
gaagctaagg atgcgttcct gggtagcttc ctgtatgaat attcacgccg ccaccccgag   1020
tatgcggtct cagtgctgtt acgcttagcg aaagaatacg aggccacgct ggaagaatgc   1080
tgcgcaaaag atgacccaca tgcctgttac tctacggtat ttgataaact taaacacctt   1140
attgatgaac ctcagaactt aatcaaacaa aattgtgacc agtttgagaa gctcggtgaa   1200
tatggttttc aaaatgcact cataattcgc tatacccgca aggtcccaca ggtctccacg   1260
ccgacactgg tagaagtgac ccgttcgctc ggcaaggtag aacgcgttg ttgtacgaaa   1320
cctgaaagtg aacgtatgcc ttgcacagaa gactatctgt cgctgattct caatcgttta   1380
tgcgtactgc atgaaaagac accagtctcg gaaaaagtga caaagtgctg cacggagtca   1440
ttggtcaacc gtagaccatg ttttagcgcc cttacaccgg atgaaactta tgtaccgaaa   1500
gctttcgatg agaaattatt caccttccat gcggatatct gcaccctgcc tgatgaagag   1560
aagagcatca agaaacagac agccttagtc gagttattaa agcacaaacc taaagcgacg   1620
gaagagcaac tgaaaacagt aatggaaaac tttgtggcct tcgtcgataa atgttgcgcc   1680
gcagatgata agaagcatg ttttgccgtt gaaggtccga agttaattgt tagtacccaa   1740
accgcattag ca                                                        1752
```

SEQ ID NO: 13               moltype = AA   length = 584
FEATURE                     Location/Qualifiers
source                      1..584
                            mol_type = protein
                            note = Albumin Synthetic variant
                            organism = synthetic construct
SEQUENCE: 13

```
MDTHKSEIAH RFKDLGEEHF KALVLIAFAQ YLQQCPFDEL VKMVNELTEF AKTCVADESH   60
AGCEKSLHTL FGDELCKVAS LRETYGDMAD CCEKQEPERN ECFLSHKDDS PDLPKLKPDP   120
NTLCDEFKAD EKKFWGKYIY EIARRHPYFY APELLYYANK YNGIFQECCQ AEDKAACLLP   180
KIETIREKVL TSSARQRLRC ASLQKFGERA LKAWSVARLS QKFPKAEFVE ITKLVTDLTK   240
IYKECCHGDL LECMDDRADL VKYICDNQDT ISSKLKECCD KPLLEKSHCI AEVEKDAIPE   300
NLPPLTADFL EDKDVCKNYQ EAKDAFLGSF LYEYSRRHPE YAVSLLLRLA KEYEATLEEC   360
CAKDDPHACY STVFDKLKHL IDEPQNLIKQ NCDQFEKLGE YGFQNALIIR YTRKMPQVST   420
PTLVEITRSL GKVGTRCCTL PESERLPCTE DYLSLILNRL CVLHEKTPVS EKVTKCCTES   480
LVNRRHCFSA LTPDETYVPK AFDEKLFTFH ADICTLPDEE KQIKKQTFLV ELLKHKPKAT   540
EEQLKTIMEN FTAFVDKCCA ADDKEACFAV EGPKLIVSTQ TALA                     584
```

SEQ ID NO: 14               moltype = DNA   length = 1752
FEATURE                     Location/Qualifiers
source                      1..1752
                            mol_type = other DNA
                            note = Albumin Synthetic variant
                            organism = synthetic construct
SEQUENCE: 14

```
atggataccc ataagagtga aattgcccat cgctttaaag atctcggga ggagcacttt    60
aaagcccttg tcctgatcgc cttcgcacag tatctgcaac agtgcccttt tgatgaattg   120
gtcaagatgg ttaatgaatt aaccgagttc gctaaaactt gcgtcgctga tgagtctcac   180
gcaggatgcg agaaatcact gcatacattg ttcggtgatg aattgtgcaa ggtcgctagc   240
ttgcgtgaaa cctacggcga tatggccgat tgctgtgaaa aacagagacc ggagcgtaat   300
gagtgtttct taagtcacaa ggatgattct ccagatcttc aaagttaaa accagatcca    360
aatactcttt gtgatgagtt caaagcggat gaaaagaaat tttgggggtaa atacatctac   420
gagattgccc gtcggcatcc ctacttctat gccccggaac tgctgtacta tgcgaataag   480
tataacggga ttttccagga atgttgtcaa gctgaagata agccgcttg tctgctgcct    540
aaaattgaga caattcggga aaaagtactg acgagctccg cacgtcaacg cctgcgatgc   600
gcgagtctgc aaaagtttgg tgaacgtgct cttaaagcct ggagcgtcgc gcgactctca   660
cagaaatttc caaaagcaga gtttgtcgaa attaccaaac ttgtcactga cctgaccaag   720
atatataagg aatgctgcca cggcgatttg ctggagtgca tggatgatcg ggccgactta   780
gtgaaatata tatgtgacaa ccaagatacc atatcaagca agctgaaaga tgtttgtgat   840
aagccgttgc tcgaaaagtc gcactgcatt gcggaggtcg aaaaagacg tatccctgaa    900
aacttaccgc cgttaacagc cgattttctt gaagacaaag acgtttgcaa aaactatcag   960
gaagccaaag atgcatttct cggcagtttc ttatatgagt actccagacg ccaccccgaa   1020
tatgcagttt cgcttctctt aagacttgca aaagaatacg aggccaccct ggaggagtgc   1080
tgtgctaaag atgacccaca tgcatgttat tctaccgtgt ttgataaact gaagcatctt   1140
atcgacgagc cccagaatct gatcaaacag aattgcgacc aattcgagaa attaggtgag   1200
tatggtttcc aaaacgcgct catcatccga tacacccgca agatgccgca agtctcaacc   1260
cctacactgg tggagatcac ccgcagcctg ggtaaagtgg gtacgcgatg tctgtaccctc   1320
ccggaaagcg aacgtcttcc ttgtacagaa gactactat cgctcatatt aaaccgtctg    1380
tgcgttttgc acgaaaagac ccctgtttcg gagaaggtga ccaaatgttg cactgaaagt   1440
```

-continued

```
ctggttaatc ggcggcattg cttctctgcg ctgacacctg atgaaaccta tgtaccaaaa   1500
gcctttgatg aaaagttatt tacgtttcac gccgacattt gcacactgcc ggatgaggaa   1560
aaacagatca agaaacaaac ttttctggta gaactgctga aacataagcc gaaagcaacg   1620
gaagaacagt taaaaaccat tatggagaac tttaccgcgt tcgtggataa gtgctgtgcc   1680
gcagacgata aagaagcctg ttttgcagtg gagggaccga aactgatagt tagcacccaa   1740
accgcgctcg cg                                                       1752
```

```
SEQ ID NO: 15          moltype = AA  length = 584
FEATURE                Location/Qualifiers
source                 1..584
                       mol_type = protein
                       note = Albumin Synthetic variant
                       organism = synthetic construct
SEQUENCE: 15
MDTHKSEIAH RFKDLGEEHF KALVLIAFAQ YLQKCPFDEL VKMVNDLTEF AKKCVADESH   60
PGCSKSLHTL FGDELCKVEE LRETYGDMAD CCSKQEPERN ECFLSHKDDN PDLPKLKPDP   120
NTLCKEFKED EKKFWGKYIY EIARRHPYFY APELLYYAKK YNKIFQECCQ AEDKAACLLP   180
KIEAIREKVK TSSARQRLRC ASLQKFGERA LKAWFVARLS QKFPKAPFEE ITKLVTDLTK   240
IYKECCHGDL LECMDDRAKL VKYICDNQDT ISSKLKECCD KPLLERSHCI AEVEDDDIPE   300
DLPPLVADFL EDKDVCKNYQ EDKDAFLGRF LYEYSRRHPE YAVSLLLRLA KEYEATLEEC   360
CKKDDDPHACY SRVFEKLKKH IDEPQELIKQ NCDQFEKLGE YGFQNALIIR YTKKMPQVPT   420
DTLVEITRSL GKVGTRCCQL PEEKRLPCTE DYLSLILNRL CVLHEKTPVS EKVTKCCTES   480
LVNRRHCFSA LTPDETYVPK PFDPKLFTFH ADICTLPPEE KQIKKQKFLV ELLKHKPKAT   540
EEQLKTIMEN FTAMVDKCCK AEDKEACFAE EGPKLIEKTQ AALA                    584
```

```
SEQ ID NO: 16          moltype = DNA  length = 1752
FEATURE                Location/Qualifiers
source                 1..1752
                       mol_type = other DNA
                       note = Albumin Synthetic variant
                       organism = synthetic construct
SEQUENCE: 16
atggataccc ataagagtga aattgcccat cgtttcaaag accttggaga agaacacttt   60
aaagctctcg tgctcattgc cttcgcgcaa tatctccaaa agtgtccttt tgatgagttg   120
gtaaagatgg taaacgattt gacagagttt gcgaagaaat gtgttgcgga tgaatcgcat   180
ccaggttgca gtaagagcct gcacactctg tttggagatg aactttgtaa agtagaggaa   240
ctgcgagaaa cctacggaga tatggctgac tgttgcagca acaggagcc tgaacggaat    300
gaatgcttct ctcccataa ggacgacaat cccgacttgc cgaaattgaa gcccgatccg    360
aacactctgt gcaaagaatt taaagaagat gaaaagaaat tttggggcaa atacatttat    420
gaaatagccc gccggcatcc gtatttctat gccccggaat tactttatta tgcgaagaaa    480
tataacaaaa tctttcaaga atgctgccag gctgaagata aagcagcttg cttgctcccg    540
aaaattgaag cgattcggga aaaagtgaaa acttcttcag ctcgccagcg tctgcgttgt    600
gcttcattac agaaatttgg cgaacgggct ctgaaagcct ggtttgtcgc acgtctgtca    660
cagaagtttc ccaaggctcc gtttgaggaa attacgaagt tggtcacaga cttaacaaaa   720
atttataaag aatgttgtca cggtgatctg ctggaatgta tggatgatcg tgccaagctg    780
gtaaagtaca tttgtgataa tcaagatacg ataagttcaa agttaaagga gtgttgcgat    840
aaaccacttt tagagagaag tcactgtatt gcggaagtcg aggatgaga tatcccggag     900
gacctccctc ctcttgtagc ggattttctg gaggataaag atgtctgtaa aaattatcag    960
gaagataaag acgcttttct tggccgtttt ttatacgaat atagcagacg tcaccccgaa   1020
tatgctgtgt ctttgttgct tcgccttgca aaggagtacg aagcaactct ggaggaatgc   1080
tgtaaaaaag acgatccaca cgcttgttat agtcgggtct ttgagaaact gaagaaacat   1140
atagatgagc cgcaagaact gataaaacag aactgcgacc agtttgagaa gctgggggaa   1200
tacggcttcc aaaatgcatt gataattaga tacactaaaa agatgccgca agtgccgacg   1260
gatacctctg ttgagataac tcggagttta ggaaaagtag gcacacggtg ttgccagctt   1320
ccggaagaaa aacgcttgcc ttgcactgag gactatttat ccctcatttt aaaccggctg   1380
tgcgtacttc atgaaaagac tccagtgagt gagaaggtta ccaaatgttg cactgaaagc   1440
ctggtgaata gacgtcactg ttttttcagcg ttaactccag atgaaactta tgtccccaaa   1500
cctttgatc ctaaattgtt cacctttcac gctgatatat gtaccttacc tcccgaagaa   1560
aaacagatca agaagcagaa attttggtg gaactttga aacataagcc gaaagctacc    1620
gaagaacagt tgaaaactat tatggaaaac tttacagcta tggtcgataa gtgttgtaaa   1680
gctgaggata agaagcttg ttttgccgaa gagggaccaa aactgattga gaaaacccaa   1740
gcggccctgg ct                                                       1752
```

```
SEQ ID NO: 17          moltype = AA  length = 585
FEATURE                Location/Qualifiers
source                 1..585
                       mol_type = protein
                       note = Design 7 - raw design of HSA
                       organism = synthetic construct
SEQUENCE: 17
DAHKSEVAHR FKDLGEENFK ALVLIAFAQY LQKCPFEELV KMVKEVTEFA KKCVADETAE   60
NCDKSLHTLF GDKLCQVATL RETYGEMADC CAKQDPERHE CFLQHKDDNP NLPRLERPEV   120
DVMCKAFHDN EETFLNKYLY EIARRHPYFY APELLYFAKR YKKAFTECCQ AEDKAACLLP   180
KLDALREEGK ESSAKQRYKC AILQKFGERV FKAWAIARLS QRFPKAPFEE ISKLVTDLTK   240
VHKACCHGDM LECMDDRAKL AKYICENQDS ISSKLKECCE KPLLERSHCI AEVENDDKPE   300
DLPPLAADFV ESKDVCKNYA EAKDVFLARF LYEYARRHPD YSVTLLLRIA KTYEDTLEKC   360
CKAEDPHECY AKVEEEFKKL VEETQNLIKQ NCELFEKLGE YYFQNALLIR YTKKMPQVPT   420
DTLVELTRNL GKVGSKCCKL PEEKRLPCIE DYLSIVLNQL CVLHEKTPVN DRVTKCCTES   480
LVNRRHCFSA LEVDETYVPK EFNAETFTFH ADLCTLSEEE RQIMKQKFLV ELVKHKPKAT   540
```

-continued

```
EEQLKAVMDD FTAFVEKCCK AEDPETCFAE EGSKLIAKSQ AALGL            585

SEQ ID NO: 18        moltype = AA   length = 583
FEATURE              Location/Qualifiers
source               1..583
                     mol_type = protein
                     note = Design 6 - raw design of BSA
                     organism = synthetic construct
SEQUENCE: 18
DTHKSEIAHR FKDLGEEHFK GLVLIAFAQY LQKCPFDELV KLVNDLTEFA KKCVADESHP  60
GCSKSLHTLF GDEICKVEEL RETYGDMADC CSKQEPERNE CFLSHKDDNP DLPKLKPDPN  120
TLCKEFKEDE KKFWGKYIYE IARRHPYFYA PELLYYAAKY NKVFQECCQA EDKAACLLPK  180
IEAIREKVKT SSARQRLRCA SLQKFGERAL KAWFVARLSQ KFPKAPFEEI TKLVTDLTKI  240
YKECCHGDLL ECMDDRAKLV KYICDNQDTI SSKLKECCDK PLLERSHCIA ELEFDDIPED  300
LPPLVADFLE DKDVCKNYQE DKDAFLGRFL YEYSRRHPEY AVSLLLRLAK VYEATLEECC  360
KKDDPHACYS RVFEKLKKHI DEPQNLVKQN CDQFEKLGEY GFQNALIIRY TKKMPQVPTD  420
TLVEVSRSLG KVGTRCCQLP EEKRLPCTED YLSLILNRLC VLHEKTPVSE KVTKCCTESL  480
VNRRHCFSAL TPDETYVPKP FDPKLFTFHA DICTLPPEEL QIKKQKFLVE LLKHKPKATE  540
EQLKTVMENF TAMVDKCCKA EDKEACFAEE GPKLIEKTQA ALA                    583
```